United States Patent [19]

Hayashi et al.

[11] 4,065,632
[45] Dec. 27, 1977

[54] 16-PHENOXY AND PHENYLTHIO PROSTAGLANDIN DERIVATIVES

[75] Inventors: Masaki Hayashi; Seiji Kori; Hajimu Miyake; Takanori Okada, all of Osaka, Japan

[73] Assignee: Ono Pharmaceutical Company, Osaka, Japan

[21] Appl. No.: 713,941

[22] Filed: Aug. 12, 1976

[30] Foreign Application Priority Data

Aug. 20, 1975  United Kingdom ............... 34688/75
Oct. 22, 1975  United Kingdom ............... 43464/75

[51] Int. Cl.² ........................................ C07C 69/76
[52] U.S. Cl. .............................. 560/55; 260/345.7 P; 260/345.8 P; 260/347.3; 260/347.9; 424/305; 424/308; 424/317; 260/516; 260/520 R; 260/520 C; 542/426
[58] Field of Search ........... 260/473 R, 473 A, 520 R, 260/520 C

[56] References Cited
PUBLICATIONS

Derwent Abst. 46497 w/28, 3/7/75.
Derwent Abst. 73279 U-B, 10/5/72.

*Primary Examiner*—Paul J. Killos
*Attorney, Agent, or Firm*—Albert H. Graddis; Frank S. Chow

[57] ABSTRACT

The present invention relates to compounds of the formula:

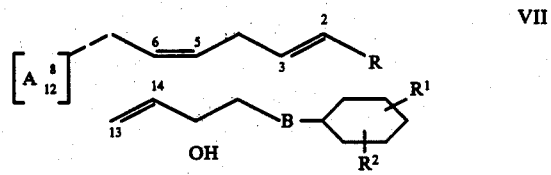

wherein A represents a grouping of the formula:

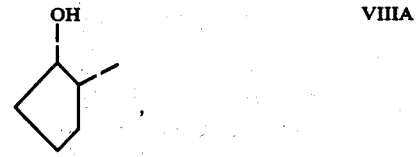

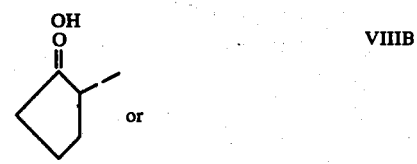

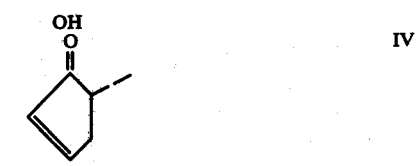

B represents an oxygen or sulphur atom, $R^1$ and $R^2$, which may be the same or different, each represent a hydrogen or halogen atom, a trifluoromethyl group, or a straight- or branched-chain alkyl or alkoxy group containing from 1 to 4 carbon atoms, R represents a group of the formula —COOR³, in which $R^3$ represents a hydrogen atom or a straight- or branched-chain alkyl group containing from 1 to 12 carbon atoms, or a group of the formula —CH₂OR⁴, in which $R^4$ represents a hydrogen atom or an alkylcarbonyl group containing from 2 to 5 carbon atoms and the double bonds depicted in positions $C_2$-$C_3$, $C_5$-$C_6$ and $C_{13}$-$C_{14}$ are trans, cis and trans respectively, the cyclodextrin clathrates thereof and, when $R^3$ in the group —COOR³ represents a hydrogen atom, non-toxic salts thereof. These compounds exhibit characteristics of prostaglandin-like activity.

9 Claims, No Drawings

16-PHENOXY AND PHENYLTHIO PROSTAGLANDIN DERIVATIVES

This invention is concerned with new prostaglandin analogues.

Prostaglandins are derivatives of prostanoic acid which has the following formula:

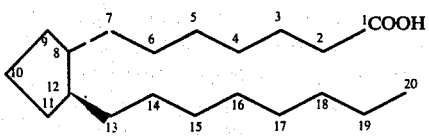

Various types of prostaglandins are known, the types depending inter alia on the structure and substituents on the alicyclic ring. For example, the alicylic rings of prostaglandins F(PGF), E(PGE), and A(PGA) have the structures:

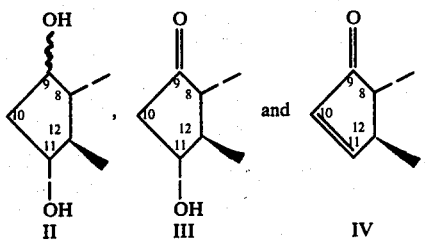

respectively. The dotted lines in the foregoing formulae and in other formulae throughout this specification denote, in accordance with generally accepted rules of nomenclature, that the attached grouping lies behind the general plane of the ring system, i.e. that the grouping is in α-configuration, the thickened lines ⬛ denote that the grouping lies in front of the general plane of the system, i.e. that the grouping is in β-configuration, and the wavy line ～ indicates that the grouping is in α- or β-configuration.

Such compounds are sub-classified according to the position of double bond(s) in the side chain(s) attached to the 8- and 12-positions of the alicylic ring. Thus $PG_1$ compounds have a trans-double bond between $C_{13}$-$C_{14}$ (trans-$\Delta^{13}$) and $PG_2$ compounds have a cis-double bond between $C_5$-$C_6$ and a trans-double bond between $C_{13}$-$C_{14}$ (cis-$\Delta^5$, trans-$\Delta^{13}$). For example, prostaglandin $F_{1\alpha}$ ($PGF_{1\alpha}$) and prostaglandin $E_1$ ($PGE_1$) are characterized by the following structures V and VI.

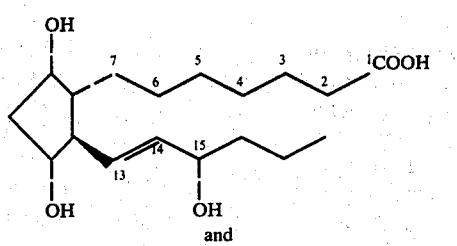

and

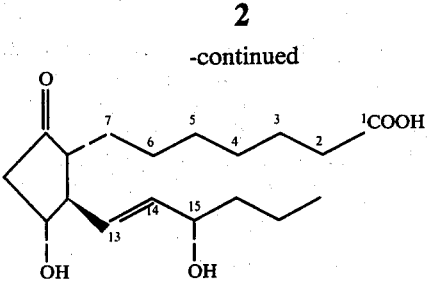

respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene are known as dihydroprostaglandins, e.g. dihydroprostaglandin-$F_{1\alpha}$ (dihydro-$PGF_{1\alpha}$) and dihydroprostaglandin-$E_1$ (dihydro-$PGE_1$).

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di-, tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs and PGAs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PFGs may be used as oxytocics, as abortifacients in the first and second trimesters; in the post-labour abortion of the placenta, and as oral contraceptives because they regulate the sexual cycle of female mammals. PGEs and PGAs have vasodilator and diuretic activities. PGEs are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree. It has now been found that by replacing the n-butyl group at the end of the aliphatic group linked to the 12-position of the alicyclic ring of prostaglandins $F_{2\alpha}$, $E_2$ and $A_2$ by an optionally substituted phenoxy or phenylthio group, introducing a trans-double bond between the carbon atoms in the 2- and 3-positions of such prostaglandins and optionally replacing the carboxy group (-COOH) on the aliphatic group attached to the 8-position of such prostaglandins by a hydroxymethyl (—CH$_2$OH) or acylated hydroxymethyl group, new prostaglandin analogues are obtained which possess the pharmacological properties of the 'natural' prostaglandins and are, in some aspects of their activities, an improvement, for example they possess an enhanced strength of activity or a prolonged duration of activity.

The present invention accordingly provides the new prostaglandin analogues of the general formula:

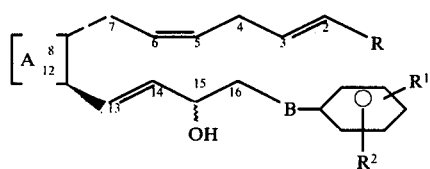

VII (wherein A represents a grouping of formula IV as indicated hereinbefore or a grouping of the formula:

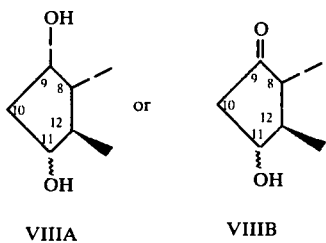

VIIIA    VIIIB

B represents an oxygen or sulphur atom, $R^1$ and $R^2$, which may be the same or different, each represent a hydrogen or halogen atom, a trifluoromethyl group, or a straight- or branched-chain alkyl or alkoxy group containing from 1 to 4 carbon atoms, and R represents a group of the formula —COOR$^3$, in which $R^3$ represents a hydrogen atom or a straight- or branched-chain alkyl group containing from 1 to 12 carbon atoms, or a group of the formula —CH$_2$OR$^4$, in which $R^4$ represents a hydrogen atom or an alkylcarbonyl group containing from 2 to 5 carbon atoms) and cyclodextrin clathrates of such prostaglandin analogues and, when $R^3$ in the group —COOR$^3$ represents a hydrogen atomm, non-toxic (e.g. sodium) salts thereof. It is to be understood that in general formula VII and formulae subsequently appearing in this specification the double bonds depicted in positions $C_2$-$C_3$, $C_5$-$C_6$ and $C_{13}$-$C_{14}$ are trans, cis and trans respectively. Preferably A represents a grouping of formula VIIIA, preferably B represents an oxygen atom, preferably $R^1$ represents a hydrogen atom, preferably $R^2$ represents a hydrogen or chlorine atom or a trifluoromethyl group, preferably $R^3$ represents a hydrogen atom or a straight- or branched-chain alkyl group containing 1 to 4 carbon atoms, advantageously a methyl group, preferably $R^4$ represents a hydrogen atom and preferably the hydroxy groups depicted in formulae VII, VIIIA and VIIIB in α- or β-configuration are attached to the carbon atom in α-configuration.

The present invention is concerned with all compounds of general formula VII in the 'natural' form or its enantiomeric form, or mixtures thereof, more particularly the racemic form, consisting of equimolecular mixtures of natural and its enantiomeric form.

As will be apparent to those skilled in the art, the compounds depicted in general formula VII have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries hydroxy groups on the carbon atoms in positions 9 and 11 (i.e. when the ring is that of formula VIIIA) or a hydroxy group in position 11 (i.e. when the ring is that of formula VIIIB). The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration and have a hydroxy group as depicted in the 15-position are to be considered within the scope of general formula VII.

According to a feature of the present invention, the prostaglandin analogues of general formula VII, wherein B represents an oxygen atom and R represents a group —COOR$^3$, in which $R^3$ is as hereinbefore defined, and the other symbols are as hereinbefore defined, i.e. compounds of the general formula:

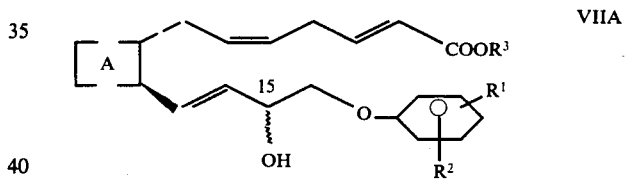

VIIA (wherein the various symbols are as hereinbefore defined) are prepared by the process which comprises hydrolyzing a cyclopentane derivative of the general formula:

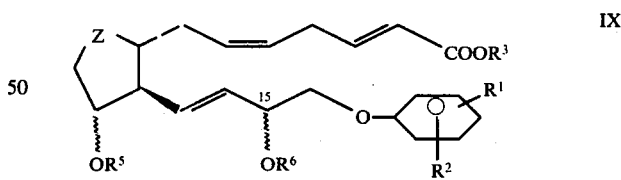

IX (wherein Z represents

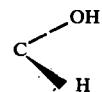

or C=O, $R^5$ represents a 2-tetrahydrofuranyl group, a 1-ethoxyethyl group or a 2-tetrahydropyranyl group unsubstituted or substituted by at least one alkyl group, $R^6$ represents a hydrogen atom, a 2-tetrahydrofuranyl group, a 1-ethoxyethyl group or a 2-tetrahydropyranyl group unsubstituted or substituted by at least one alkyl group, and the other symbols are as hereinbefore defined) to convert to a hydroxy group the group OR⁵ and, when R⁶ is a 2-tetrahydrofuranyl or 1-ethoxyethyl group, or a 2-tetrahydropranyl group unsubstituted or substituted by at least one alkyl group, the group OR⁶ to obtain a PGF or PGE compound of the general formula:

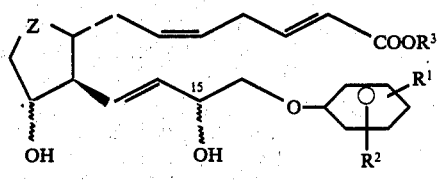

VIIB (wherein the various symbols are as hereinbefore defined), and, if desired, converting by methods known per se the PGE alicyclic ring of a compound of general formula VIIB (Z represents C=O) to that of a PGA compound. By the term 'methods known per se' as used in this specification is meant methods heretofore used or described in the chemical literature.

The groups OR⁵ and OR⁶ (when R⁶ is other than a hydrogen atom) of the compounds of general formula IX (preferably such groups are 2-tetrahydropyranyl) may be converted to hydroxy groups by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60° C. (preferably at a temperature below 45° C.) with an acid mixture, e.g. a mixture of hydrochloric acid with tetrahydrofuran or methanol, or a mixture of acetic acid, water and tetrahydrofuran. The products of formula VIIB may be purified by column chromatography on silica gel, which procedure may, when the starting material of formula IX is a mixture of compounds with the OR⁶ group in the 15-position in α- and β-configurations, lead to a separation of the resulting 15α-hydroxy and 15β-hydroxy isomers of formula VIIB.

The PGE compounds of general formula VIIB (Z represents C=O) can be converted into the corresponding PGA compounds of general formula VII, wherein A represents a grouping of formula IV, by subjecting the PGEs to dehydration using an aqueous solution of an organic or inorganic acid having a higher concentration than that employed for hydrolysing the groups OR⁵ and OR⁶ (when R⁶ is other than a hydrogen atom) of compounds of general formula IX, e.g. 1N hydrochloric acid or acetic acid, and heating at a temperature of 30°-60° C. If desired, simultaneous hydrolysis and dehydration under acidic conditions as hereinbefore described may be effected on compounds of general formula IX, wherein Z represents C=O and the other symbols are as hereinbefore defined, to product directly PGA compounds of formula VII (A represents a grouping of formula IV).

Compounds of general formula VIIB, wherein R³ represents an alkyl group containing from 1 to 12 carbon atoms and Z represents C=O, may, if desired, be converted to corresponding acids of general formula VIIB, i.e. R³ represents a hydrogen atom, by treatment with baker's yeast [c.f. C. J. Sih et al., J. Amer. Chem. Soc., 94, 3643 (1972)].

Compounds of general formula IX, wherein Z represents

and the other symbols are as hereinbefore defined, i.e. compounds of the general formula:

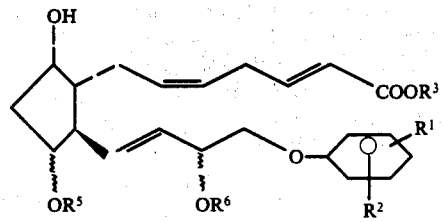

IXA (wherein the various symbols are as hereinbefore defined) may be prepared by the process which comprises reacting a compound of the general formula:

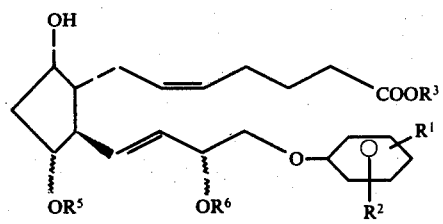

X (wherein the various symbols are as hereinbefore defined) with a compound of the general formula:

XI (wherein R⁷ and R⁸ each represents an alkyl group containing from 1 to 6 carbon atoms or a cycloalkyl group containing from 3 to 6 carbon atoms) to obtain a lithium esterenolate of the general formula:

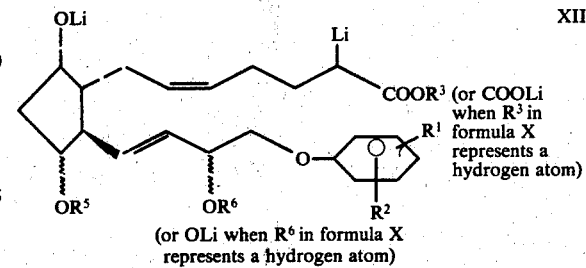

XII (or OLi when R⁶ in formula X represents a hydrogen atom)

(wherein the various symbols are as hereinbefore defined), reacting the lithium esterenolate with benzenselenenyl bromide (i.e. φSeBr in which φ represents the phenyl radical) or diphenyldiselenide or a dialkyl- or diphenyl-disulphide of the formula R⁹SSR⁹, wherein the symbols R⁹ both represent alkyl groups containing from 1 to 4 carbon atoms or phenyl radicals, hydrolyzing the resulting intermediate to obtain a compound of the general formula:

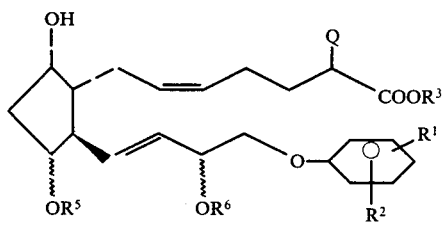

XIII (wherein Q represents —Seφ, in which φ is as hereinbefore defined, or a group —SR⁹, in which R⁹ is as hereinbefore defined, and the other symbols are as hereinbefore defined), treating the resulting compound with hydrogen peroxide or sodium periodate, and decomposing the resulting compound of the general formula:

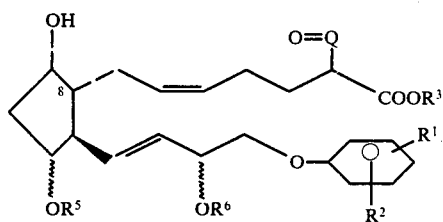

XIV (wherein the various symbols are as hereinbefore defined) to convert the grouping

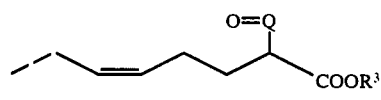

attached to the 8-position of the cyclopentane ring to a trans-Δ²-grouping

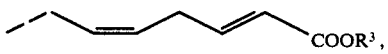

wherein $R^3$ is as hereinbefore defined.

The reaction between the prostaglandin compound of general formula X and the lithiated amine of general formula XI is carried out in an organic solvent medium, for example, when $R^3$ represents an alkyl group, by adding dropwise a solution of a prostaglandin ester of formula X in tetrahydrofuran to a solution of an amine of formula Xi in tetrahydrofuran at a low temperature, e.g. −78° C., or, when $R^3$ in general formula X represents a hydrogen atom, in tetrahydrofuran in the presence of hexamethylphosphoramide at 0° C., the ratio of the molecular equivalents of the compounds of formula X to XI in the reaction mixture being suitably adjusted to obtain a lithium esterenolate of formula XII. In the case where a prostaglandin ester is employed as reactant, after completion of the addition of the prostaglandin solution to the amine solution, the reaction mixture is stirred at the same temperature for about 30 minutes to obtain a solution of the lithium esterenolate of formula XII. In the case where a prostaglandin acid is employed as reactant ($R^3$ represents a hydrogen atom), the reaction mixture is stirred at room temperature for about 30 minutes to obtain a solution of the lthium esterenolate of formula XII.

The reaction between the lithium esterenolate of formula XII and benzeneselenenyl bromide, diphenyldiselenide or a dialkyl- or diphenyl-disulphide, is preferably carried out in tetrahydrofuran, hexamethylphosphoramide, diethyl ether, n-pentane or n-hexane or a mixture of two or more of them, tetrahydrofuran being the preferred solvent medium, at a low temperature when $R^3$ in formula XII represents an alkyl group, e.g. −78° C., or, when $R^3$ in formula XII represents a hydrogen atom, at 0° C. Thus, to the lithium esterenolate solution obtained as described above there is added a solution in tetrahydrofuran of benzeneselenenyl bromide, diphenyldiselenide or a dialkyl- or diphenyldisulphide, the temperature of the two solutions being −78° C. or 0° C. according to whether an ester or acid of formula XII, respectively, is the reactant. The reaction mixture is then stirred (when $R^3$ in formula XII is an alkyl group) at −78° C. (a) for one hour when a selenium compound is the reactant or (b) for 30 minutes when a disulphide is the reactant, and subsequently at ambient temperature, e.g. 15° C. for 30 minutes, or (when $R^3$ in formula XII is a hydrogen atom) at room temperature for 1 hour 30 minutes. After addition of, for example, a small amount of a saturated aqueous ammonium chloride solution to the solution of the resulting prostaglandin intermediate to hydrolyze it, the product of formula XIII is extracted with ethyl acetate.

If desired, the intermediate esters of general formula XIII wherein $R^3$ represents an alkyl group may be converted to corresponding acids of general formula XIII, i.e. $R^3$ represents a hydrogen atom, by hydrolysis under alkaline conditions. The hydrolysis of the esters under alkaline conditions may be effected with an aqueous solution of an alkali metal, e.g. sodium or potassium, hydroxide or carbonate in the presence of a water-miscible organic solvent, e.g. tetrahydrofuran or an alkanol containing from 1 to 4 carbon atoms, e.g. methanol.

When the product of formula XIII is a compound wherein Q represents —Seφ, φ being as hereinbefore defined, the product is then treated with 5 to 7 molecular equivalents of hydrogen peroxide in a mixture of ethyl acetate and tetrahydrofuran or methanol at a temperature of 30° C. or below, or with 5 molecular equivalents of sodium periodate in the presence of a lower alkanol, preferably ethanol, and water, at a temperature below 20° C., preferably for about 24 hours, to form a compound of formula XIV wherein O═Q— represents —Se(O)φ, and stirring of the reaction mixture at a temperature of 25° to 30° C. for 1 hour results in decomposition of the compound to a trans-Δ²-prostaglandin analogue of general formula IXA, which can be separated from the reaction medium by methods known per se and, if desired, purified by column chromatography on silica gel.

When the product of formula XIII is a compound wherein Q is a group —SR⁹, R⁹ being as hereinbefore defined, the product is treated with hydrogen peroxide or sodium periodate in the same way as hereinbefore described for a product of formula XIII wherein Q is phenylseleno to obtain a compound of general formula XIV wherein Q is a group —SR⁹, R⁹ being as hereinbefore defined, which can be separated from the reaction medium by methods known per se.

When the compound of formula XIV is one wherein Q represents an alkylthio group —SR⁹′, wherein R⁹′ represents an alkyl group containing from 1 to 4 carbon atoms, the compound is dissolved in toluene and the solution stirred, preferably in the presence of a small amount of calcium carbonate, at a temperature of 100° to 120° C. for a period ranging from 5 to 24 hours to decompose the compound to a trans-Δ²-prostaglandin analogue of general formula IXA. When the compound of general formula XIV is one wherein Q represents the phenylthio group, the compound is dissolved in carbon tetrachloride and the solution stirred, preferably in the presence of a small amount of calcium carbonate, at a temperature of about 50° C. for a period ranging from 5 to 24 hours to decompose the compound to a trans-Δ²—prostaglandin analogue of general formula IXA.

Compounds of general formula IX, wherein $R^5$ and $R^6$ each represent a 2-tetrahydrofuranyl group a 1-ethoxyethyl group or a 2-tetrahydropyranyl group unsubstituted or substituted by at least one alkyl group and Z represents C=O, may be obtained from compounds of general formula IX, wherein $R^5$ and $R^6$ each represent a 2-tetrahydrofuranyl group, a 1-ethoxyethyl group or a 2-tetrahydropyranyl group unsubstituted or substituted by at least one alkyl group and Z represents

by methods known per se for the conversion of a hydroxy group in the 9-position of a prostaglandin compound to an oxo group, for example by means of a chromic acid solution (e.g. obtained from chromium trioxide, manganese sulphate, sulphuric acid and water) or Jones' reagent.

The method hereinbefore described for the preparation of prostaglandin analogues of general formula VII may be represented by the series of reactions depicted schematically below in Scheme A, wherein $R^{6'}$ represents a 2-tetrahydrofuranyl group, a 1-ethoxyethyl group or a 2-tetrahydropyranyl group unsubstituted or substituted by at least one alkyl group, and the other symbols are as hereinbefore defined.

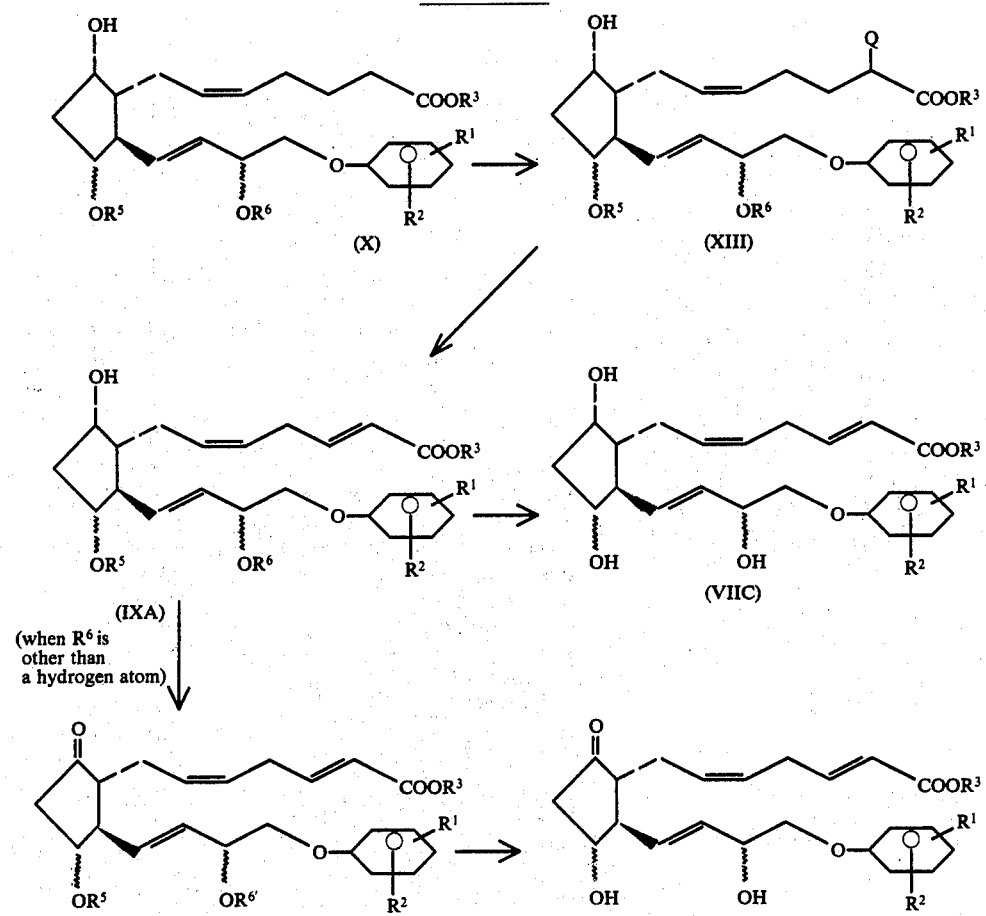

-continued

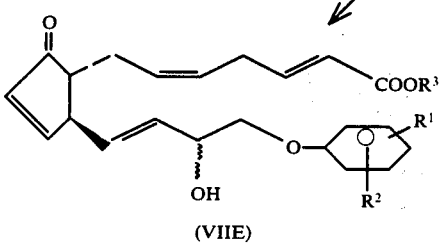

(VIIE)

The starting materials of general formula X, wherein $R^5$ and $R^6$ each represent a 2-tetrahydrofuranyl group, a 1-ethoxyethyl group or a 2-tetrahydropyranyl group unsubstituted or substituted by at least one alkyl group, $R^3$ represents a straight- or branched-chain alkyl group containing from 1 to 2 carbon atoms and the other symbols are as hereinbefore defined, may be prepared from the corresponding acids of the general formula:

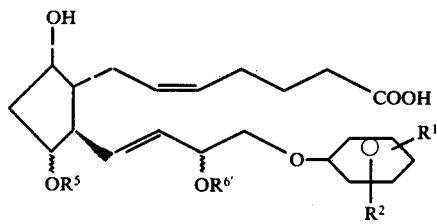

XA (wherein the various symbols are as hereinbefore defined) by esterification, for example by reaction with (i) the appropriate diazoalkane compound, e.g. diazomethane in an inert solvent, e.g. diethyl ether, at a temperature of from −10° to 25° C., and preferably 0° C., (ii) the appropriate alcohol in the presence of dicylcohexyl-carbodiimide as condensing agent, or (iii) the appropriate alcohol following the formation of a mixed acid anhydride by adding a tertiary amine and then a pivaloyl halide or an arylsulphonyl or alkylsulphonyl halide (cf. our British Pat. Nos. 1362956 and 1364125).

Compounds of general formula XA, wherein the various symbols are as hereinbefore defined, may be prepared by reacting a bicyclo-octane derivative of the general formula:

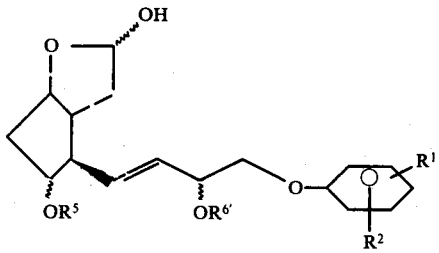

XV (wherein the various symbols are as hereinbefore defined) with (4-carboxybutylidene)triphenylphosphorane of the formula $\phi_3P=CH-(CH_2)_3-COOH$ (wherein $\phi$ is as hereinbefore defined). The reaction between the bicyclo-octane of general formula XV and (4-carboxybutylidene)triphenyl-phosphorane [obtained by the reaction of sodium methylsulphinylmethylide with (4-carboxybutyl)triphenyl-phosphonium bromide] is carried out under the normal conditions utilized for effecting the Wittig reaction, e.g. in an inert solvent at ambient temperature. The reaction is preferably carried out in dimethyl sulphoxide because the phosphorane compound is practically insoluble in other solvents, e.g. tetrahydrofuran, and because a cis-double bond must be formed stereospecifically in the Witting reaction. For the better performance of the Wittig reaction more than two molecular equivalents of the phosphorane compound are required for each mole of the bicyclo-octane reactant. The reaction is generally effected at a temperature of 10°–40° C., preferably at 20°–30° C., and is usually complete after about 30 minutes to 4 hours at laboratory temperature. The acid product of formula XA may be extracted from the reaction mixture by conventional procedures and further purified by column chromatography on silica gel.

Compounds of general formula XV, wherein the group $OR^5$ is in α-configuration and the various symbols are as hereinbefore defined [hereinafter depicted in formula XVA], may be prepared from 2-oxa-3-oxo-6-syn-formyl-7-anti-acetoxy-cis-bicyclo[3,3,0]octane [E. J. Corey et al., J. Amer. Chem. Soc., 91, 5675 (1969) and ibid 92, 397 (1980) and French Patent Application No. 72 15314 (Publication No. 2134673)] by the series of reactions depicted schematically below in Scheme B:

SCHEME B

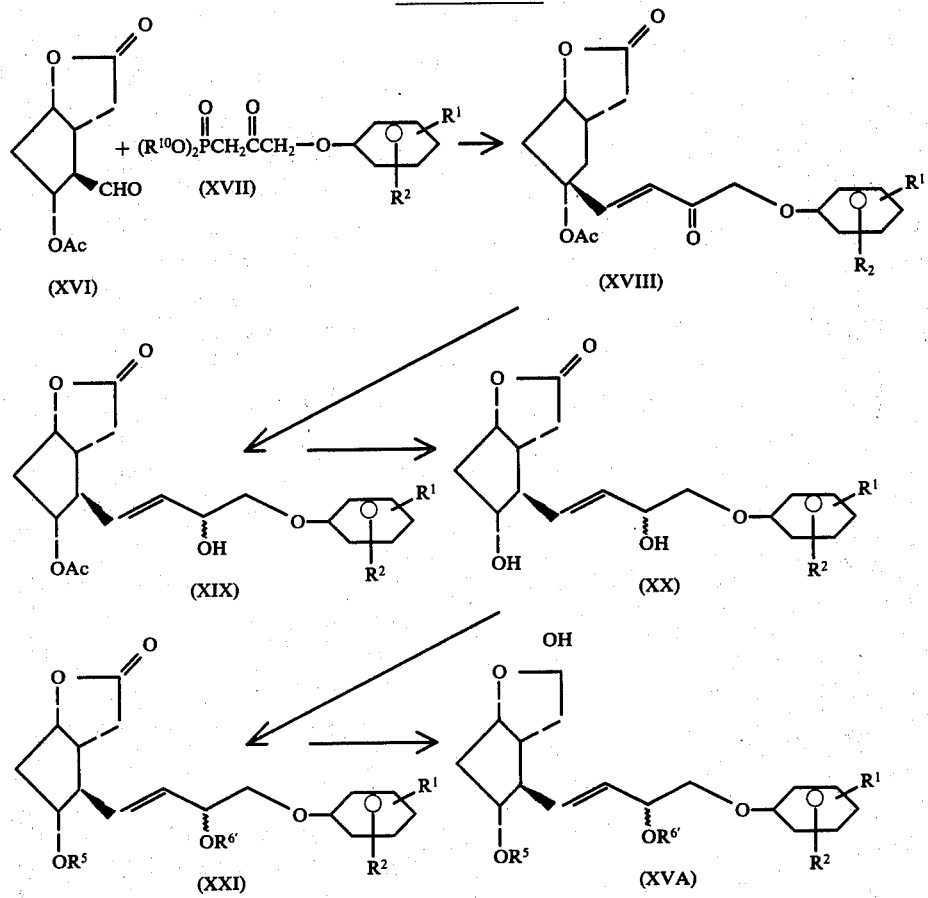

wherein $R^{10}$ represents an alkyl group containing from 1 to 4 carbon atoms, Ac represents the acetyl group (—COCH$_3$), and the various other symbols are as hereinbefore defined.

The reaction of a compound of general formula XVI with a dialkyl phosphonate of general formula XVII is preferably effected by suspending sodium hydride in an inert organic solvent, e.g. tetrahydrofuran or 1,2-dimethoxyethane, and adding the dialkyl phosphonate of general formula XVII. The resulting sodio derivative of the dialkyl phosphonate may then be reacted with the compound of general formula XVI at a temperature of from 20° C. to 45° C. for 1 to 5 hours to form the trans-enone compound of general formula XVIII stereoselectively.

Compounds of general formula XIX may be prepared by reducing to a hydroxy group the oxo group in the side chain attached to the bicyclo-octane ring of a compound of general formula XVIII. The reduction is suitably effected (1) with excess sodium borohydride in an alcohol containing from 1 to 4 carbon atoms, e.g. methanol, at a low temperature, preferably at −30° C. to −60° C., or (2) with zinc borohydride in a suitable inert organic solvent, e.g. 1,2-dimethoxyethane, at a temperature of −10° C. to 10° C. The product thus obtained is a mixture of isomers in which the hydroxy group is in α- or β-configuration. If desired the isomer having the hydroxy group in α-configuration may be separated from the isomer having the hydroxy group in β-configuration by column chromatography on silica gel. The separated isomers may be utilised in the procedures herein described to give prostaglandin analogues of general formula VII in which the hydroxy group in position 15 in α- or β-configuration.

Compounds of general formula XX may be prepared by hydrolysis under alkaline conditions of a compound of general formula XIX, for example by means of anhydrous potassium carbonate in methanol.

Compounds of general formula XXI may be prepared from a compound of general formula XX by reaction with a dihydropyran, dihydrofuran or ethyl vinyl ether in an inert solvent, e.g. methylene chloride, in the presence of a condensing agent, e.g. p-toluenesulphonic acid.

Compounds of general formula XVA may be prepared by reducing to a hydroxy group the oxo group of a compound of general formula XXI with diisobutylaluminium hydride in toluene for about 15 minutes at −60° C.

The dialkylphosphonates of general formula XVII may be prepared by reacting a solution of n-butyllithium in an inert organic solvent, e.g. n-hexane, n-pentane or diethyl ether with a solution of a dialkyl methylphosphonate of the general formula:

   XXII (wherein $R^{10}$ is as hereinbefore defined), e.g. dimethyl methylphosphonate or diethyl methylphosphonate, at a temperature below 50° C., and the adding dropwise to the reaction mixture a solution of a compound of the general formula:

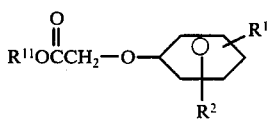

XXIII

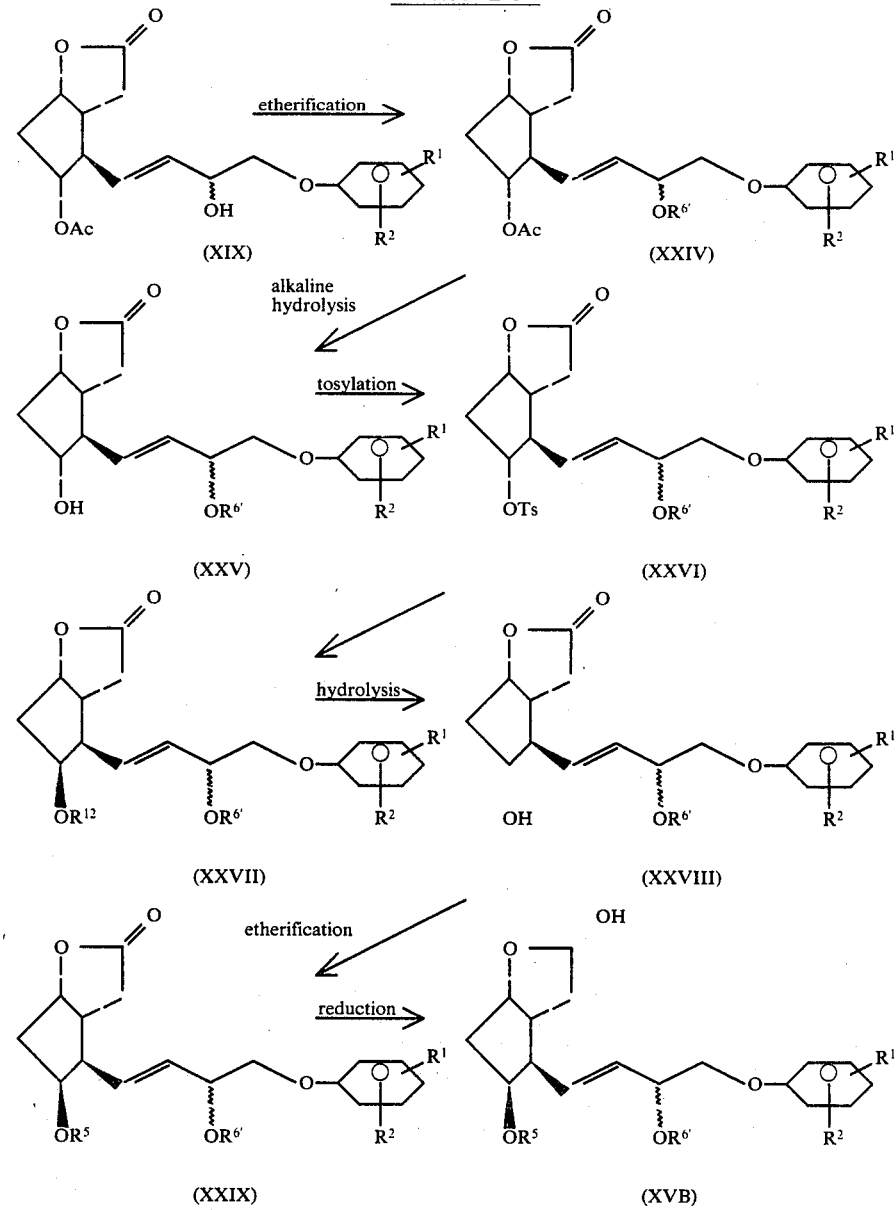

mula XVB], utilizing known procedures may be represented by the series of reactions depicted schematically below in Scheme C (cf. Tetrahedron Letters, 3265–3272, 1972):

(wherein $R^1$ and $R^2$ are as hereinbefore defined, and $R^{11}$ represents a lower alkyl group, preferably containing from 1 to 4 carbon atoms, e.g. methyl or ethyl) in tetrahydrofuran at a temperature below −50° C., stirring the reaction mixture below −50° C. for 1.5 hours and then stirring for 18 hours at 0° C. to give the desired dialkyl phosphonate of general formula XVII.

The compounds of general formula XXIII, e.g. ethyl (3-trifluoromethylphenoxy)acetate, may be prepared by methods known per se.

A method for the preparation of the bicyclooctane compounds of general formula XV, wherein the group $OR^5$ is in β-configuration and the various symbols are as hereinbefore defined [hereafter depicted in general for-wherein $R^{12}$ represents the formyl group or the acetyl group. Ts represents the tosyl group, and the other symbols are as hereinbefore defined. The various reactions may be efected by methods known per se. Compounds of general formula XXVII may be prepared by reacting compounds of general formula XXVI with tetraethylammonium formate or tetraethylammonium acetate.

If desired, a racemic intermediate of general formula XIX may be separated by column chromatography (cf. Tetrahedron Letters, 3269–3272, 1972) into the isomer in which the hydroxy group is in α-configuration and the isomer in which the hydroxy group is in β-configuration. These isomers of general formula XIX may be utilized in the procedures hereinbefore described to give prostaglandin analogues of general formula VII in which the hydroxy group attached to the 15-position carbon atom is in the desired α- or β-configuration.

Compounds of general formula X, wherein $R^3$ represents a hydrogen atom or a straight- or branched-chain alkyl group containing 1 to 4 carbon atoms, $R^5$ represents a 2-tetrahydrofuranyl group, a 1-ethoxyethyl group or a 2-tetrahydropyranyl group unsubstituted or substituted by at least one alkyl group, $R^6$ represents a hydrogen atom and the other symbols are as hereinbefore defined, i.e. compounds of the general formula:

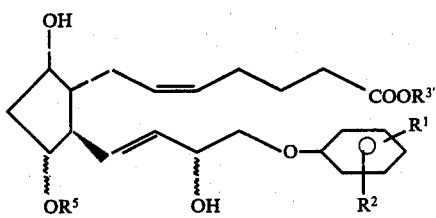

XB (wherein $R^{3'}$ represents a hydrogen atom or a straight- or branched-chain alkyl group containing 1 to 4 carbon atoms and the other symbols are as hereinbefore defined), may be prepared by the hydrolysis under alkaline conditions of a compound of the general formula:

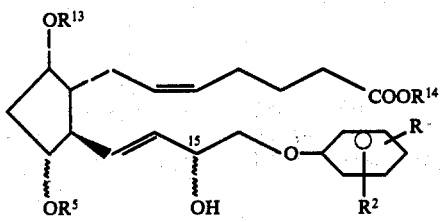

XXX wherein $R^{13}$ represents an alkylcarbonyl group containing from 2 to 5 carbon atoms, $R^{14}$ represents a straight- or branched-chain alkyl group containing from 1 to 4 carbon atoms, and the other symbols are as hereinbefore defined. The hydrolysis under alkaline conditions may be effected with (1) an aqueous solution of an alkali metal, e.g. sodium or potassium, hydroxide or carbonate in the presence of a water miscible solvent, e.g. tetrahydrofuran or an alkanol containing from 1 to 4 carbon atoms, to give a compound of general formula XB wherein $R^{3'}$ represents a hydrogen atom, or (2) with anhydrous potassium carbonate in an anhydrous alkanol containing from 1 to 4 carbon atoms, preferably absolute methanol, to give a compound of general formula XB wherein $R^{3'}$ represents an alkyl group containing from 1 to 4 carbon atoms.

Compounds of general formula XXX may be prepared from a compound of the general formula:

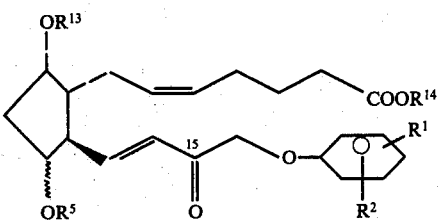

XXXI (wherein the various symbols are as hereinbefore defined) by reduction to convert the 15-oxo group to a hydroxy group. The reduction may be carried out by means heretofore mentioned for the reduction of compounds of general formula XVIII to those of general formula XIX. The product of formula XXX thus obtained is a mixture of isomers in which the hydroxy group at position 15 is in α- or β-configuration. If desired, the isomer having the hydroxy group in α-configuration may be separated from the isomer having the hydroxy group in β-configuration by column chromatography of the mixture on silica gel. The separated isomers may be utilized in the procedures herein described to give prostaglandin analogues of general formula VII in which the hydroxy group in position 15 is in α-or β-configuration.

Compounds of general formula XXXI, wherein the various symbols are as hereinbefore defined, may be obtained by the Wittig reaction of a compound of the general formula:

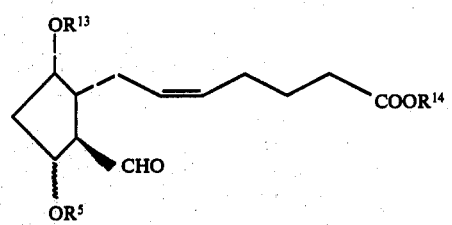

XXXII (wherein the various symbols are as hereinbefore defined), with the sodio derivative of a dialkyl phosphonate of general formula XVII, wherein the various symbols are as hereinbefore defined, preferably using the same reaction conditions as are mentioned heretofore for the reaction of compounds of general formula XVI with those of general formula XVII.

The compounds of general formula XXXII wherein the various symbols are as hereinbefore defined and the group $OR^5$ is in α-configuration [hereinafter depicted in general formula XXXIIA], used as starting materials in the hereinbefore described procedure, may themselves be prepared by methods known per se from compounds of general formula XXXIII by the series of reactions depicted schematically below in Scheme D:

SCHEME D

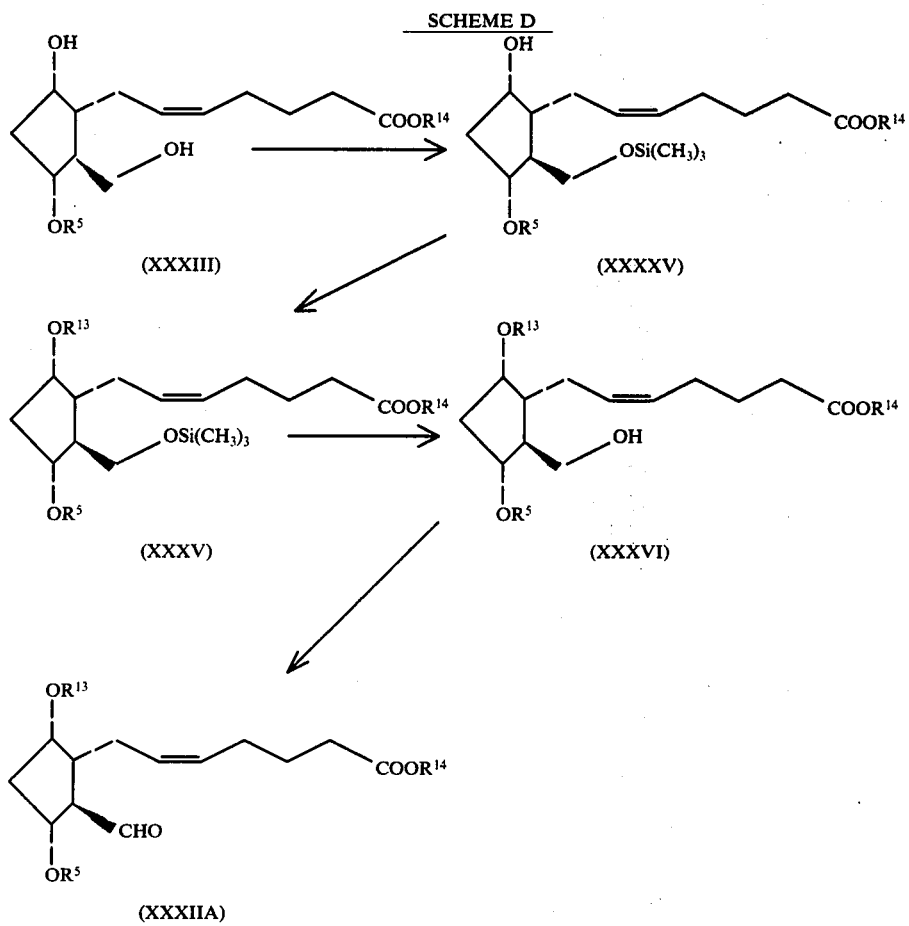

wherein $R^{5'}$, $R^{13}$ and $R^{14}$ are as hereinbefore defined, and preferably $R^{13}$ represents an acetyl group.

Compounds of formula XXXIV may be prepared by reacting a compound of formula XXXIII with trimethylchlorosilane in an inert organic solvent, for example methylene chloride, in the presence of a base, for example pyridine or a tertiary amine, at a low temperature, e.g. at a temperature of −30° C. to 0° C. Compounds of formula XXXV may be prepared by reacting a trimethylsilyl ether of formula XXXIV with the appropriate acyl chloride or acid anhydride in an inert organic solvent, for example methylene chloride, in the presence of a base, for example pyridine or a tertiary amine, at a low temperature, e.g. at a temperature of 0° C. to 30° C. Compounds of formula XXXVI may be prepared by treating a compound of formula XXXV by methods known per se for the removal of the trimethylsilyl group, for example by treatment with an acid; it is preferable not to use a strong acid in order to avoid the risk of the removal of the group $R^5$. The compounds of formula XXXVI may be converted to compounds of formula XXXIIA under mild and neutral conditions, e.g. with chromium trioxide-pyridine complex or Jones' reagent and at a moderately low temperature.

The compounds of general formula XXXIII may themselves be prepared by the method described in Japanese Patent Publication No. 49-102646 from the known compounds of formula XXXVII below [the racemic form of the compound of formula XXXVII is described in J. Amer. Chem. Soc. 91, 5675 (1969) and the natural configuration compound of formula XXXVII is described in J. Amer. Chem. Soc. 92, 397 (1970)] which may be represented by the series of reactions depicted schematically below in Scheme E, wherein the various symbols are as hereinbefore defined.

SCHEME E

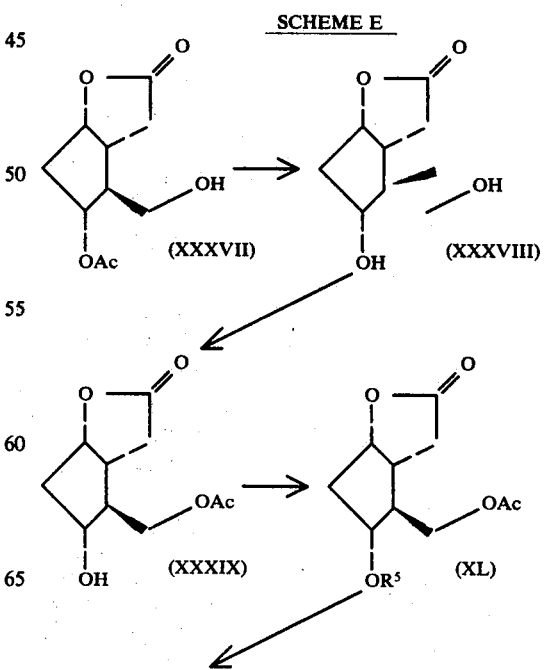

-continued
SCHEME E

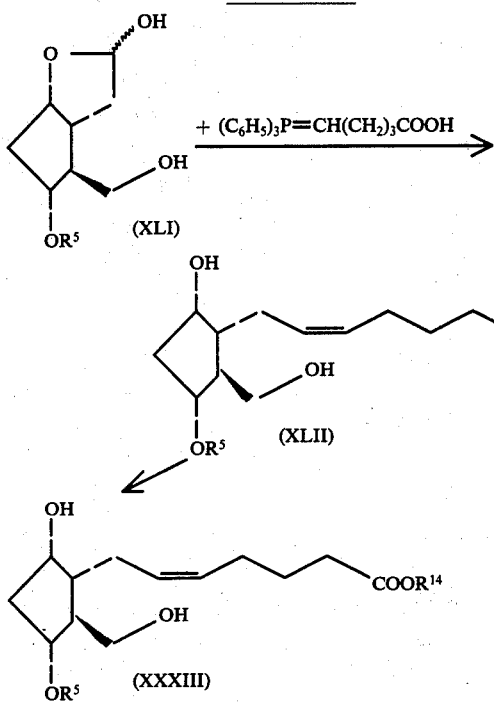

Compounds of formula XXXVIII may be prepared by hydrolysis under alkaline conditions of compounds of formula XXXVII, for example using potassium hydroxide in methanol. Compounds of formula XXXIX may be obtained by the acetylation of compounds of formula XXXVIII under mild conditions and may be converted into compounds of formula XL by reaction with a dihydropyran, dihydrofuran or ethyl vinyl ether in an inert solvent, e.g. methylene chloride, in the presence of a condensing agent, e.g. p-toluenesulphonic acid. compounds of formula XLI may be prepared by reducing compounds of formula XL with diisobutylaluminium hydride in toluene for about 15 minutes at −60° C. Dimsyl anion, previously prepared from sodium hydride and dimethyl sulphoxide, is reacted with (4-carboxybutyl)triphenylphosphonium bromide to form (4-carboxybutylidene)triphenylphosphorane. To that compound is added a compound of formula XLI and the mixture in dimethyl sulphoxide is made to react for 2 hours at room temperature to yield a compound of formula XLII. The acids of formula XLII are then esterified to compounds of formula XXXIII using a method heretofore mentioned for the esterification of compounds of formula XA to compounds of formula X wherein $R^3$ represents an alkyl group containing from 1 to 4 carbon atoms.

The compounds of general formula XXXII wherein the various symbols are as hereinbefore defined and the group $OR^5$ is in β-configuration, which may be used as starting materials in the hereinbefore described procedures, may themselves be prepared by the series of reactions depicted in Schemes D and E but replacing the compounds of formula XXXVII by compounds of the formula:

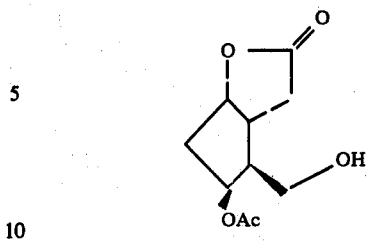

wherein Ac is as hereinbefore defined.

A method for the preparation of the bicyclooctane starting materials of formula XLIII, wherein Ac is as hereinbefore defined, utlizing known procedures may be represented by the series of reactions depicted schematically below in Scheme F (cf. E. J. Corey and Shiro Terashima, Tetrahedron Letters, No. 2, pp. 111–113, 1972):

SCHEME F

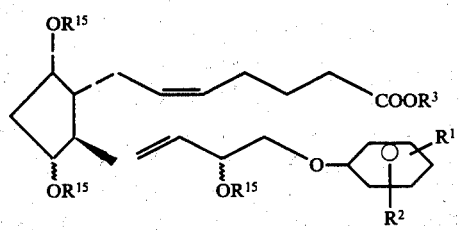

wherein Ac and Ts are as hereinbefore defined. The various reactions depicted above in Scheme F may be effected by methods known per se. Compounds of formula XLVI may be prepared by reacting compounds of formula XLV with tetraethylammonium acetate.

If desired, compounds of general formula VII, wherein A represents a grouping of formula VIIIA, B represents an oxygen atom, R represents a group —COOR³ in which R³ is as hereinbefore defined, and the other symbols are as hereinbefore defined (cf. formula VIIC), may be prepared by the series of reactions depicted in Scheme A (X→XIII→IXA→VIIC) but replacing the compounds of general formula X by compounds of the general formula:

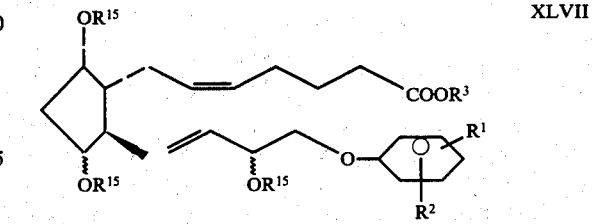

wherein R¹⁵ represents a 2-tetrahydrofuranyl group, a 1-ethoxyethyl group or a 2-tetrahydropyranyl group unsubstituted or substituted by at least one alkyl group, and the other symbols are as hereinbefore defined.

Compounds of general formula XLVII may be prepared from compounds of general formula X by reaction with a dihydropyran, dihydrofuran or ethyl vinyl ether in an inert organic solvent, e.g. methylene chloride, in the presence of a condensing agent, e.g. p-toluenesulphonic acid.

The following reaction Scheme G, wherein the various symbols are as hereinbefore defined, depicts schematically how compounds of general formula XLVII may be obtained starting from compounds of general formulae XV and XXX and utilizing compounds of general formula X as intermediates. Compounds of formula XLVII may be converted to compounds of formula XLVIIA as hereinbefore described for the conversion of compounds of formula X to compounds of formula IXA. The conversion of one compound to another as indicated by arrows in the reaction scheme may be effected by the obvious application of procedures hereinbefore specifically described.

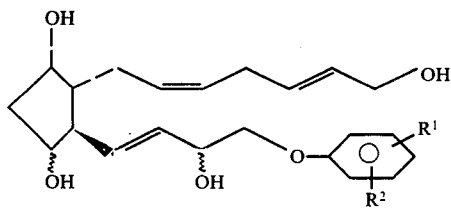

VIIF (wherein R¹ and R² are as hereinbefore defined) may be prepared by the process which comprises reducing a compound of the general formula:

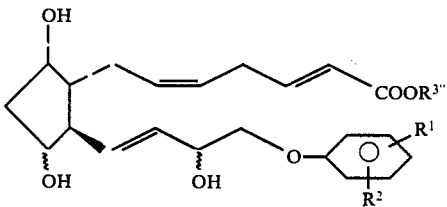

VIIG

SCHEME G

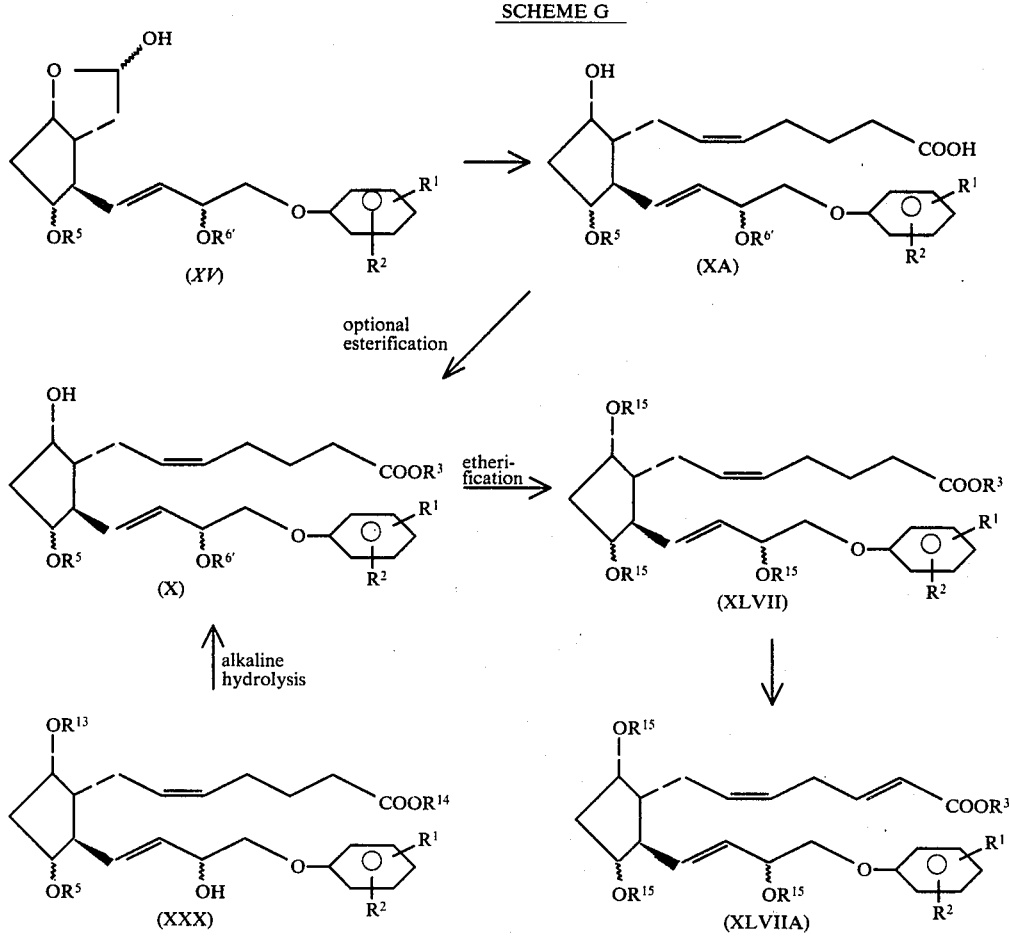

According to a feature of the present invention, the prostaglandin analogues of general formula VII wherein A represents a grouping of formula VIIIA, B represents an oxygen atom, R represents a group —CH₂OR⁴ in which R⁴ represents a hydrogen atom, and the other symbols are as hereinbefore defined, i.e. compounds of the general formula:

(wherein R³" represents a straight- or branched-chain alkyl group containing from 1 to 12 carbon atoms and the other symbols are as hereinbefore defined) to convert the group —COOR³" to a hydroxymethyl group by methods known per se for the conversion of a carboxylic ester group to a hydroxymethyl group. The reduction is preferably effected, for example, by treating the compound of general formula VIIG with 6 to 10 molecular equivalents of diisobutylaluminium hydride in an inert organic solvent e.g. toluene or tetrahydrofuran, at a low temperature, e.g. −78° C.

According to a further feature of the invention compounds of general formula VII wherein A represents a grouping of formula VIIIA, B represents an oxygen atom, R represents a group —CH$_2$OR$^4$ in which R$^4$ represents an alkylcarbonyl group containing from 2 to 5 carbon atoms, and the other symbols are as hereinbefore defined, i.e. compounds of the general formula:

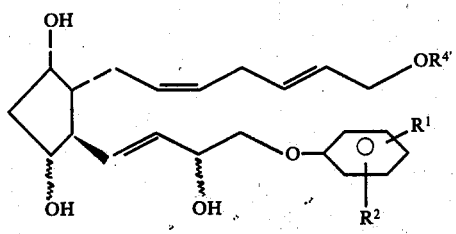

VIIH (wherein R$^4$' represents an alkylcarbonyl group containing from 2 to 5 carbon atoms and the other symbols are as hereinbefore defined) may be prepared frm compounds of general formula VIIF by selective acylation under mild conditions, for example, with an equimolecular amount of an acyl halide in the presence of pyridine in an inert organic solvent, e.g. methylene chloride, at a low temperature, e.g. −20° to −10° C.

According to a further feature of the invention compounds of general formula VII wherein A represents a grouping of formula VIIIA, B represents an oxygen atom, R represents a group CH$_2$OR$^4$ in which R$^4$ is as hereinbefore defined, and the other symbols are as hereinbefore defined, i.e. compounds of the general formula:

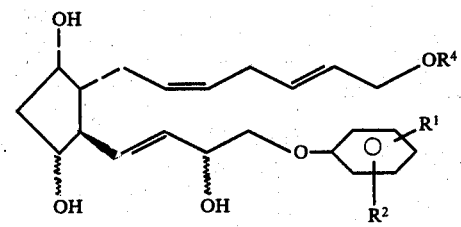

VIIJ (wherein the various symbols are as hereinbefore defined) may be prepared by the process which comprises hydrolysing to hydroxy groups the groups OR$^{15}$ of a compound of the general formula:

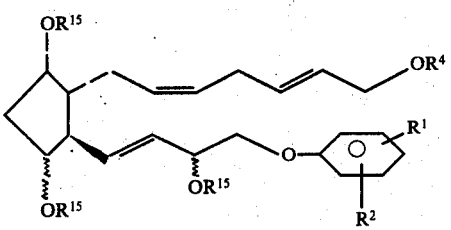

XLVIII wherein the various symbols are as hereinbefore defined.

The OR$^{15}$ groups of the compounds of general formula XLVIII may be converted to hydroxy groups by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60° C. (preferably at a temperature below 45° C.) with an acid mixture, e.g. a mixture of hydrochloric acid with tetrahydrofuran or methanol, or a mixture of acetic acid, water and tetrahydrofuran.

Compounds of general formula XLVIII wherein R$^4$ represents a hydrogen atom, i.e. compounds of the general formula:

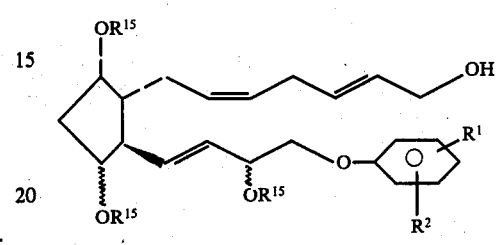

XLVIIIA (wherein the various symbols are as herinbefore defined) may be prepared from a compound of general formula XLVIIA wherein R$^3$ represents a straight- or branched-chain alkyl group containing from 1 to 12 carbon atoms, i.e. a compound of the general formula:

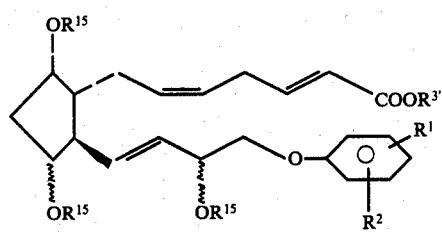

XLVIIB (wherein the various symbols are as hereinbefore defined) by application of the procedure hereinbefore described for the reduction of compounds of general formula VIIG to give compounds of general formula VIIF.

Compounds of general formula XLVIII wherein R$^4$ represents an alkylcarbonyl group containing from 2 to 5 carbon atoms, i.e. compounds of the general formula:

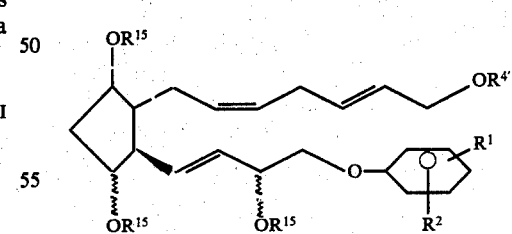

XLVIIIB (wherein the various symbols are as hereinbefore defined) may be prepared from compounds of formula XLVIIIA, by acylation with an appropriate acid anhydride, e.g. acetic anhydride, and pyridine, or with an appropriate acyl halide and a tertiary amine, e.g. triethylamine.

The processes hereinbefore described may be represented by the series of reactions depicted schematically below in Scheme H wherein the various symbols are as hereinbefore defined.

SCHEME H

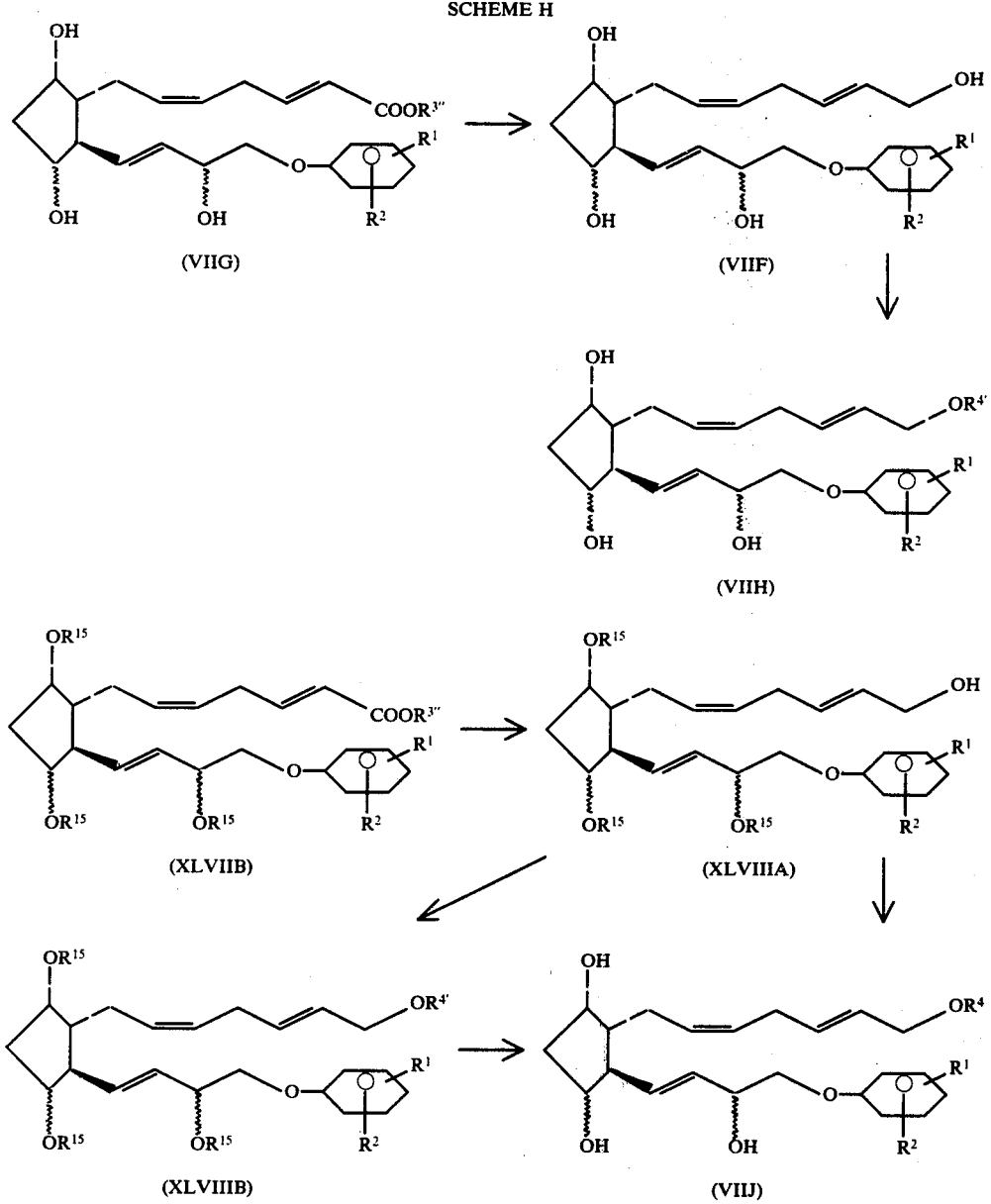

According to a further feature of the present invention compounds of general formula VII wherein A represents a grouping of formula VIIIA, R represents a group —COOR³, in which R³ represents a hydrogen atom or a straight- or branched-chain alkyl group containing from 1 to 4 carbon atoms, and the other symbols are as hereinbefore defined, i.e. compounds of the general formula:

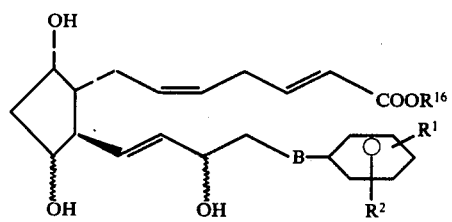

VIIK (wherein $R^{16}$ represents a hydrogen atom or a straight- or branched-chain alkyl group containing from 1 to 4 carbon atoms and the other symbols are as hereinbefore defined) and compounds of the general formula:

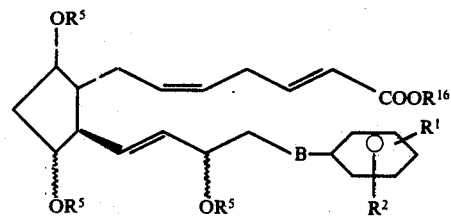

XLIX (wherein the various symbols are as hereinbefore defined) may be prepared by a new synthetic route from the known compounds of formula L [E. J. Corey et al, J. Org. Chem., 37, 2921 (1972)] and from the compound of general formula XLIII which may be represented by the series of reactions depicted schematically below in Scheme I:

SCHEME I
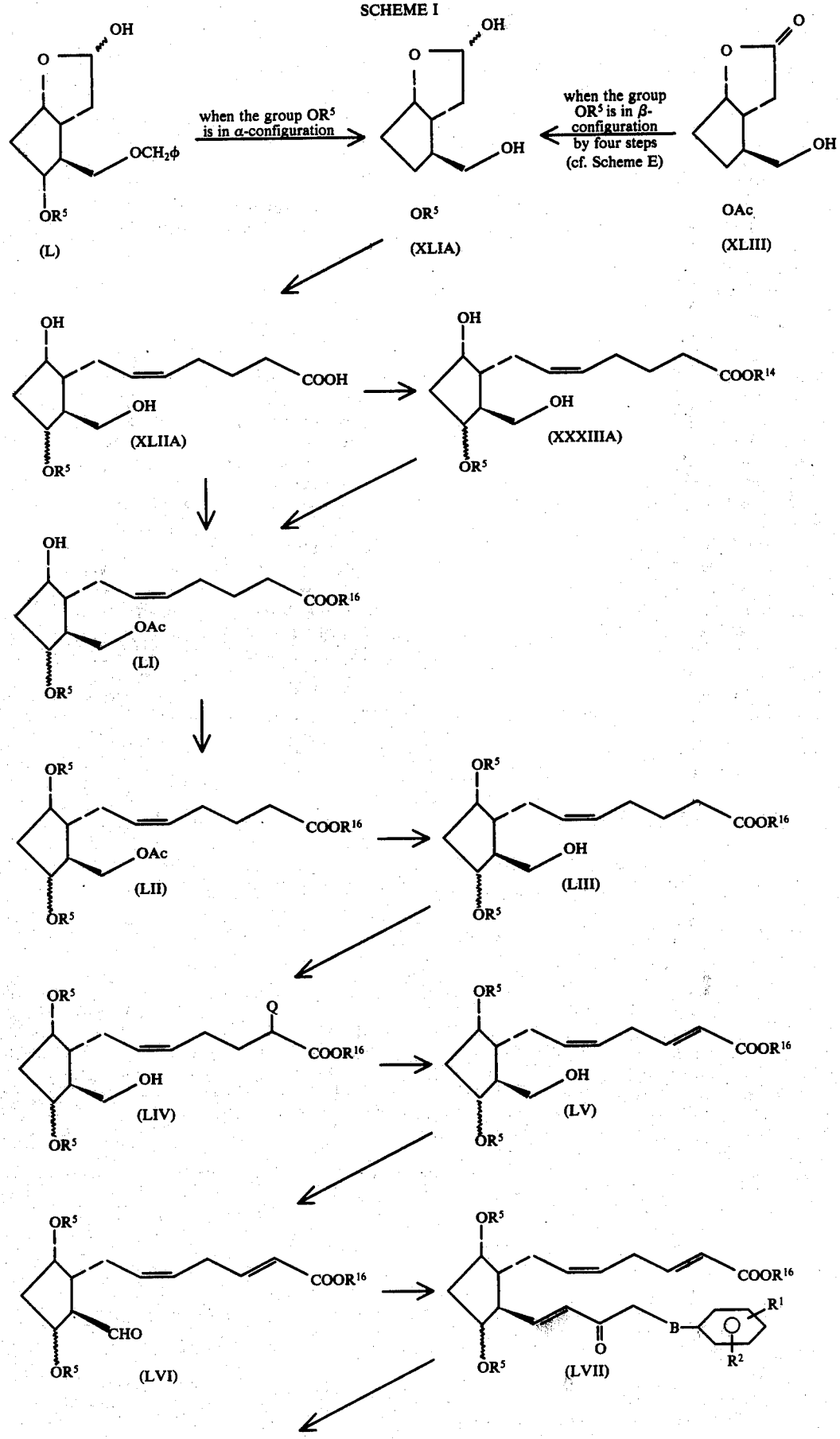

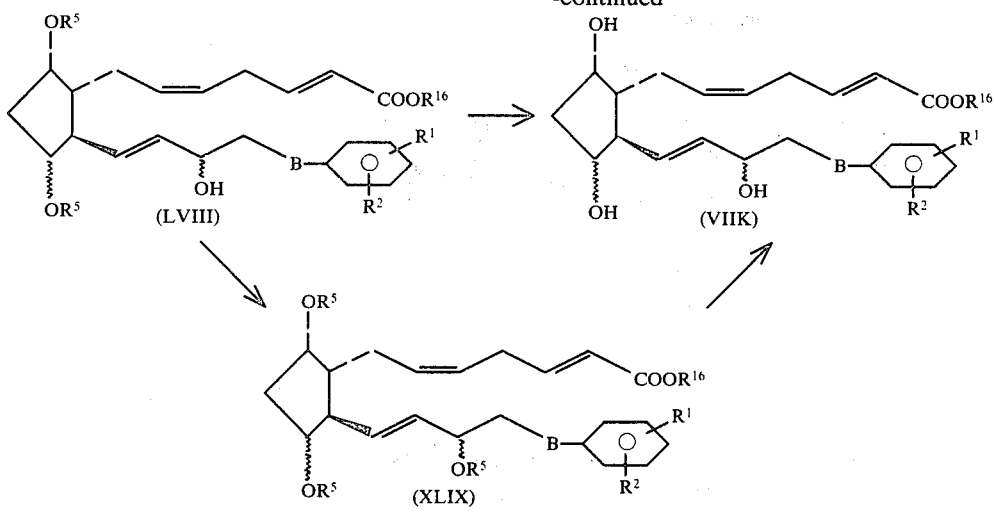

wherein the various symbols are as hereinbefore defined.

Compounds of formula XLIA wherein the group $OR^5$ is in α-configuration may be prepared by hydrogenation of compounds of general formula L in the presence of a hydrogenation catalyst, for example palladium on charcoal, palladium black or platinum dioxide, in an inert organic solvent, for example a lower alkanol, e.g. methanol or ethanol, at laboratory temperature and normal pressure.

Compounds of general formula XLIA wherein the group $OR^5$ is in β-configuration may be prepared from the compound of general formula XLIII by the series of reactions depicted in Scheme E for the preparation of compounds of general formula XLI from the compound of general formula XXXVII, but replacing the compound of formula XXXVII by a compound of general formula XLIII.

The conversion of compounds of general formula XLIA to compounds of general formula XLIIA is effected as hereinbefore described for the conversion of compounds of general formula XLI to XLII.

The acids of formula XLIIA may be esterified to compounds of formula XXXIIIA by known methods as hereinbefore described for the esterification of compounds of formula XLII to compounds of formula XXXIII.

Compounds of formula LI may be prepared by the acetylation of compounds of formula XLIIA or XXXIIIA under mild conditions and may be converted into compounds of formula LII by reaction with a dihydropyran, dihydrofuran or ethyl vinyl ether in an inert organic solvent, e.g. methylene chloride, in the presence of a condensing agent, e.g. p-toluenesulphonic acid.

Compounds of formula LIII may be prepared by hydrolysis under alkaline conditions of compounds of formula LII. The hydrolysis under alkaline conditions may be effected (1) with an aqueous solution of an alkali metal, e.g. sodium or potassium, hydroxide or carbonate in the presence of a water miscible solvent, e.g. tetrahydrofuran or an alkanol containing from 1 to 4 carbon atoms, to give a compound of general formula LIII wherein $R^{16}$ represents a hydrogen atom, or (2) with anhydrous potassium carbonate in an anhydrous alkanol containing from 1 to 4 carbon atoms, preferably absolute methanol, to give a compound of general formula LIII wherein $R^{16}$ represents an alkyl group containing from 1 to 4 carbon atoms.

Compounds of formula LIV may be prepared from compounds of formula LIII by application of the procedures hereinbefore described for the conversion of compounds of formula X to compounds of formula XIII.

Compounds of formula LV may be prepared from compounds of formula LIV by application of the procedures hereinbefore described for the conversion of compounds of formula XIII to compounds of formula IXA.

Compounds of formula LVI may be prepared from compounds of formula LV by oxidation under mild and neutral conditions, e.g. with Collin's reagent (chromium trioxide-pyridine complex) in the presence of an inert organic solvent, e.g. methylene chloride, preferably at a temperature of about 10° C. or with dimethylsulphide-N-chlorosuccinimide at 0° C. to −30° C.

Compounds of formula LVII may be prepared from compounds of formula LVI by reaction with a dialkyl phosphonate of the general formula:

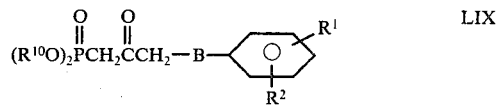

wherein the various symbols are as hereinbefore defined.

The dialkyl phosphonates of general formula LIX may be prepared by the procedure hereinbefore described for the preparation of dialkyl phosphonates of general formula XVII but substituting a compound of the general formula:

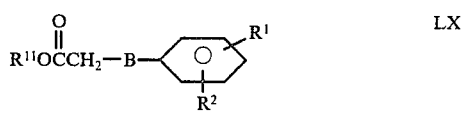

(wherein the various symbols are as hereinbefore defined) for the compound of general formula XXIII.

The compounds of general formula LX may be prepared by method known per se.

The reaction of a compound of general formula LVI with a dialkyl phosphonate of general formula LIX is preferably effected by suspending sodium hydride in an inert organic solvent, e.g. tetrahydrofuran or 1,2-dimethoxyethane, and adding the dialkyl phosphonate of general formula LIX. The resulting sodio derivative of the dialkyl phosphonate may then be reacted with the compound of general formula LVI at a temperature of from 20° C. to 45° C. for one to five hours to form the trans-enone compound of general formula LVII stereoselectively.

Compounds of formula LVIII may be prepared by reducing to a hydroxy group the oxo group in compounds of formula LVII. The reduction is suitably effected with excess sodium borohydride in an alcohol containing from 1 to 4 carbon atoms, e.g. methanol, at a low temperature, preferably at −30° C. to −60° C., or with zinc borohydride in a suitable inert organic solvent, e.g. 1,2-dimethoxyethane, at a temperature of −10° C. to 10° C. The product thus obtained is a mixture of isomers in which the hydroxy group is in α- or β-configuration. If desired the isomer having the hydroxy group in α-configuration may be separated from the isomer having the hydroxy group in β-configuration by column chromatography on silica gel.

Compounds of formula VIIK may be prepared from compounds of formula LVIII or XLIX by application of the procedure hereinbefore described for the hydrolysis of compounds of formula IX to give prostaglandin analogues of formula VIIA.

Compounds of formula XLIX may be prepared from compounds of formula LVIII by application of the procedure hereinbefore described for the conversion of compounds of formula LI to compounds of formula LII.

Compounds of general formula LVIII, wherein B represents a sulphur atom, and the other symbols are as hereinbefore defined, may also be prepared by reacting a compound of the general formula:

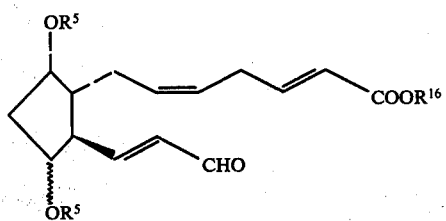

LXI (wherein the various symbols are as hereinbefore defined) with a lithium compound of the general formula:

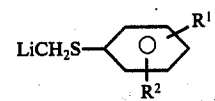

LXII (wherein the various symbols are as hereinbefore defined) in an inert organic solvent, e.g. tetrahydrofuran, at a low temperature, e.g. at −78° C., followed by hydrolysis of the resulting organolithium compound, for example by treatment with an aqueous solution of ammonium chloride or an acid, e.g. oxalic acid or acetic acid, to give a mixture of the 15α- and 15β-hydroxy isomers of compounds of general formula LVIII. If desired, the isomers having the hydroxy group in α- and β-configuration may be separated from the mixture by column chromatography on silica gel.

Compounds of general formula LXI may be prepared by the series of reactions depicted schematically below in Scheme J, wherein $R^{16'}$ represents a straight- or branched-chain alkyl group containing from 1 to 4 carbon atoms, $R^{17}$ represents an alkyl group containing from 1 to 4 carbon atoms and the other symbols are as hereinbefore defined.

SCHEME J

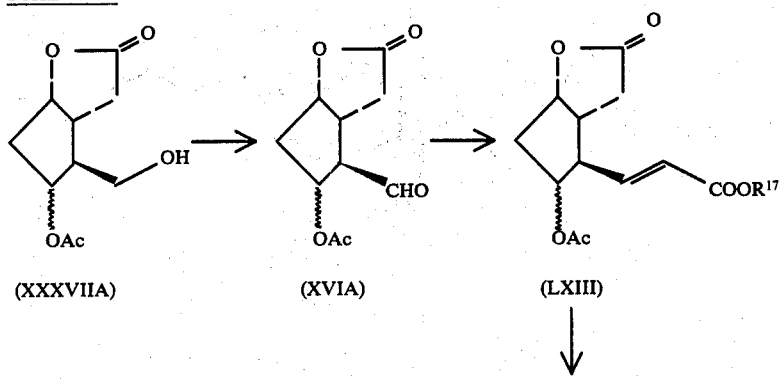

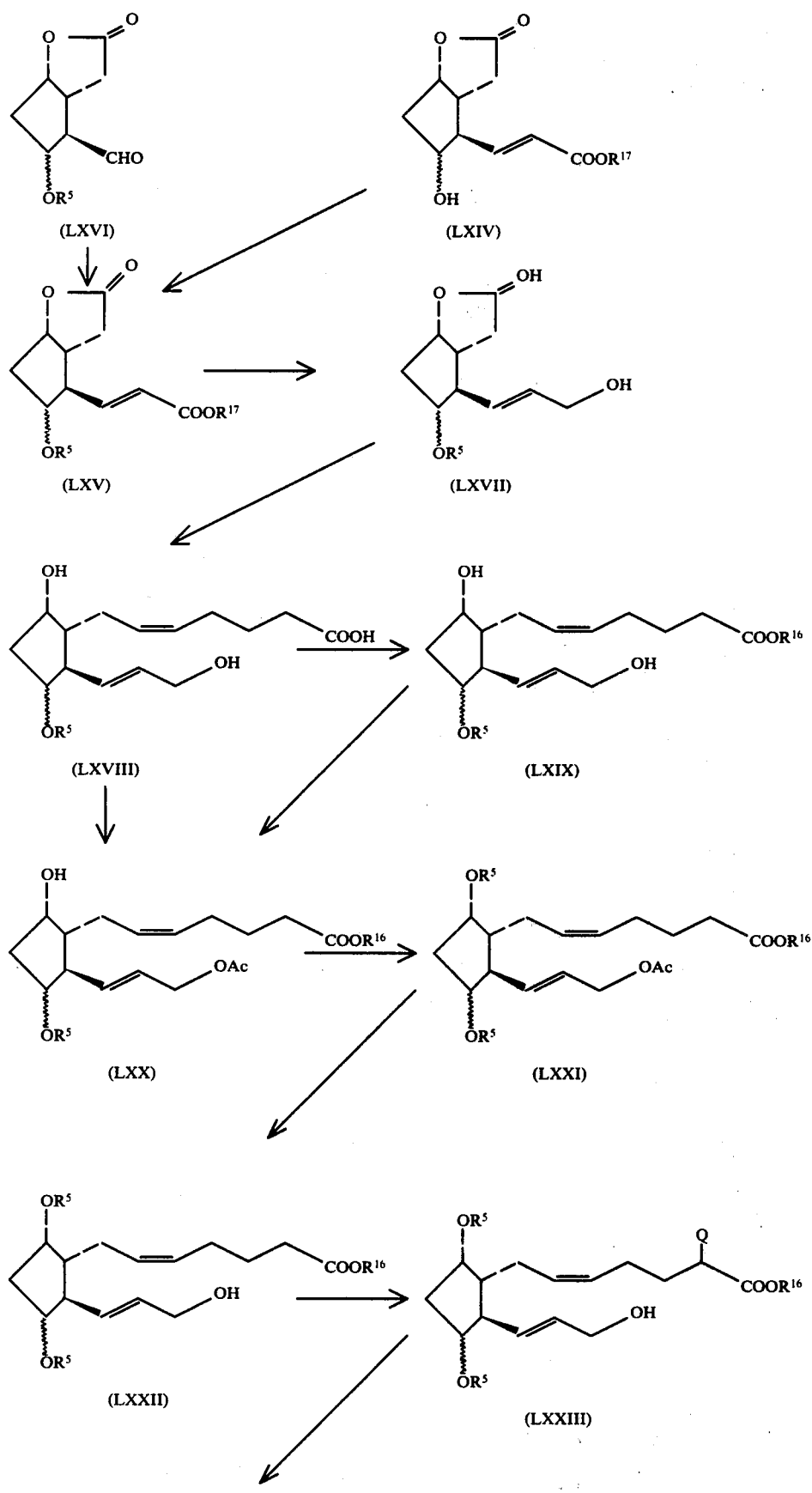

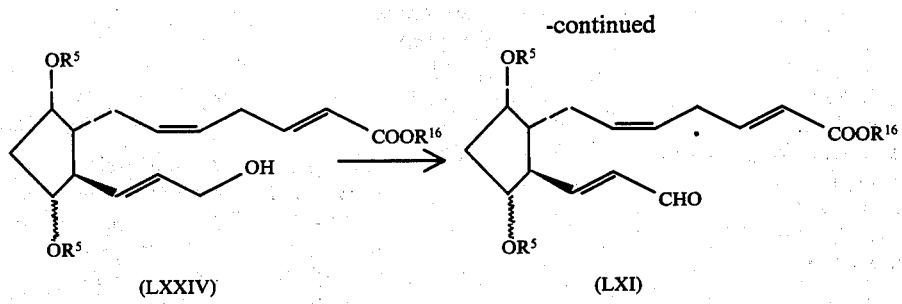

(LXXIV)    (LXI)

The oxidation of compounds of formula XXXVIIA to those of formula XVIA may be carried out by means heretofore mentioned for the conversion of compounds of general formula XXXVI to those of general formula XXXIIA.

Compounds of formula XVIA may be converted stereoselectively to the trans-α,β-unsaturated esters of general formula LXIII by reaction with a sodium derivative of the general formula:

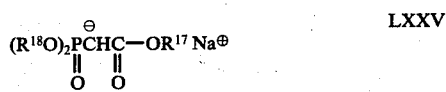

LXXV (wherein $R^{18}$ represents an alkyl group containing from 1 to 4 carbon atoms and $R^{17}$ is as hereinbefore defined) in an inert organic solvent, e.g. tetrahydrofuran or 1,2-dimethoxyethane, at a temperature of 0° to 30° C.

Compounds of general formula LXIII may be converted to compounds of general formula LXIV by deacetylation with potassium carbonate in an absolute alkanol of 1 to 4 carbon atoms, e.g. methanol.

Compounds of general formula LXV may be prepared from compounds of general formula LXIV by means heretofore mentioned for the conversion of compounds of general formula XX to those of general formula XXI.

Compounds of general formula LXV may also be prepared from compounds of general formula LXVI by means heretofore mentioned for the conversion of compounds of formula XVIA to those of general formula LXIII.

Compounds of general formula LXV may be converted to compounds of general formula LXVII by means heretofore mentioned for the conversion of compounds of general formula XXI to those of general formula XVA.

The conversion of compounds of general formula LXVII to those of general formula LXVIII may be carried out by means heretofore mentioned for the conversion of compounds of general formula XV to those of general formula XA.

If desired, compounds of general formula LXVIII may be converted to compounds of general formula LXIX by means heretofore mentioned for the esterification of compounds of general formula XA to those of general formula X wherein $R^3$ represents an alkyl group containing from 1 to 4 carbon atoms.

Compounds of general formula LXX may be prepared by the acetylation of compounds of general formula LXVIII or LXIX under mild conditions, for example with acetyl chloride in the presence of pyridine, and may be converted to compounds of general formula LXXI by reaction with a dihydropyran, dihydrofuran or ethyl vinyl ether in an inert organic solvent, e.g. methylene chloride, in the presence of a condensing agent, e.g. p-toluenesulphonic acid.

The conversion of compounds of general formula LXXI to those of general formula LXXII may be carried out by means heretofore mentioned for the conversion of compounds of general formula XXX to those of general formula XB.

The conversion of compounds of general formula LXXII to those of general formula LXXIV via compounds of general formula LXXIII may be carried out by means heretofore mentioned for the conversion of compounds of general formula X to those of general formula IXA via compounds of general formula XIII.

Compounds of general formula LXXIV may be converted to compounds of general formula LXI by oxidation with manganese dioxide in an inert organic solvent, e.g. acetone or methylene chloride, at laboratory temperature.

The lithium compound of general formula LXII may be prepared from a compound of the general formula:

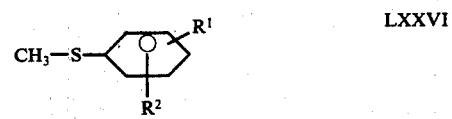

LXXVI (wherein the various symbols are as hereinbefore defined) by reaction with a compound of general formula XI or an alkyllithium compound, e.g. n-butyllithium, in an inert organic solvent, e.g. tetrahydrofuran, at a low temperature, preferably below −20° C.

Compounds of general formula LXXVI may be prepared by methods known per se.

According to a further feature of the present invention compounds of general formula VII, wherein A represents a grouping of formula VIIIA, R represents a group $CH_2OR^4$, in which $R^4$ represents a hydrogen atom or $R^4$ represents an alkylcarbonyl group containing from 2 to 5 carbon atoms, and the other symbols are as hereinbefore defined, i.e. compounds of the general formulae:

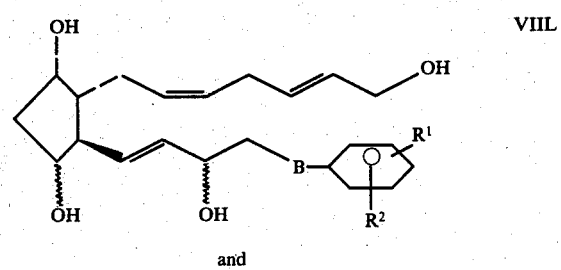

VIIL and

-continued
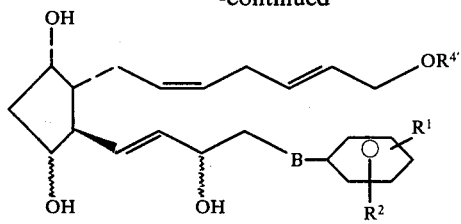
VIIM
(wherein the various symbols are as hereinbefore defined) may be prepared by the series of reactions hereinbefore depicted in Scheme H, replacing the compounds of general formulae VIIG and XLVIIB used as starting materials by compounds of general formulae VIIN and LXIXA, as depicted below in Scheme K:
SCHEME K
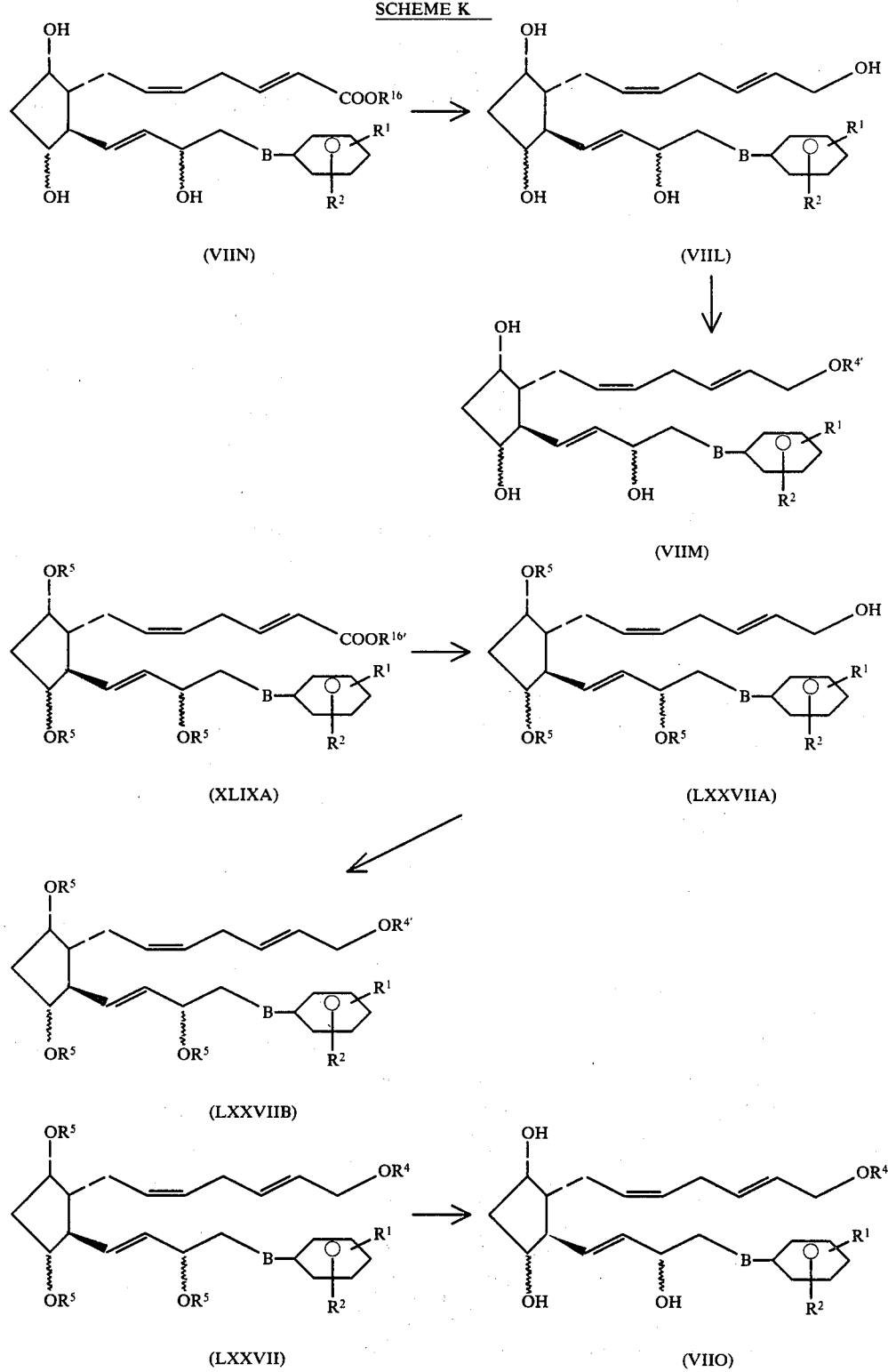

wherein the various symbols are as hereinbefore defined.

The series of reactions VIIN→VIIM (via VIIL) and XLIXA→VIIO (via LXXVIIA and LXXVIIB) depicted in Scheme K may be effected as hereinbefore described for the series of reactions VIIG→VIIH (via VIIF) and XLVIIB→VIIJ (via XLVIIIA and XLVIIIB) respectively, in Scheme H.

According to a feature of the present invention compounds of general formula VII, wherein A represents a grouping of formula VIIIB, B represents an oxygen atom, R represents a group —CH$_2$OR$^4$, in which R$^4$ is as hereinbefore defined, and the other symbols are as hereinbefore defined, i.e. compounds of the general formula:

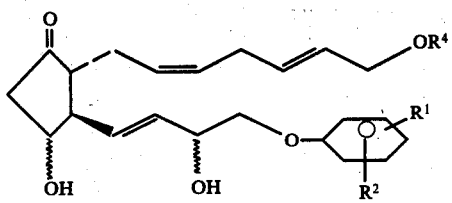

VIIP (wherein the various symbols are as hereinbefore defined) may be prepared from compounds of general formula IX, wherein Z represents

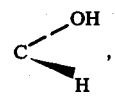

R$^3$ represents a straight- or branched-chain alkyl group containing from 1 to 12 carbon atoms, R$^6$ represents a 2-tetrahydrofuranyl group, a 1-ethoxyethyl group, or a 2-tetrahydropyranyl group unsubstituted or substituted by at least one alkyl group, and the other symbols are as hereinbefore defined, i.e. compounds of the general formula:

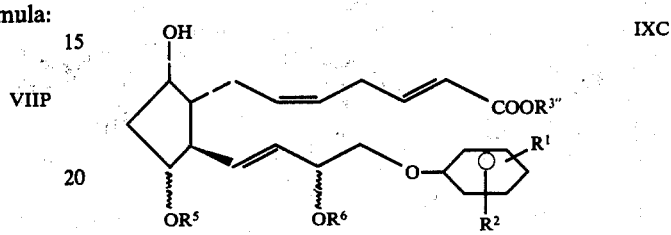

IXC (wherein the various symbols are as hereinbefore defined) by the series of reactions depicted schematically below in Scheme L, wherein R$^{19}$ represents the trityl group, i.e. —C$\phi_3$, wherein $\phi$ represents the phenyl group, and the other symbols are as hereinbefore defined.

SCHEME L

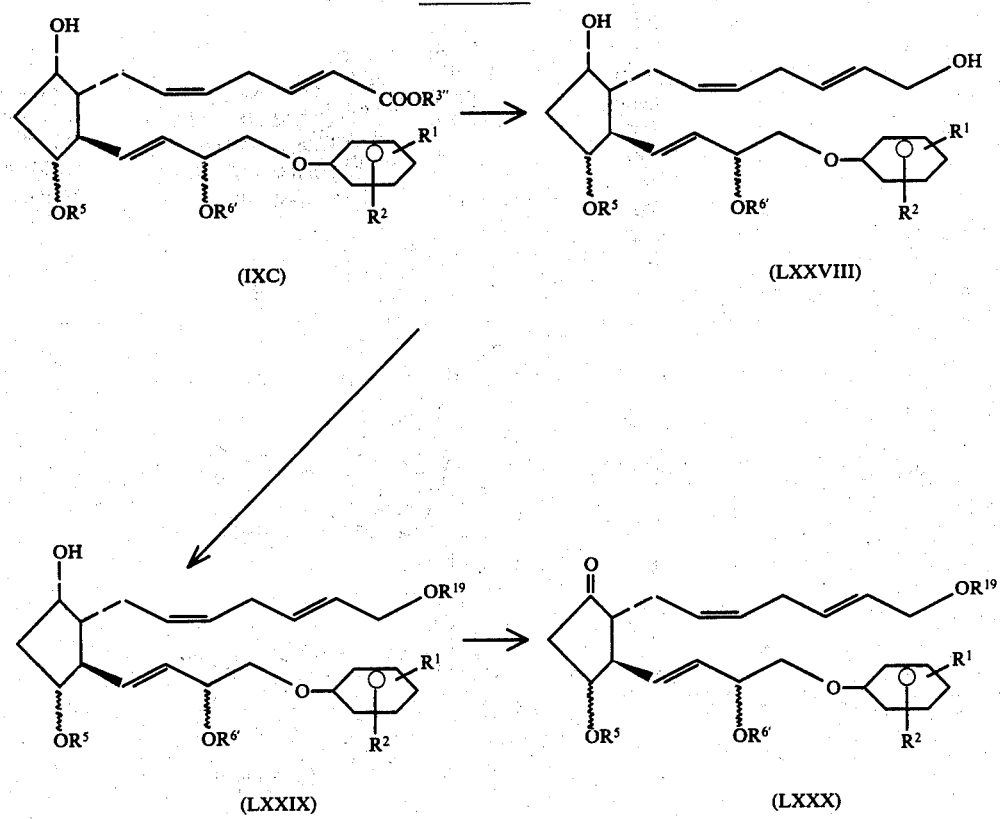

SCHEME L

-continued

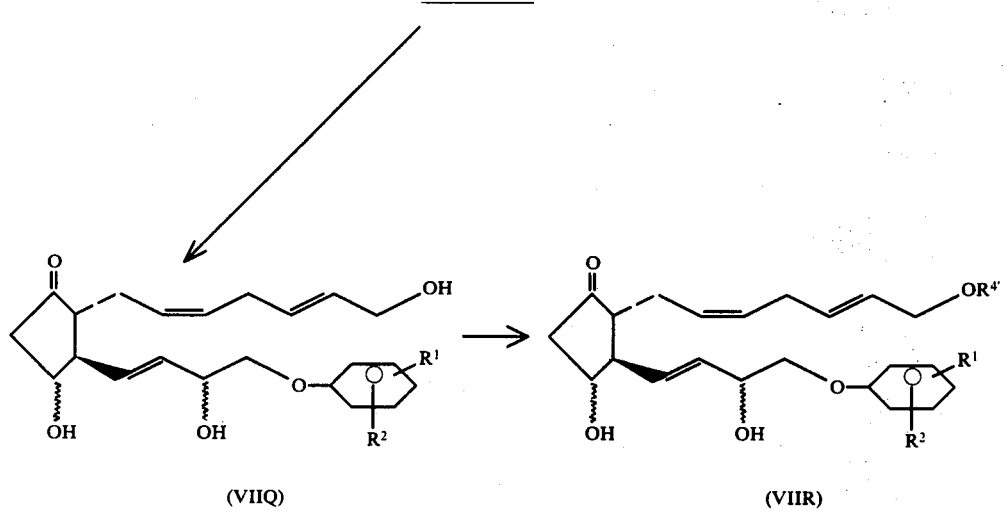

(VIIQ)   (VIIR)

The conversion of compounds of general formula IXC to those of general formula LXXVIII may be carried out by means heretofore mentioned for the conversion of compounds of general formula VIIG to those of general formula VIIF. Compounds of general formula LXXVIII may be converted to compounds of general formula LXXIX by reaction with trityl chloride in pyridine or in methylene chloride in the presence of a base, e.g. pyridine or a tertiary amine, at a temperature ranging from ambient to 70° C.

The series of reactions LXXIX→VIIQ (via LXXX) may be effected as hereinbefore described for the series of reactions IXA→VIID (via IXB). The group $OR^{19}$ is converted to a hydroxy group under the conditions used to hydrolyse to hydroxy groups the groups $OR^5$ and $OR^{6'}$. The conversion of compounds of general formula VIIQ to VIIR may be carried out by means heretofore mentioned for the conversion of compounds of general formula VIIL to VIIM.

According to a further feature of the present invention compounds of general formula VII, wherein A represents a grouping of formula VIIIB, B represents a sulphur atom, R represents a group $COOR^3$, in which $R^3$ is as hereinbefore defined, and the other symbols are as hereinbefore defined, i.e. compounds of the general formula:

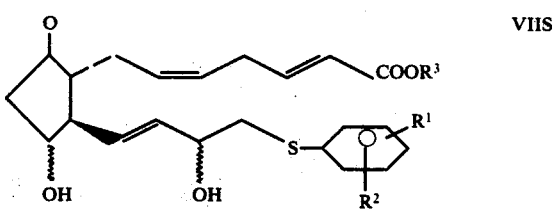

VIIS (wherein the various symbols are as hereinbefore defined) may be prepared from compounds of general formula LXVIII by the series of reactions depicted schematically below in Scheme M, wherein the various symbols are as hereinbefore defined.

SCHEME M

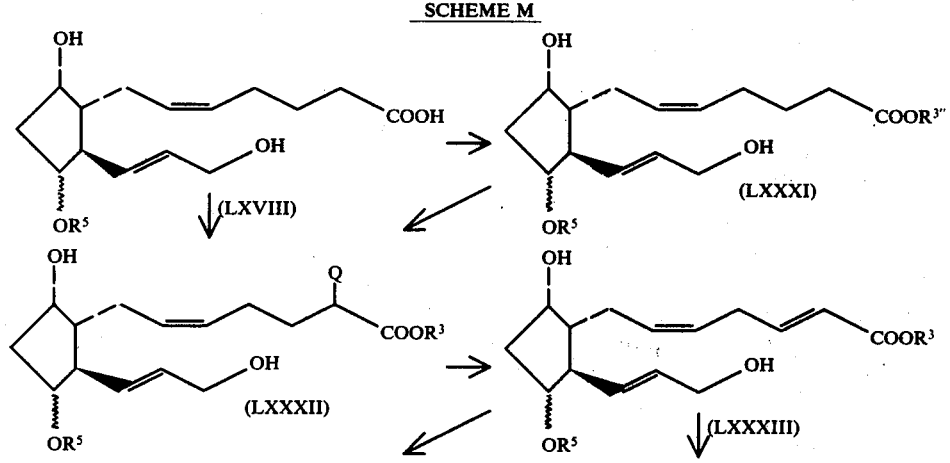

-continued
SCHEME M

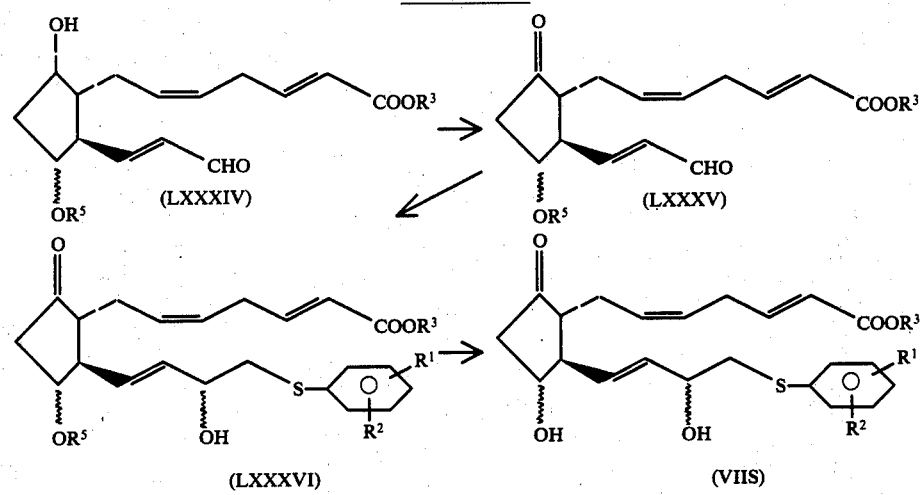

The esterification of compounds of general formula LXVIII to those of general formula LXXXI may be carried out by means heretofore mentioned for the conversion of compounds of general formula XA to those of general formula X, wherein $R^3$ represents an alkyl group containing from 1 to 12 carbon atoms.

The series of reactions LXVIII or LXXXI→LXXXIII (via LXXXII) may be effected as hereinbefore described for the series of reactions X→IXA (via XIII).

Compounds of general formula LXXXIII may be converted to compounds of general formula LXXXIV by selective oxidation with manganese dioxide in an inert organic solvent, e.g. acetone or methylene chloride, at room temperature, which oxidizes an allylic alcohol group to a formyl group.

Compounds of general formula LXXXIV may be converted to compounds of general formula LXXXV by oxidation under mild and neutral conditions, e.g. with Collins' or Jones' reagent at a moderately low temperature, e.g. below room temperature.

Compounds of general formula LXXXV can also be prepared directly from compounds of general formula LXXXIII by oxidation under mild and neutral conditions, e.g. with Collins' or Jones' reagent at a moderately low temperature, e.g. below room temperature.

The series of reactions LXXXV→VIIS (via LXXXVI) may be carried out by means hereinbefore described for the series of reactions LXI→LVIII→•

VIIK, using a compound of general formula LXII wherein $\beta$ represents a sulphur atom and $R^1$ and $R^2$ are as hereinbefore defined.

Compounds of general formula VII, wherein A represents a grouping of formula VIIIB, B represents a sulphur atom, R represents a group $CH_2OR^4$, in which $R^4$ is as hereinbefore defined, and the other symbols are as hereinbefore defined, i.e. compounds of the general formula:

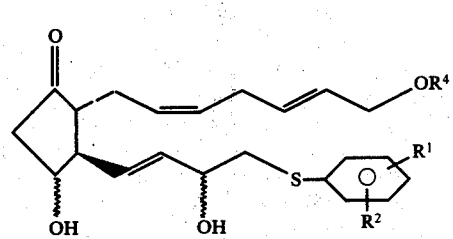

VIIT (wherein the various symbols are as hereinbefore defined) may be prepared from compounds of general formula LXXXIV, wherein $R^3$ represents an alkyl group containing from 1 to 12 carbon atoms, by the series of reactions depicted schematically below in Scheme N, wherein the various symbols are as hereinbefore defined.

SCHEME N

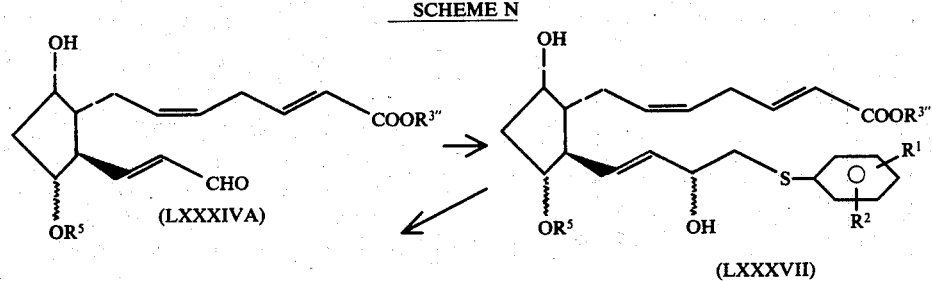

SCHEME N -continued

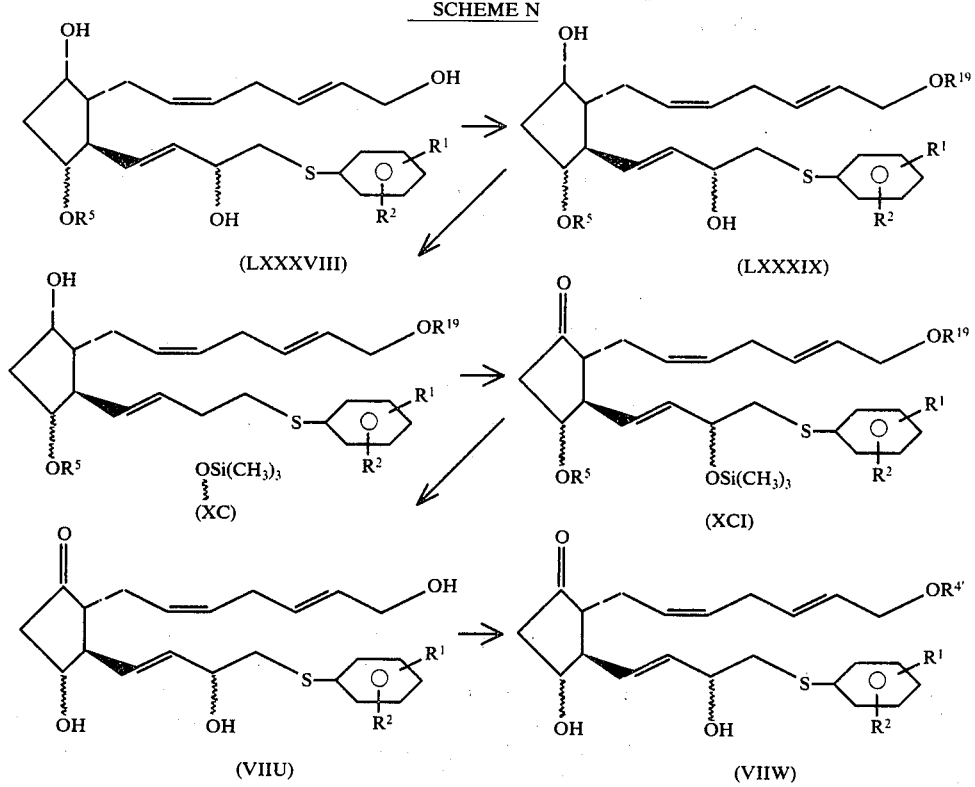

Compounds of general formula LXXXIVA may be converted to those of general formula LXXXVII by means heretofore mentioned for the conversion of compounds of general formula LXI to those of general formula LVIII, using a compound of general formula LXII wherein B represents a sulphur atom and $R^1$ and $R^2$ are as hereinbefore defined.

Compounds of general formula LXXXVII may be converted to those of general formula LXXXVIII by means heretofore mentioned for the conversion of compounds of general formula VIIG to those of general formula VIIF.

Compounds of general formula LXXXVIII may be converted to those of general formula LXXXIX by means heretofore mentioned for the conversion of compounds of general formula LXXVIII to those of general formula LXXIX.

Compounds of general formula LXXXIX may be converted to compounds of general formula XC by reaction with a suitable trimethylsilylating reagent, e.g. N-trimethylsilyldiethylamine or N,O-bis(trimethylsilyl)acetamide, in acetone, preferably at room temperature.

The series of reactions XC→VIIU (via XCI) may be effected as hereinbefore described for the series of reactions IXA→VIID (via IXB). The group $OR^{19}$ and the trimethylsilyloxy group in the compounds of general formula SCI are converted to hydroxy groups under the conditions used to hydrolyse to a hydroxy group the group $OR^5$.

Compounds of general formula VIIU may be converted to those of general formula VIIW by means heretofore mentioned for the conversion of compounds of general formula VIIL to VIIM.

Compounds of general formula VIIP, VIIS, VIIT, VIIU, VIIW, LXXX, LXXXVI, or SCI may be converted to the corresponding PGA compounds of general formula VII, wherein A represents a grouping of formula IV, by means heretofore mentioned for the conversion of compounds of general formula VIID or IXB to those of general formula VIIE.

According to a further feature of the present invention, the compounds of general formula VII, wherein A, B, $R^1$ and $R^2$ are as hereinbefore defined and R represents a group —$COOR^3$, in which $R^3$ represents a straight- or branched-chain alkyl group containing from 1 to 12 carbon atoms, are prepared by esterification of the corresponding acids of formula VII wherein $R^3$ represents a hydrogen atom by methods known per se, for example by reaction with (i) the appropriate diazoalkane in an inert organic solvent, e.g. diethyl ether, at a temperature of from $-10°$ C. to $25°$ C. and preferably $0°$ C., (ii) the appropriate alcohol in the presence of dicyclohexylcarbodiimide as condensing agent, or (iii) the appropriate alcohol following formation of a mixed anhydride by adding a tertiary amine and pivaloyl halide or an arylsulphonyl or alkylsulphonyl halide (cf. our British Pat. Nos. 1362956 and 1364125).

Compounds of general formula VII wherein R represents a group $COOR^3$, in which $R^3$ represents a hydrogen atom may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of general formula VII wherein R represents a group COOR$^3$, in which R$^3$ represents a hydrogen atom by, for example, reaction of stoichiometric quantities of an acid of general formula VII and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of general formula VII may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the prostaglandin analogues.

The present invention also includes, as further features, the hitherto unknown compounds of general formulae IX, XLVIIA, XLVIII, XLIX, LVIII, LXXVII, LXXXVI, LXXX and XCI and the methods heretofore described for their preparation.

The prostaglandin analogues of general formula VII and their cyclodextrin clathrates and, when R represents a group COOR$^3$ in which R$^3$ represents a hydrogen atom, non-toxic salts thereof possess the valuable pharmacological properties typical of the prostaglandins in a selective fashion, in particular stimulatory activity on uterine contraction and abortifacient, luteolytic and antinidatory activity and are useful in the termination of pregnancy and induction of labour in pregnant female mammals, in the treatment of impaired fertility and in the control of oestrus, contraception and menstrual regulation in female mammals. For example, in standard laboratory tests, (i) 16-(3-trifluoromethylphenoxy)-17,18,19,20-tetranor-trans-$\Delta^2$-PGF$_{2\alpha}$ methyl ester, 16-phenoxy-17,18,19,20-tetranor-trans-$\Delta^2$-PGF$_{2\alpha}$ methyl ester, 16-(3-chlorophenoxy)-17,18,19,20-tetranor-trans-$\Delta^2$-PGF$_{2\alpha}$ methyl ester, 16-(3-chlorophenoxy)-17,18,19,20-tetranor-trans-$\Delta^2$-PGF$_{2\alpha}$ alcohol, 16-phenoxy-17,18,19,20-tetranor-trans-$\Delta^2$-PGF$_{2\alpha}$ alcohol and 16-phenylthio-17,18,19,20-tetranor-trans-$\Delta^2$-PGF$_{2\alpha}$ methyl ester inhibit implantation in pregnant female rats when administered subcutaneously on the 3rd, 4th and 5th days of pregnancy at the daily doses of 50,10, 20,100, 50 and 200 $\mu$g./kg. animal body weight, respectively; (ii) 16-(3-trifluoromethylphenoxy)-17,18,19,20-tetranor-trans-$\Delta^2$-PGF$_{2\alpha}$ methyl ester, 16-phenoxy-17,18,19,20-tetranor-trans-$\Delta^2$-PGF$_{2\alpha}$ methyl ester and 16-(3-chlorophenoxy)-17,18,19,20-tetranor-trans-$\Delta^2$-PGF$_{2\alpha}$ methyl ester produce an abortifacient effect in pregnant female rats when administered intraperitoneally on the 17th day of pregnancy at the daily doses of 10, 2 and 5.0 $\mu$g./kg. animal body weight, respectively; (iii) in tests for luteolytic effect [Rats are hysterectomized on the 5th day of gestation (day 0-sperm confirmation). The compound under test is administered subcutaneously from the 2nd day following the hysterectomy. The luteal period is observed by the vaginal smear test. The compound is administered each day until the first oestrus begins. The compound is regarded as effective if the first oestrus begins within 5 days.], 16-(3-trifluoromethylphenoxy)-17,18,19,20-tetranor-trans-$\Delta^2$-PGF$_{2\alpha}$ methyl ester, 16-phenoxy-17,18,19,20-tetranor-trans-$\Delta^2$-PGF$_{2\alpha}$ methyl ester and 16-(3-chlorophenoxy)-17,18,19,20-tetranor-trans-$\Delta^2$-PGF$_{2\alpha}$ methyl ester produce 60% luteolytic effect at the daily doses of 0.2, 0.1 and 0.5 $\mu$g./kg. animal body weight, respectively, and (iv) 16-(3-trifluoromethylphenoxy)-17,18,19,20-tetranor-trans-$\Delta^2$-PGF$_{2\alpha}$ methyl ester, 16-phenoxy-17,18,19,20-tetranor-trans-$\Delta^2$-PGF$_{2\alpha}$ methyl ester, 16-(3-chlorophenoxy)-17,18,19,20-tetranor-trans-$\Delta^2$-PGF$_{2\alpha}$ methyl ester and 16-(3-chlorophenoxy)-17,18,19,20-tetranor-trans-$\Delta^2$-PGF$_{2\alpha}$ alcohol stimulate uterine contraction in the pregnant female rat when administered intravenously on the 20th day of gestation at the doses of 50, 2 - 5, 2 and 5 - 10 $\mu$g./kg. animal body weight, respectively. The prostaglandin compounds of the present invention and their cyclodextrin clathrates and non-toxic salts possess relatively low potencies in inducing diarrhoea in comparison with their potencies in respect of the valuable properties hereinbefore described. For example the doses by oral administration of 16-(3-trifluoromethylphenoxy)-17,18,19,20-tetranor-trans-$\Delta^2$-PGF$_{2\alpha}$ methyl ester, 16-phenoxy-17,18,19,20-tetranor-trans-$\Delta^2$-PGF$_{2\alpha}$ methyl ester, 16-(3-chlorophenoxy)-17,18,19,20-tetranor-trans-$\Delta^2$-PGF$_{2\alpha}$ methyl ester and 16-(3-chlorophenoxy)-17,18,19,20-tetranor-trans-$\Delta^2$-PGF$_{2\alpha}$ alcohol required to produce diarrhoea in 50% of mice so treated are 1 - 5, 0.47, 0.62 and 0.74 mg./kg. animal body weight, respectively.

The following Reference Examples and Examples illustrate the preparation of new prostaglandin analogues of the present invention. In them 'IR', 'NMR' and 'TLC' represent respectively 'Infrared absorption spectrum' 'Nuclear magnetic resonance spectrum' and 'Thin layer chromatography'. Where solvent ratios are specified in chromatographic separations, the ratios are by volume.

REFERENCE EXAMPLE 1

Methyl 9$\alpha$,15$\alpha$-dihydroxy-11$\alpha$-(2-tetrahydropyranyloxy)-16-(3-trifluoromethylphenoxy)-17,18,19,20-tetranorprosta-cis-5,trans-13-dienoate 481 mg. of methyl 9$\alpha$-acetoxy-11$\alpha$-(2-tetrahydropyranyloxy)-15$\alpha$-hydroxy-16-(3-trifluoromethylphenoxy)-17,18,19,20-tetranorprosta-cis-5,trans-13-dienoate (prepared as described hereafter) were dissolved in 3.18 ml. of methanol and stirred with 137 mg. of potassium carbonate at 40° C. for 2.5 hours. The reaction mixture was then neutralized with 1.69 ml. of 1N hydrochloric acid and diluted with ethyl acetate. The solution was washed with an aqueous solution of sodium bicarbonate and an aqueous solution of sodium chloride, dried over magnesium sulphate and concentrated under reduced pressure to give 447 mg. of the title compound having the following physical characteristics: TLC (developing solvent benzene — ethyl acetate = 2:1); Rf = 0.2; IR (liquid film): ν; 3400, 2940, 1740, 1600, 1500, 980 cm$^{-1}$; NMR (CCl$_4$ solution): δ; 7.7–6.9 (4H, m), 6.1–5.55 (2H, m), 5.55–5.0 (2H, m).

Methyl 9α-acetoxy-11α-(2-tetrahydropyranyloxy)-15α-hydroxy-16-(3-trifluoromethylphenoxy)-17,18,19,20-tetranorprosta-cis-5,trans-13-dienoate, used as a starting material in the above procedure, was prepared as follows:

24 g. of 3-trifluoromethylphenol, 19.2 g. of ethyl chloroacetate, 22.5 g. of sodium iodide and 20.8 g. of potassim carbonate were added to 75 ml. of dry acetone and the reaction mixture was refluxed for 16 hours. Then the reaction mixture was poured into a cold aqueous hydrochloric acid solution and extracted with ethyl acetate. The organic extracts were washed with water and an aqueous sodium chloride solution, dried over magnesium sulphate and concentrated under reduced pressure. The residue was purified by distillation in vacuo to give 29.5 g. of ethyl (3-trifluoromethylphenoxy)acetate having the following physical characteristics: boiling point: 122° to 125° C./19 mm.Hg; IR (liquid film): ν; 1750, 1590, 1330, 1130 cm$^{-1}$; NMR (CCl$_4$ solution): δ; 7.65–6.90 (4H, m), 4.64 (2H, s), 4.25 (2H, q), 1.25 (3H, t).

33.0 g. of dimethyl methylphosphonate were dissolved in 260 ml. of anhydrous tetrahydrofuran, to which 131 ml. of a solution of 2N n-butyllithium in n-hexane were added dropwise whilst maintaining the temperature from −60° to −55° C. After stirring for 30 minutes, 29.5 g. of ethyl (3-trifluoromethylphenoxy)acetate (obtained as described above) in 100 ml. of anhydrous tetrahydrofuran were added to the solution. The mixture was stirred at the same temperature for 1.5 hours and then at 0° C. for 18 hours. The reaction mixture was neutralized with acetic acid and concentrated under reduced pressure. The residue was dissolved in a small amount of water and extracted with diethyl ether. The ethereal extracts were washed with an aqueous sodium chloride solution, dried over magnesium sulphate and concentrated under reduced pressure. The residue was distilled at 160° C. under a pressure of 0.7 mm.Hg to remove the non-reacted impurities. The resulting residue was purified by column chromatography on silica gel using a mixture of ethyl acetate and cyclohexane (5:1) as eluent to give 26 g. of dimethyl 2-oxo-3-(3-trifluoromethylphenoxy)propylphosphonate having the following physical characteristics: IR (liquid film): ν; 1730, 1590, 1450, 1050–1030, 750 cm$^{-1}$; NMR (CCl$_4$ solution): δ; 7.50–6.70 (4H, m), 4.70 (2H, s), 3.65 (6H, d), 3.10 (2H, d).

760 mg. of sodium hydride (65.1% content) were suspended in 100 ml. of anhydrous tetrahydrofuran. With stirring under an atmosphere of nitrogen, 9.3 g. of dimethyl 2-oxo-3-(3-trifluoromethylphenoxy)propylphosphonate (obtained as described above) in 40 ml. of tetrahydrofuran were added to the suspension at 30° C. and the mixture stirred for 30 minutes.

4.5 g. of 1α-acetoxy-2α-(6-methoxycarbonylhex-cis-2-enyl)-3β-formyl-4α-(2-tetranhydropyranyloxy)-cyclopentane (prepared as described hereafter) in 15 ml. of tetrahydrofuran were added and the mixture stirred at 40° C. for 5 hours. The reaction mixture was then acidified with acetic acid, and silica gel was added to the mixture. The mixture was filtered, and the filtrate concentrated under reduced pressure. The residue was purified by column chromatograhy on silica gel using a mixture of ethyl acetate and benzene (1:8) as eluent to give 2.66 g. of methyl 9α-acetoxy-11α-(2-tetrahydropyranyloxy)-15-oxo-16-(3-trifluoromethylphenoxy)-17,18,19,20-tetranorprosta-cis-5,trans-13-dienoate having the following physical characteristics: TLC (developing solvent ethyl acetate - benzene = 1:8); Rf = 0.21; IR (liquid film): ν; 1730, 1690, 1620, 1590, 980 cm$^{-1}$; NMR (CCl$_4$ solution): δ; 7.50–6.20 (6H, m), 5.50–4.75 (3H, m), 4.62 (2H, s), 4.55–4.3 (1H, m), 3.55 (3H, s), 1.99 (3H, s).

1α-Acetoxy-2α-(6-methoxycarbonylhex-cis-2-enyl-3β-formyl-4α-(2-tetrahydropryanyloxy)cyclopentane, used as a starting material in the above procedure, was prepared from 2-oxa-3-oxo-6-syn-hydroxymethyl-7-anti-acetoxy-cis-bicyclo[3,3,0]octane, [prepared as described by E.J. Corey et al, J. Amer. Chem. Soc., 92, 397 (1970)], as follows:

190 g. of 2-oxa-3-oxo-6-syn-hydroxymethyl-7-anti-acetoxy-cis-bicyclo[3,3,0]octane in 1.5 liters of absolute methanol and 130 g. of potassium hydroxide were stirred at room temperature for 1 hour, and then successively cooled in an ice-bath, and neutralized with hydrochloric acid. The precipitate was filtered off and the filtrate was concentrated under reduced pressure. The residue was washed with ethanol, and then with ethyl acetate, and dried to give 124 g. of 2-oxa-3-oxo-6-syn-hydroxymethyl-7-anti-hydroxy-cis-bicyclo[3,3,0]octane as white crystallites having the following physical characteristics: m.p. 119° C.; IR (KBr tablet): ν; 3350, 2970–2880, 1740, 1480, 1440, 1410, 1380, 1335, 1305, 1270, 1205, 1100, 1080, 1060, 1040, 1020, 1000 and 975 cm$^{-1}$. NMR (CDCl$_3$ + deutero dimethyl sulphoxide solution): δ; 5.10–4.60 (1H, m), 4.29 (2H, s), 4.13–3.77 (1H, m) and 3.38 (2H, d); TLC (developing solvent methylene chloride-methanol = 20:1); Rf = 0.27.

124 g. of 2-oxa-3-oxo-6-syn-hydroxymethyl-7-anti-hydroxy-cis-bicyclo[3,3,0]octane (obtained as described above) were dissolved in absolute pyridine (1.4 liters) and cooled to −40° C. 74 g. of acetic anhydride were added dropwise and the mixture stirred for 5 hours at −40° to −20° C. and then for 16 hours at 0° C. The pyridine was evaporated off under reduced pressure and the residue was dissolved in 1 liter of ethyl acetate. 200 g. of sodium bisulphate were added, and the mixture stirred vigorously and filtered. The filtrate was concentrated under reduced pressure and the residue was purified by column chromatography on silica gel using a benzene-ethyl acetate mixture (1:3) as eluent to give 112 g. of 2-oxa-3-oxo-6-syn-acetoxymethyl-7-anti-hydroxy-cis-bicyclo[3,3,0]octane as colourless needles having the following physical characteristics: m.p.: 36° to 37° C.; IR (KBr tablet): ν; 3450, 2960, 2850, 1775, 1740, 1420, 1370, 1250, 1190, 1120, 1090, 1040 and 980 cm$^{-1}$; NMR (CDCl$_3$ solution): δ5.15–4.60 (1H, m), 4.3–3.75 (3H, m), 3.50 (1H, s) and 2.02 (3H, s); TLC (developing solvent methylene chloride-methanol = 20:1); Rf = 0.50.

43 g. of 2-oxa-3-oxo-6-syn-acetoxymethyl-7-anti-hydroxy-cis-bicyclo[3,3,0]octane (obtained as described above) were dissolved in 520 ml. of methylene chloride, 25g. of 2,3-dihydropyran and 0.52 g. of p-toluenesulphonic acid were added and the mixture stirred for 20 minutes at room temperature. The reaction mixture was neutralized with an aqueous solution of sodium bicarbonate, diluted with ethyl acetate, washed with water, dried and concentrated under reduced pressure to give 56 g. of 2-oxa-3-oxo-6-syn-acetoxymethyl-7-anti-(2-tetrahydropyranyloxy)-cis-bicyclo[3,3,0]octane as a colourless oil having the following physical characteristics: IR (liquid film): ν; 2950-2840, 1775, 1740, 1465, 1440, 1390-1340, 1240, 1180, 1140-1120, 1080, 1040 and 980 cm$^{-1}$; NMR (CDCl$_3$ solution): δ; 5.2-4.72 (1H, m), 4.72-4.30 (1H, m), 4.2-3.2 (5H, m) and 2.01 (3H, s); TLC (developing solvent methylene chloride-methanol = 20:1); Rf = 0.74.

56 g. of the acetyl ether (prepared as described above) were dissolved in 900 ml. of toluene and cooled to −60°C. 456 ml. of a 25(w/v)% solution of diisobutylaluminium hydride in toluene were added and the mixture stirred for 20 minutes at the same temperature; aqueous methanol was added in order to decompose the excess of diisobutylaluminium hydride. The resulting precipitate was filtered off and the filtrate was dried and concentrated under reduced pressure to give 35.2 g. of 2-oxa-3-hydroxy-6syn-hydroxymethyl-7-anti-(2-tetrahydropyranyloxy)-cis-bicyclo[3,3,0]octane as a colourless oil having the following physical characteristics: IR (liquid film): ν; 3400, 2940-2860, 1465-1440, 1380, 1355, 1325, 1260, 1200, 1140, 1120, 1075 and 1020 cm$^{-1}$; TLC (developing solvent ethyl acetate): Rf = 0.25.

37.6 g. of sodium hydride (content 63.5%) were suspended in 400 ml. of dimethyl sulphoxide and stirred at 70° C. for 1.5 hours to obtain sodium ethylsulphinylmethylide. The reaction mixture was allowed to cool to room temperature and then added dropwise to a solution of 226 g. of (4-carboxybutyl)triphenylphosphonium bromide in 460 ml. of dimethyl sulphoxide, the reaction temperature being kept within the range 20° to 25° C.

A solution of 35.2 g. of 2-oxa-3-hydroxy-6-syn-hydroxymethyl-7-anti-(2-tetrahydropyranyloxy)-cis-bicyclo-[3,3,0octane (prepared as described above) in 90 ml. of dimethyl sulphoxide was added to the above reaction mixture and stirred at 35° to 40° C. for 1.5 hours. The reaction mixture was then poured into 6 liters of ice-water and the neutral substances were removed by extraction with an ethyl acetate-diethyl ether mixture (1:1). The aqueous layer was acidified to pH 2 with a saturated aqueous oxalic acid solution and extracted with a diethyl ether-n-pentene mixture (1:1). The organic layer was washed with water, dried over sodium sulphate and concentrated under reduced pressure. The residue was subjected to column chromatography on silica gel using a benzene-methanol mixture (10:1) as eluent to give 35 g. of 2α-(6-carboxyhex-cis-2-enyl)-3β-hydroxymethyl-4α(2-tetrahydropyranyloxy)-cyclopentan-1α-ol as a colourless oil having the following physical characteristics:

IR (liquid film: ν; 3400, 2940-2860, −2300, 1710, 1450, 1435, 1400, 1355, 1245, 1200, 1140, 1120, 1075 and 1025 cm$^{-1}$; NMR (CDCl$_3$ solution): δ; 6.20 (3H, s), 5.50-5.10 (2H, m), 4.75-4.36 (1H, m), 4.24-3.85 (2H, m), and 3.85-3.0 (4H, m); TLC (developing solvent chloroform-tetrahydrofuran-acetic acid = 10:2:1); Rf = 0.53.

To a solution of 18.8g. of 2α-(6-carboxyhex-cis-2-enyl)-3β-hydroxymethyl-4α-(2-tetrahydropyranyloxy)-cyclopentan-1α-ol (obtained as described above) in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a cyclohexane-ethyl acetate mixture (2:1) as eluent to give 15.4 g. of 2α-(6-methoxycarbonyl-hex-cis-2-enyl)-3β-hydroxymethyl-4α-(2-tetrahydropyranyloxy)-cyclopentan-1α-ol as a colourless oil having the following physical characteristics:- IR (liquid film): ν; 3450, 2950, 2870, 1740, 1440, 1360, 1325, 1250, 1200, 1140, 1120, 1080, and 1025 cm$^{-1}$; NMR (CDCl$_3$ solution): δ; 5.55-5.00 (2H, m), 4.78-4.30 (1H, m), 4.20-3.06 (6H, m), 3.55 (3H, s) and 2.97 (2H, s); TLC (developing solvent methylene chloride - methanol = 19:1) Rf = 0.43.

13.1 g. of 2α-(6-methoxycarbonylhex-cis-2-enyl)-3β-hydroxymethyl-4α-(2-tetrahydropyranyloxy)-cyclopentan-1α-ol (obtained as described above) were dissolved in 250 ml. of absolute methylene chloride, and 25 ml. of pyridine were added. The air in the apparatus was replaced with nitrogen and the contents cooled to −20° C. To the solution was added dropwise a solution of 5.1 ml. of trimethylchlorosilane in 30 ml. of methylene chloride with stirring and stirring was continued at the same temperature for 30 minutes. A sample of the product thus obtained had the following physical characteristics:- TLC (developing solvent benzene - ethyl acetate = 2:1); Rf = 0.61.

A solution of 2.9 ml of acetyl chloride in 20 ml. of methylene chloride was added dropwise to the above reaction mixture and stirred at room temperature for 30 minutes. Then 2 ml. of ethanol were added to decompose the excess of acetyl chloride. Pyridine in the reaction mixture was neutralized by the addition of 50 g. of sodium bisulphate, and the resulting precipitate was filtered off. The filtrate was concentrated under reduced pressure to give a residue having the following physical characteristic:- TLC (developing solvent benzene - ethyl acetate = 2:1); Rf = 0.82.

The residue was dissolved in 300 ml. of ethyl acetate, 100 ml. of a saturated aqueous solution of oxalic acid were added and stirred vigorously at room temperature. The organic layer was separated, washed successively with water, aqueous sodium bisulphate solution, water and aqueous sodium chloride solution, dried over sodium sulphate and concentrated under reduced pressure to give 13.7 g. of crude product. The crude product was subjected to column chromatography on silica gel using a benzene-ethyl acetate mixture (3:1) as eluent to give 7.45 g. of 1α-acetoxy-2α-(6-methoxycarbonylhex-cis-2-enyl)-3α-hydroxymethyl-4α-(2-tetrahydropyranyloxy)-cyclopentane, 2.40 g. of 1α-hydroxy-2α-(6-methycarbonylhex-cis-2-enyl)-3α-hydroxymethyl-4α-(2-tetrahydropyranyloxy)-cyclopentane, 720 mg. of 1α-hydroxy-2α-(6-methoxycarbonylhex-cis-2-enyl)-3α-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α-(2-tetrahydropyranyloxy)-cyclopentane.

1α-Acetoxy-2α-(6-methoxycarbonylhex-cis-2-enyl)-3β-hydroxymethyl-4α-(2-tetrahydropyranyloxy)-cyclopentane had the following physical characteristics:- IR (liquid film): ν; 3450, 3000, 2950, 2870, 1740, 1440, 1380, 1330, 1250, 1200, 1160, 1140, 1080, 1030, 980, 920, 875 and 815 cm$^{-1}$; NMR (CDCl$_3$ solution): δ; 5.45-5.27 (2H, m), 5.16-4.92 (1H, m) 4.76-4.46 (1H, m), 4.27-3.96 (1H, m), 3.67 (3H, s), 2.98-2.64 (1H, m) and 2.05 (3H, s); TLC (developing solvent benzene - ethyl acetate = 2:1); Rf = 0.27.

Under an atmosphere of nitrogen, 4.4 ml. of pyridine were dissolved in 80 ml. of methylene chloride, 2.88 g. of chromium trioxide were added with stirring and the mixture was then stirred for 15 minutes. 12 g. of infusorial earth were added to the reaction mixture, and then there was added a solution of 956 mg. of 1α-acetoxy-2α-(6-methoxycarbonylhex-cis-2-enyl)-3β-hydroxymethyl- 4α-(2-tetrahydropyranyloxy)-cyclopentane (prepared as described above) in 20 ml. of methylene chloride. After stirring for 10 minutes, 20 g. of sodium bisulphate were added to the reaction mixture and stirring was continued for a further 10 minutes. The resulting precipitate was filtered off and the filtrate was concentrated under reduced pressure. The residue was subjected to silica gel column chromatography using a benzene-ethyl acetate mixture (5:1) as eluent to give 768 mg. of 1α-acetoxy-2α-(6-methoxycarbonylhex-cis-2-enyl)-3β-formyl-4α-(2-tetrahydropyranyloxy)-cyclopentane as a colourless oil having the following physical characteristics:

IR (liquid film): ν; 3000, 2950, 2860, 2725, 1740, 1440, 1380, 1325, 1255, 1200, 1165, 1140, 1085, 1030, 980, 920, 800 and 820 cm$^{-1}$; NMR (CDCl$_3$ solution): δ ; 9.85–9.68 (1H, m), 5.45–4.96 (1H, m), 4.68–4.48 (1H, m), 4.48–4.25 (1H, m), 3.67 (3H, s), and 2.08 (3H, s); TLC (developing solvent benzene - ethyl acetate = 2:1); Rf = 0.66.

To a solution of 1.04 g. of methyl 9α-acetoxy-11α-(2-tetrahydropyranyloxy)-15-oxo-16-(3-trifluoromethylphenoxy)-17,18,19,20-tetranorprosta-cis-5,trans-13-dienoate (prepared as described above) in 20 ml. of methanol, there was added carefully 195 mg. of sodium borohydride whilst keeping the temperature at −50° C. After 20 minutes, the mixture was neutralized with acetic acid and the methanol was evaporated under reduced pressure. The resulting mixture was extracted with ethyl acetate. The organic extracts were washed with an aqueous sodium bicarbonate solution, water and an aqueous sodium chloride solution, dried over magnesium sulphate and concentrated under reduced pressure. The residue was purified by column chromatography on silica gel using a mixture of ethyl acetate and benzene (1:4) as eluent to give 247 mg. of methyl 9α-acetoxy-11α-(2-tetrahydropyranyloxy)-15α-hydroxy-16-(3-trifluoromethylphenoxy)-17,18,19,20-tetranorprosta-cis-5,trans-13-dienoate and 288 mg. of its 15β-hydroxy isomer and 370 mg. of a mixture thereof having the following physical characteristics: TLC (developing solvent ethyl acetate - benzene = 1:2); 15α-hydroxy compound : Rf = 0.42; 15β-hydroxy compound : Rf = 0.47; IR (liquid film): ; 3420, 1730, 1570, 1440, 980 cm$^{-1}$; NMR (CDCl$_3$ solution): δ ; 7.60–7.00 (4H, m), 5.95–5.65 (2H, m), 5.60–5.25 (2H, m), 5.25–4.95 (1H, m), 4.80–4.40 (2H, m), 4.02 (2H, d), 3.68 (3H, s), 2.08 (3H, s).

REFERENCE EXAMPLE 2

Methyl 2-phenylseleno-9α,15α-dihydroxy-11α-(2-tetrahydropyranyloxy)-16-(3-trifluoromethylphenoxy)-17,18,19,20-tetranorprosta-cis-5,trans-13-dienoate A solution of 0.391 ml. of diisopropylamine in 7 ml. of tetrahydrofuran was cooled to −78° C., and to it 2.08 ml. of a 1.35 M solution of n-butyllithium in n-hexane were added dropwise and the mixture stirred for 15 minutes at −78° C. to give lithium diisopropylamide. To the lithium diisopropylamide solution, 447 mg. of methyl 9α,15α-dihydroxy-11α-(2-tetrahydropyranyloxy)-16-(3-trifluoromethylphenoxy)-17,18,19,20-tetranorprosta-cis-5,trans-13-dienoate (prepared as described in Reference Example 1) in 3 ml. of tetrahydrofuran were added dropwise at −78° C. for 10 minutes and the reaction mixture stirred for 20 minutes at the same temperature. A solution of 920 mg. of diphenyldiselenide in 4 ml. of tetrahydrofuran was added dropwise to the reaction mixture at −78° C. and stirring was continued for 1 hour. The reaction mixture was then poured into an aqueous solution of ammonium chloride and extracted with ethyl acetate. The extract was washed with water, 1N hydrochloric acid, an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (5:1) as eluent to give 219 mg. of the title compound having the following physical characteristic: TLC (developing solvent benzene - ethyl acetate = 2:1); Rf = 0.3.

EXAMPLE 1

Methyl 9α,15α-dihydroxy-11α-(2-tetrahydropyranyloxy)-16-(3-trifluoromethylphenoxy)-17,18,19,20-tetranorprosta-trans-2,cis-5,trans-13-trienoate 219 mg. of methyl 2-phenylseleno-9α,15α-dihydroxy-11α-(2-tetrahydropyranyloxy)-16-(3-trifluoromethylphenoxy)-17,18,19,20-tetranorporsta-cis-5,trans-13-dienoate (prepared as described in Reference Example 2) were dissolved in 8 ml. of a mixture of ethyl acetate and tetrahydrofuran (1:1) and stirred with 0.191 ml. of 30% hydrogen peroxide at 30° C. for 40 minutes. The reaction mixture was then poured into water, washed with an aqueous solution of sodium carbonate, water and an aqueous solution of sodium chloride, dried over magnesium sulphate and concentrated under reduced pressure to give 198 mg. of the title compound having the following physical characteristics: TLC (developing solvent benzene — ethyl acetate = 2:1); Rf = 0.18; IR (liquid film): ν; 3400, 2440, 1730, 1660, 1600, 1500, 980 cm$^{-1}$; NMR (CCl$_4$ solution): δ; 7.6–6.3 (5H, m), 6.2–5.0 (5H, m).

EXAMPLE 2

Methyl 9α,11α,15α-trihydroxy-16-(3-trifluoromethylphenoxy)-17,18,19,20-tetranorprosta-trans-2,cis-5,trans-13-trienoate [or 16-(3-triflurormethylphenoxy)-17,18,19,20-tetranor-trans-Δ$^2$-PGF$_{2α}$ methyl ester]

A solution of 198 mg. of methyl 9α,15α-dihydroxy-11α-(2-tetrahydropyranyloxy)-16-(3-trifluoromethylphenoxy)-17,18,19,20-tetranorprosta-trans-2,cis-5,-trans-13-trienoate (prepared as described in Example 1) in 5 ml. of tetrahydrofuran was stirred with 2 ml. of 1N hydrochloric acid at 40° C. for 1 hour. The reaction mixture was then poured into water, extracted with ethyl acetate, and the extract was washed with water and an aqueous solution of sodium chloride, dried over magnesium sulphate and concentrated under reduced pressure. The residue was purified by column chromatograpy on silica gel using a mixture of ethyl acetate and cyclohexane (1:1) as eluent to give 64 mg. of the title compound having the following physical characteristics: TLC (developing solvent chloroform — tetrahydrofuran — acetic acid = 10:2:1); Rf = 0.21; IR (liquid film): ν; 3350, 2900, 1720, 1660, 1600, 1500, 980 cm$^{-1}$; NMR (CDCl$_3$ solution δ; 7.50–7.08 (4H, m), 6.42 (1H, dt), 5.80 (1H, d), 5.77–5.60 (2H, m), 5.60;14 5.20 (2H, m), 4.65–4.35 (1H, m).

REFERENCE EXAMPLE 3

Methyl 9α,15α-dihydroxy-11α-(2-tetrahydropyranyloxy)-16-phenoxy-17,18,19,20-tetranorprosta-cis-5,trans-13-dienoate 701 mg. of methyl 9α-acetoxy-11α-(2-tetrahydropyranyloxy)-15α-hydroxy-16-phenoxy-17,18,19,20-tetranorprosta-cis-5,trans-13-dienoate (prepared as described hereafter) were dissolved in 8 ml. of methanol and stirred with 200 mg. of potassium carbonate at 50° C. for 1 hour. The reaction mixture was then neutralized with acetic acid and diluted with ethyl acetate. The solution was washed with water, an aqueous solution of sodium bicarbonate and an aqueous solution of sodium chloride, dried over sodium sulphate and concentrated under reduced pressure to give 655 mg. of the title compound having the following physical characteristics: TLC (developing solvent benzene - ethyl acetate = 1:1); Rf = 0.38; IR (liquid film): ν; 3450, 2940, 2860, 1730, 1595, 1580, 1485, 1425, 1240, 1165, 1125, 1065, 1030, 965 cm$^{-1}$; NMR (CDCl$_3$ solution): δ: 7.65–6.60 (5H, m), 5.90–5.56 (2H, m), 5.56–5.20 (2H, m), 4.95–4.30 (2H, m), 4.30–3.20 (9H, m).

Methyl 9α-acetoxy-11α-(2-tetrahydropyranyloxy)-15α-hdroxy-16-phenoxy-17,18,19,20-tetranorprosta-cis-5,trans-13-dienoate, used as a starting material in the above procedure, was prepared as follows:

40.1 g. of dimethyl methylphosphonate were dissolved in 200 ml. of anhydrous tetrahydrofuran, to which 154 ml. of a 2N solution of n-butyllithium in n-hexane were added dropwise whilst maintaining the temperature from −60° to −70° C. After stirring for 20 minutes, 15 g. of ethyl phenoxyacetate in 80 ml. of tetrahydrofuran were added to the solution. The mixture was stirred at the same temperature for 2 hours and then at room temperature overnight. The reaction mixture was neutralized with acetic acid and concentrated under reduced pressure. The residue was dissolved in a small amount of water and extracted with diethyl ether. The ethereal extracts were washed with an aqueous sodium chloride solution, dried over magnesium sulphate and concentrated under reduced pressure. The residue was purified by distillation in vacuo to give 18.9 g. of dimethyl 2-oxo-3-phenoxypropylphosphonate having the following physical characteristics: boiling point: 145° to 150° C./0.1 mm.Hg; IR (liquid film): ν; 2950, 1740, 1600, 1500, 1250, 1040 cm$^{-1}$; NMR (CDCl$_3$ solution): δ; 7.60–6.50 (5H, m), 5.00–4.40 (2H, broad s), 4.10–3.55 (6H, d), 3.55–2.80 (2H, d).

1.1 g. of sodium hydride (65.1% content) were suspended in 200 ml. of anhydrous tetrahydrofuran. With stirring under an atmosphere of nitrogen, 7.83 g. of dimethyl 2-oxo-3-phenoxypropylphosphonate (prepared as described above) in 100 ml. of tetrahydrofuran were added to the suspension at 30° C. and the mixture stirred for 30 minutes.

4.0 g. of 1α-acetoxy-2α-(6-methoxycarbonylhex-cis-2-enyl)-3β-formyl-4α-(2-tetrahydropyranyloxy)-cyclopentane (prepared as described in Reference Example 1) in 200 ml. of tetrahydrofuran were added and the mixture stirred at 40° C. for 3.5 hours. The reaction mixture was then acidified with acetic acids, and silica gel was added to the mixture. The mixture was filtered, and the filtrate concentrated under reduced pressure. The residue was purified by column chromatography on silica gel using a mixture of benzene and ethyl acetate (6:1) as eluent to give 3.82 g. of methyl 9α-acetoxy-11α-(2-tetrahydropyranyloxy)-15-oxo-16-phenoxy-17,18,19,20-tetranorprosta-cis-5,trans-13-dienoate having the following physical characteristics: TLC (developing solvent benzene - ethyl acetate = 2:1); Rf = 0.71; IR (liquid film): ν; 2950, 1740, 1600, 1500, 1380, 1250 cm$^{-1}$; NMR (CDCl$_3$ solution): δ: 7.90–6.20 (7H, m), 5.80–4.90 (3H, m), 4.90–4.35 (3H, m), 4.35–3.10 (6H, m).

To a solution of 3.82 g. of methyl 9α-acetoxy-11α-(2-tetrahydropyranyloxy)-15-oxo-16-phenoxy-17,18,19,20-tetranorprosta-cis-5,trans-13-dienoate (prepared as described above) in 50 ml. of methanol, there were added carefully 825 mg. of sodium borohydride whilst keeping the temperature at −40° to −30° C. After 30 minutes, the mixture was neutralized with acetic acid and the methanol was evaporated under reduced pressure. The resulting mixture was extracted with ethyl acetate. The organic extracts were washed with an aqueous sodium bicarbonate solution, water and an aqueous sodium chloride solution, dried over magnesium sulphate and concentrated under reduced pressure. The residue was purified by column chromatography on silica gel using a mixture of ethyl acetate and benzene (1:4) as eluent to give 1.42 g. of methyl 9α-acetoxy-11α-(2-tetrahydropyranyloxy)-15α-hydroxy-16-phenoxy-17,18,19,20-tetranorprosta-cis-5,trans-13-dienoate and 1.26 g. of its 15β-hydroxy isomer, and 870 mg. of a mixture thereof having the following physical characteristics:

TLC (developing solvent ethyl acetate - benzene = 1:2); 15α-hydroxy compound : Rf = 0.42; 15β-hydroxy compound : Rf = 0.51; IR (liquid film): ν; 3420, 1735, 1570, 1440, 980 cm$^{-1}$; NMR (CDCl$_3$ solution): δ; 7.65–7.00 (5H, m), 5.95–5.62 (2H, m), 5.60–5.23 (2H, m), 5.23–4.94 (1H, m), 4.85–4.40 (1H, m), 4.40–3.25 (5H, m), 3.70 (3H, s), 3.12 (2H, d), 2.08 (3H, s).

REFERENCE EXAMPLE 4

Methyl 9α,11α,15α-tris(2-tetrahydropyranyloxy)-16-phenoxy-17,18,19,20-tetranorprosta-cis-5,trans-13-dienoate 3 mg. of p-toluenesulphonic acid and 0.4 ml. of 2,3-dihydropyran were added to a solution of 647 mg. of methyl 9α,15α-dihydroxy-11α-(2-tetrahydropyranyloxy)-16-phenoxy-17,18,19,20-tetranorprosta-cis-5,trans-13-dienoate (prepared as described in Reference Example 3) in 10 ml. of methylene chloride and the reaction mixture was stirred at room temperature for 30 minutes and then neutralized with an aqueous solution of sodium bicarbonate. The reaction mixture was diluted with ethyl acetate, washed with water and an aqueous solution of sodium chloride, dried over sodium sulphate and concentrated under reduced pressure. The residue was purified by column chromatography on silica gel using a mixture of benzene and ethyl acetate (6:1) as eluent to give 735 mg. of the title compound having the following physical chracteristics: TLC (developing solvent benzene - ethyl acetate = 1:1); Rf = 0.65; IR (liquid film): ν; 2940, 2865, 1740, 1600, 1585, 1495, 1450, 1435, 1355, 1245, 1200, 1130, 1075, 1020, 980 cm$^{-1}$; NMR (CCl$_4$ solution): δ; 7.50–6.45 (5H, m), 5.90–5.05 (4H, m), 4.95–4.20 (4H, m), 4.20–2.95 (13H, m).

REFERENCE EXAMPLE 5

Methyl 2-phenylseleno-9α,11α,15α-tris(2-tetrahydropyranyloxy)-16-phenoxy-17,18,19,20-tetranorprosta-cis-5,trans-13-dienoate A solution of 0.27 ml. of diisopropylamine in 10 ml. of tetrahydrofuran was cooled to −78° C., and to it 1.2 ml. of a 1.4M solution of n-butyllithium in n-hexane were added dropwise and the mixture stirred for 15 minutes at −78° C. to give lithium diisopropylamide. To the lithium diisopropylamide solution, 723 mg. of methyl 19α,-11α,15α-tris(2-tetrahydropyranyloxy)-16-phenoxy-17,18,19,20-tetranorprosta-cis-5,trans-13-dienoate (prepared as described in Reference Example 4) in 10 ml. of tetrahydrofuran were added dropwise at −78° C. and the mixture stirred for 20 minutes at the same temperature. A solution of 530 mg. of diphenyldiselenide in 8 ml. of tetrahydrofuran was added dropwise to the reaction mixture at −78° C., which was stirred for 30 minutes at −78° C. and for another 30 minutes at room temperature. The reaction mixture was then acidified with dilute hydrochloric acid, extracted with ethyl acetate, and the extract was washed with water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (9:1) as eluent to give 665 mg. of the title compound having the following physical characteristics: TLC (developing solvent benzene - ethyl acetate = 3:1); Rf = 0.63; IR (liquid film): $\nu$; 2950, 2880, 1740, 1602, 1590, 1495, 1438, 1355, 1250, 1200, 1135, 1075, 1020, 980 cm$^{-1}$; NMR (CCl$_4$ solution): $\delta$; 7.80–6.60 (10H, m), 6.00–5.03 (4H, m), 5.03–4.32 (4H, m), 4.32–3.05 (13H, m).

EXAMPLE 3

Methyl 9α,11α,15α-tris(2-tetrahydropyranyloxy)-16-phenoxy-17,18,19,20-tetranorprosta-trans-2,cis-5,trans-13-trienoate 665 mg. of methyl 2-phenylselno-9α,11α,15α-tris(2-tetrahydropyranyloxy)-16-phenoxy-17,18,19,20-tetranorprosta-cis-5,trans-13-dienoate (prepared as described in Reference Example 5) were dissolved in 10 ml. of a mixture of ethyl acetate and methanol (3:2) and the solution stirred with 0.7 ml. of 30% hydrogen peroxide at 30° C. for 1 hour. The reaction mixture was then diluted with ethyl acetate, washed with water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (9:1) as eluent to give 392 mg. of the title compound having the following physical characteristics: TLC (developing solvent benzene - ethyl acetate = 3:1); Rf = 0.58; IR (liquid film): $\nu$; 2940, 2860, 1725, 1650, 1600, 1585, 1490, 1435, 1325, 1245, 1200, 1130, 1075, 1030, 1020, 980 cm$^{-1}$; NMR (CCl$_4$ solution): $\delta$; 7.75–6.50 (6H, m), 6.20–5.15 (5H, m), 5.10–4.40 (4H, m), 4.40–3.18 (13H, m), 3.18–2.75 (2H, m).

EXAMPLE 4

Methyl 9α,11α,15α-trihydroxy-16-phenoxy-17,18,19,20-tetranorprosta-trans-2,cis-5,-trans-13-trienoate [or 16-phenoxy-17,18,19,20-tetranor-trans-$\Delta^2$-PGF$_{2\alpha}$-methyl ester]

390 mg. of methyl 9α,11α,15α-tris(2-tetrahydropyranyloxy)-16-phenoxy-17,18,19,20-tetranorprosta-trans-2,cis-5,trans-13-trienoate (prepared as described in Example 3) were dissolved in a mixture of 0.5 ml. of tetrahydrofuran and 5 ml. of 65% aqueous acetic acid and the reaction mixture was stirred at 60° C. for 1 hour. The reaction mixture was then diluted with ethyl acetate, washed with water, an aqueous solution of sodium bicarbonate and an aqueous solution of sodium chloride, dried over sodium sulphate and concentrated under reduced pressure. The residue was purified by column chromatography on silica gel using a mixture of cyclohexane and ethyl acetate (2:3) as eluent to give 171 mg. of the title compound having the following physical characteristics: TLC (developing solvent ethyl acetate); Rf = 0.30; TR (liquid film): $\nu$; 3400, 3020, 2940, 1725, 1655, 1600, 1590, 1495, 1435, 1335, 1280, 1250, 1175, 1080, 1045, 975 cm$^{-1}$; NMR (CDCl$_3$ solution): $\delta$; 7.45–6.66 (6H, m), 5.96–5.20 (5H, m), 4.63–4.35 (1H, m), 4.25–3.78 (4H, m), 3.69 (3H, s), 2.95 (2H, t).

REFERENCE EXAMPLE 6

Methyl 9α,15α-dihydroxy-11α-(2-tetrahydropyranyloxy)-16-(3-chlorophenoxy)-17,18,19,20-tetranoprosta-cis-5,trans-13-dienoate By the same procedure as described in Reference Example 3, 776 mg. of the title compound were obtained from 845 mg. of methyl 9α-acetoxy-11α-(2-tetrahydropyranyloxy)-15α-hydroxy-16-(3-chlorophenoxy)-17,18,19,20-tetranorprosta-cis-5,trans-13-dienoate (prepared as described hereafter) and 250 mg. of potassium carbonate in 10 ml. of methanol. The title compound showed the following physical characteristics: TLC (developing solvent benzene - ethyl acetate = 2:1); Rf = 0.28; IR (liquid film): $\nu$; 3450, 2950, 2870, 1740, 1600, 1580, 1480, 1435, 1250, 1135, 1075, 1030, 975 cm$^{-1}$; NMR (CCl$_4$ solution): $\delta$; 7.45–6.50 (4H, m), 5.90–5.50 (2H, m), 5.50–5.05 (2H, m), 4.95–4.20 (2H, m), 4.20–3.10 (9H, m), 2.90 (2H, s).

Methyl 9α-acetoxy-11α-(2-tetrahydropranyloxy)-15α-hydroxy-16-(3-chlorophenoxy)-17,18,19,20-tetranorprosta-cis-5,trans-13-dienoate, used as a starting material in the above procedure, was prepared as follows:

25.6 g. of 3-chlorophenol were added dropwise to a sodium ethoxide solution prepared from 4 g. of sodium and 150 ml. of ethanol. After stirring for 30 minutes at room temperature, 16 g. of ethyl bromoacetate were added dropwise at room temperature and the reaction mixture was refluxed for 1 hour. The reaction mixture was then concentrated under reduced pressure, the residue was diluted with ethyl acetate, washed with 1N sodium hydroxide solution, water and an aqueous solution of sodium chloride, dried over magnesium sulphate and concentrated under reduced pressure to give 9.2 g. of ethyl (3-chlorophenoxy)acetate having the following physical characteristic: NMR (CCl$_4$ solution): $\delta$; 7.3–6.5 (4H, m), 4.50 (2H, s), 4.19 (2H, q), 1.26 (3H, t).

16 g. of dimethyl methylphosphonate were dissolved in 200 ml. of anhydrous tetrahydrofuran, and then 100 ml. of a 1.3M solution of n-butyllithium in n-hexane were added dropwise while maintaining the temperature at $-60°$ C. After stirring for 15 minutes, 11.9 g. of ethyl (3-chlorophenoxy)acetate (obtained as described above) in 60 ml. of anhydrous tetrahydrofuran were added to the solution. The mixture was stirred at $-70°$ C. for 2 hours and then at 4° C. overnight. The reaction mixture was acidified to pH 4 with acetic acid and concentrated under reduced pressure. The residue was diluted with diethyl ether, washed with water, dried over magnesium sulphate and concentrated under reduced pressure. The residue was purified by distillation in vacuo ot give 12.0 g. of dimethyl 2-oxo-3-(3-chlorophenoxy)propylphosphonate having the following physical characteristics: boiling point: 175° to 180° C./0.1 to 0.05 mm Hg; NMR (CCl$_4$ solution): $\delta$; 7.35–6.5 (4H, m), 4.70 (2H, s), 3.72 (6H, d), 3.18 (2H, d).

1.03 g. of sodium hydride (63% content) were suspended in 120 ml. of anhydrous tetrahydrofuran. With stirring under an atmosphere of nitrogen, 8.76 g. of dimethyl 2-oxo-3-(3-chlorophenoxy)propylphosphonate (prepared as described above) in 40 ml. of tetrahydrofuran were added to the suspension at 30° C. and the mixture stirred for 20 minutes.

4.16 g. of 1$\alpha$-acetoxy-2$\alpha$-(6-methoxycarbonylhex-cis-2-enyl)-3$\beta$-formyl-4$\alpha$-(2-tetrahydropyranyloxy)-cyclopentane (prepared as described in Reference Example 1) in 40 ml. of tetrahydrofuran were added and the mixture stirred at 30° C. for 1.5 hours, at 45° C. for 1 hour and at 60° C. for 2 hours. The reaction mixture was then acidified with acetic acid, and silica gel was added to the mixture. The mixture was filtered, and the filtrate concentrated under reduced pressure. The residue was purified by column chromatography on silica gel using mixtures of benzene and ethyl acetate (20:1, 15:1, 10:1 and 8:1) as eluent to give 2.94 g. of methyl 9$\alpha$-acetoxy-11$\alpha$-(2-tetrahydropyranyloxy)-15-oxo-16-(3-chlorophenoxy)-17,18,19,20-tetranorprosta-cis-5,trans-13-dienoate having the following physical characteristics: TLC (developing solvent benzene - ethyl acetate = 2:1); Rf = 0.78; IR (liquid film): $\nu$; 3000, 2930, 2850, 1740, 1695, 1625, 1600, 1585, 1480, 1250, 1050, 980, 780, 700 cm$^{-1}$; NMR (CDCl$_3$ solution): $\delta$; 7.5–6.4 (6H, m), 5.7–5.25 (2H, m), 5.25–5.0 (1H, m), 4.80 (2H, s), 4.75–4.4 (1H, m), 3.70 (3H, s), 2.10 (3H, s).

To a solution of 2.87 g. of methyl 9$\alpha$-acetoxy-11$\alpha$-(2-tetrahydropyranyloxy)-15-oxo-16-(3-chlorophenoxy)-17,18,19,20-tetranorprosta-cis-5,trans-13-dienoate (prepared as described above) in 50 ml. of a mixture of methanol and tetrahydrofuran (1:1), there was added carefully 760 mg. of sodium borohydride while keeping the temperature at $-40°$ to $-45°$ C. After 10 minutes, the mixture was acidified to pH 4 with acetic acid and concentrated under reduced pressure. The residue was diluted with ethyl acetate, washed with an aqueous solution of sodium bicarbonate, water and an aqueous solution of sodium chloride, dried over magnesium sulphate and concentrated under reduced pressure. The residue was purified by column chromatography on silica gel using a mixture of benzene and ethyl acetate (3:1) as eluent to give 1.05 g. of methyl 9$\alpha$-acetoxy-11$\alpha$-(2-tetrahydropyranyloxy)-15$\alpha$-hydroxy-16-(3-chlorophenoxy)-17,18,19,20-tetranorprosta-cis-5,trans-13-dienoate and 1.16 g. of its 15$\beta$-hydroxy isomer.

The 15$\alpha$-hydroxy compound has the following physical characteristics: TLC (developing solvent benzene — ethyl acetate = 2:1);
Rf = 0.38; (15$\beta$-hydroxyisomer : Rf = 0.45); IR (liquid film): $\nu$; 3430, 2925, 2850, 1740, 1600, 1585, 980, 780, 700 cm$^{-1}$; NMR (CDCl$_3$ solution): $\delta$; 7.4–6.7 (4H, m), 5.95–5.65 (2H, m), 5.65–5.3 (2H, m), 5.3–4.9 (1H, m), 4.9–4.4 (2H, m), 4.0 (2H, d), 3.72 (3H, s), 2.10 (3H, s).

REFERENCE EXAMPLE 7

Methyl 9$\alpha$,11$\alpha$,15$\alpha$-tris(2-tetrahydropyranyloxy)-16-(3-chlorophenoxy)-17,18,19,20-tetranorprosta-cis-5,trans-13-dienoate By the same procedure as described in Reference Example 4, 1063 mg. of the crude title compound were obtained from 776 mg. of methyl 9$\alpha$,15$\alpha$-dihydroxy-11$\alpha$-(2-tetrahydropyranyloxy)-16-(3-chlorophenoxy)-17,18,19,20-tetranorprosta-cis-5,trans-13-dienoate (prepared as described in Reference Example 6). The crude product was purified by column chromatography on silica gel using a mixture of benzene and ethyl acetate (9:1) as eluent to give 937 mg. of the title compound having the following physical characteristics: TLC (developing solvent benzene - ethyl acetate = 2:1); Rf = 0.52; IR (liquid film): $\nu$; 2950, 2870, 1740, 1600, 1580, 1480, 1450, 1440, 1355, 1255, 1200, 1160, 1135, 1080, 1035, 1025, 980 cm$^{-1}$; NMR (CCl$_4$ solution): $\delta$; 7.45–6.50 (4H, m), 5.95–5.10 (4H, m), 5.00–4.30 (4H, m), 4.30–3.05 (13H, m).

REFERENCE EXAMPLE 8

Methyl 2-phenylseleno-9$\alpha$,11$\alpha$,15$\alpha$-tris(2-tetrahydropyranyloxy)-16-(3-chlorophenoxy)-17,18,19,20-tetranorprosta-cis-5,trans-13-dienoate A solution of 0.45 ml. of diisopropylamine in 10 ml. of tetrahydrofuran was cooled to $-78°$ C., and to it 2 ml. of a 1.4M solution of n-butyllithium in n-hexane were added dropwise and the mixture stirred for 15 minutes at $-78°$ C. to give lithium diisopropylamide. To the lithium diisopropylamide solution, 937 mg. of methyl 9$\alpha$,11$\alpha$,15$\alpha$-tris(2-tetrahydropyranyloxy)-16-(3-chlorophenoxy)-17,18,19,20-tetranorprosta-cis-5,trans-13-dienoate (prepared as described in Reference Example 7) in 7 ml. of tetrahydrofuran were added dropwise at $-78°$ C. and the mixture stirred for 20 minutes at the same temperature. A solution of 900 mg. of diphenyldiselenide in 5 ml. of tetrahydrofuran was added dropwise to the reaction mixture at $-78°$ C., which was stirred for 30 minutes at $-78°$ C. and for another 30 minutes at room temperature. The reaction mixture was then acidified with dilute hydrochloric acid, extracted with ethyl acetate, and the extract was washed with water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (9:1) as eluent to give 736 mg. of the title compound having the following physical characteristics: TLC (developing solvent benzene - ethyl acetate = 3:1); Rf = 0.57; IR (liquid film: $\nu$; 3070, 2950, 2870, 1735, 1597, 1580, 1475, 1435, 1350, 1245, 1200, 1155, 1130, 1070, 1020, 980 cm$^{-1}$; NMR (CCl$_4$ solution): $\delta$;

7.72–6.45 (9H, m), 6.00–5.02 (4H, m), 5.02–4.28 (4H, m), 4.28–3.00 (13H, m).

EXAMPLE 5

Methyl 9α,11α,15α-tris(2-tetrahydropyranyloxy)-16-(3-chlorophenoxy)-17,18,19,20-tetranorprosta-trans-2,cis-5,trans-13-trienoate By the same procedure as described in Example 3, 510 mg. of the title compound were obtained from 736 mg. of methyl 2-phenylseleno-9α,11α,15α-tris(2-tetrahydropyranyloxy)-16-(3-chlorophenoxy)-17,18,19,20-tetranorprosta-cis-5,trans-13-dienoate (prepared as described in Reference Example 8). The title compound showed the following physical characteristics: TLC (developing solvent benzene — ethyl acetate = 3:1); Rf = 0.50; IR (liquid film): ν; 2960, 2880, 1730, 1655, 1595, 1580, 1480, 1435, 1325, 1280, 1200, 1160, 1135, 1080, 1035, 1025, 985 cm$^{-1}$; NMR (CCl$_4$ solution): δ; 7.40–6.50 (5H, m), 6.00–5.10 (5H, m), 4.93–4.30 (4H, m), 4.30–3.10 (13H, m), 3.10–2.70 (2H, m).

EXAMPLE 9

Methyl 9α,11α,15α-trihydroxy-16-(3-chlorophenoxy)-17,18,19,20-tetranorprosta-trans-2,cis-5,trans-13-trienoate [or 16-(3-chlorophenoxy)-17,18,19,20-tetranor-trans-Δ$^2$-PGF$_{2α}$methyl ester]

By the same procedure as described in Example 4, 230 mg. of the title compound were obtained from 510 mg. of methyl 9α,11α,15α-tris(2-tetrahydropyranyloxy)-16-(3-chlorophenoxy)-17,18,19,20-tetranorprosta-trans-2,cis-5,trans-13-trienoate (prepared as described in Example 5) in a mixture of 1 ml. of tetrahydrofuran and 10 ml. of 65% aqueous acetic acid. The title compound showed the following physical characteristics: TLC (developing solvent ethyl acetate): Rf = 0.32; IR (liquid film): ν; 3400, 3030, 2940, 1720, 1655, 1600, 1580, 1480, 1435, 1335, 1290, 1175, 1040, 975 cm$^{-1}$; NMR (CDCl$_3$ solution): δ; 7.40–6.60 (5H, m), 5.97–5.20 (5H, m), 4.64–4.33 (1H, m), 4.30–3.79 (4H, m), 3.69 (3H, s), 2.95 (2H, t).

EXAMPLE 7

16-Phenoxy-17,18,19,20-tetranorprosta-trans-2,cis-5,trans-13-triene-1,9α,11α,15α-tetrol [or 16-phenoxy-17,18,19,20-tetranor-trans-Δ$^2$-PGF$_{2α}$alcohol]

64 mg. of 16-phenoxy-17,18,19,20-tetranor-trans-Δ$^2$-PGF$_{2α}$methyl ester (which may be prepared as described in Example 4 or in Example 10 hereafter) were dissolved in 8 ml. of dry toluene and, after cooling to −78° C., 1.5 ml. of a 25(w/v)% solution of diisobutylaluminium hydride in toluene were added dropwise under an atmosphere of nitrogen with stirring. After stirring for 40 minutes at the same temperature, the reaction mixture was treated with 1 ml. of methanol. The reaction mixture was then warmed to 0° C. and 3 ml. of water was added to the mixture, which was then stirred to separate a precipitate. The resulting precipitate was filtered off and the filtrate was diluted with ethyl acetate, washed with water and an aqueous solution of sodium chloride, dried over sodium sulphate and concentrated under reduced pressure. The residue was purified by column chromatography on silica gel using a mixture of ethyl acetate and cyclohexane (2:1) as eluent to give 42 mg. of the title compound having the following physical characteristics: TLC (developing solvent ethyl acetate); Rf = 0.20; IR (liquid film): ν; 3450, 3030, 2940, 1602, 1590, 1495, 1450, 1380, 1250, 1175, 1080, 1040, 975 cm$^{-1}$; NMR (CDCl$_3$ + acetone-d$_6$ solution): δ; 7.45–6.75 (5H, m), 5.90–5.20 (6H, m), 4.63–4.34 (1H, m), 4.30–3.60 (6H, m), 2.90–2.55 (2H, m).

EXAMPLE 8

16-(3-Chlorophenoxy)-17,18,19,20-tetranorprosta-trans-2,cis-5,trans-13-triene-1,9α,11α,15α-tetrol[or 16-(3-chlorophenoxy)-17,18,19,20-tetranor-trans-Δ$^2$-PGF$_{2α}$alcohol]

83 mg. of 16-(3-chlorophenoxy)-17,18,19,20-tetranor-trans-Δ$^2$-PGF$_{2α}$methyl ester (which may be prepared as described in Example 6 or in Example 11 hereafter) were dissolved in 5 ml. of dry toluene and, after cooling to −78° C., 1.5 ml. of a 25(w/v)% solution of diisobutylaluminium hydride in toluene were added dropwise under an atmosphere of nitrogen with stirring. After stirring for 30 minutes at the same temperature, the reaction mixture was treated with 1 ml. of methanol in order to decompose the unreacted diisobutylaluminium hydride. The reaction mixture was then warmed to 0° C. and 3 ml. of water was added to the mixture, which as then stirred to separate a precipitate. The resulting precipitate was fitered off and the filtrate was diluted with ethyl acetate, washed with water and an aqueous solution of sodium chloride, dried over sodium sulphate and concentrated under reduced pressure. The residue was purified by column chromatography on silica gel using a mixture of ethyl acetate and cyclohexane (2:1) as eluent to give 46 mg. of the title compound and 21 mg. of the starting material. The title compound showed the following physical characteristics: TLC (developing solvent ethyl acetate); Rf = 0.17; IR (liquid film): ν; 3450, 3030, 2940, 1600, 1580, 1480, 1425, 1290, 1250, 1140, 975 cm$^{-1}$; NMR (CDCl$_3$ + acetone-d$_6$ solution): δ; 7.40–6.65 (4H, m), 5.90–5.20 (6H, m), 4.65–4.35 (1H, m), 4.30–3.63 (6H, m), 2.90–2.60 (2H, m).

REFERENCE EXAMPLE 9

2α-(6-Methyoxycarbonylhex-cis-2-enyl)-3β-hydroxymethyl-4α-(2-tetrahydropyranyloxy)-cyclopentan-1α-ol 40 g. of 2-oxa-3-hydroxy-6-syn-benzyloxymethyl-7-anti-(2-tetrahydropyranyloxy)-cis-bicyclo[3,3,0]octane [prepared as described in J. Org. Chem., 37, 2921 (1972)] were hydrogenated at 1 atm. in 800 ml. of methanol containing 14 g. of 5% palladium on charcoal for 1 hour at room temperature. After completion of the reaction, the catalyst was filtered off and the filtrate was concentrated under reduced pressure to give 39.4 g. of 2-oxa-3-hydroxy-6-syn-hydroxymethyl-7-anti-(2-tetrahydropyranyloxy)-cis-bicyclo[3,3,0]octane as a colourless oil having the following physical characteristics: TLC (developing solvent ethyl acetate): Rf = 0.25; IR (liquid film): ν; 3400, 2940-2860, 1465-1440, 1380, 1355, 1325, 1260, 1200, 1140, 1120, 1075, 1020 cm$^{-1}$;

2α-(6-Carboxyhex-cis-2-enyl)-3β-hydroxymethyl-4α-(2-tetrahydropyranyloxy)cyclopentan-1α-ol was prepared from 2-oxa-3-hydroxy-6-syn-hydroxymethyl-7-anti-(2-tetrahydropyranyloxy)-cis-bicyclo[3,3,0]octane (prepared as described above) using the procedure described in Reference Example 1.

2α-(6-Methoxycarbonylhex-cis-2-enyl)-3β-hydroxymethyl-4α-(2-tetrahydropyranyloxy)cyclopentan-1α-ol was prepared from 2α-(6-carboxyhex-cis-2-enyl)-3β-hydroxymethyl-4α-(2-tetrahydropyranyloxy)cyclopentan-1α-ol (prepared as described above) using the procedure described in Reference Example 1.

REFERENCE EXAMPLE 10

2α-(6-Methoxycarbonylhex-cis-2-enyl)-3β-acetoxymethyl-4α-(2-tetrahydropyranyloxy)cyclopentan-1α-ol 12 g. of 2α-(6-methoxycarbonylhex-cis-2-enyl)-3β-hydroxymethyl-4α-(2-tetrahydropyranyloxy)cyclopentan-1α-ol (prepared as described in Reference Example 9) were dissolved in a mixture of 60 ml. of anhydrous methylene chloride and 19 ml. of anhydrous pyridine. A solution of 3.2 g. of acetyl chloride in 40 ml. of methylene chloride was added dropwise at −20° to −30° C. over 1 hour. The reaction mixture was stirred at −30° C. for 45 minutes, and then 10 ml. of methanol and 40 g. of sodium bisulphate monohydrate were added successively. The yellow precipitate was filtered off and the filtrate was concentrated under reduced pressure to give 15 g. of the title compound having the following physical characteristics: TLC (developing solvent benzene - ethyl acetate = 2:1); Rf = 0.46; IR (liquid film): ν; 3500, 2950, 2850, 1740, 1440, 1370, 1250, 1150 cm$^{-1}$; NMR (CDCl$_3$ solution: δ; 5.70–5.23 (2H, m), 4.85–4.56 (1H, m), 4.40–3.34 (7H, m), 3.65 (3H, s), 2.05 (3H, s).

REFERENCE EXAMPLE 11

1α,4α-Bis(2-tetrahydropyranyloxy)-2α-(6-methoxycarbonylhex-cis-2-enyl)-3β-acetoxymethyl-cyclopentane 15 g. of 2α-(6-methoxycarbonylhex-cis-2-enyl)-3β-acetoxymethyl-4α-(2-tetrahydropyranyloxy)cyclopentan-1α-ol (prepared as described in Reference Example 10) were dissolved in 100 ml. of methylene chloride containing 81 mg. of p-toluenesulphonic acid and 5.0 g. of 2,3-dihydropyran. The reaction mixture was stirred for 10 minutes at room temperature, and then quenched with 10 ml. of pyridine. The mixture was diluted with ethyl acetate, washed with an aqueous solution of sodium bicarbonate and an aqueous solution of sodium chloride, dried over magnesium sulphate and concentrated under reduced pressure to give 17 g. of the title compound having the following physical characteristics: TLC (developing solvent benzene - ethyl acetate = 2:1); Rf = 0.67; IR (liquid film): ν; 2950, 2850, 1740, 1440, 1380, 1250, 1220, 1140, 1030 cm$^{-1}$.

REFERENCE EXAMPLE 12

1α,4α-Bis(2-tetrahydropyranyloxy)-2α-(6-methoxycarbonylhex-cis-2-enyl)-3β-hydroxymethyl-cyclopentane 17 g. of 1α,4α-bis(2-tetrahydropyranyloxy)-2α-(6-methoxycarbonylhex-cis-2-enyl)-3β-acetoxymethyl-cyclopentane (prepared as described in Reference Example 11) were stirred with 7.3 g. of anhydrous potassium carbonate in 120 ml. of anhydrous methanol for 30 minutes at room temperature. The reaction mixture was then acidified with acetic acid, diluted with ethyl acetate, washed with an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (2:1) as eluent to give 12 g. of the title compound having the following physical characteristics: TLC (developing solvent benzene — ethyl acetate = 2:1); Rf = 0.38; NMR (CCl$_4$ solution): δ; 5.59–5.15 (2H, m), 4.83–4.45 (2H, m), 4.33–2.90 (9H, m), 3.65 (3H, s).

REFERENCE EXAMPLE 13

1α,4α-Bis(2-tetrahydropyranyloxy)-2α-(6-phenylseleno-6-methoxycarbonylhex-cis-2-enyl)-3β-hydroxymethylcyclopentane A solution of 1.57 ml. of diisopropylamine in 45 ml. of dry tetrahydrofuran was cooled to −78° C., and to it 9.6 ml. of a 1.15M solution of n-butyllithium in n-hexane were added dropwise and stirred for 20 minutes at −78° C. to give lithiumdiisopropylamide. To the lithium diisopropylamide solution, 2 g. of 1α,4α-bis(2-tetrahydropyranyloxy)-2α-(6-methoxycarbonylhex-cis-2-enyl)-3β-hydroxymethyl-cyclopentane (prepared as described in Reference Example 12) in 15 ml. of dry tetrahydrofuran were added dropwise at −78° C. over 20 minutes and the reaction mixture stirred for 20 minutes at the same temperature. A solution of 2.84 g. of diphenyldiselenide in 10 ml. of tetrahydrofuran was added dropwise to the reaction mixture at −78° C. and stirring was continued at −78° C. for 40 minutes and at 0° C. for 20 minutes. The reaction mixture was poured into an aqueous solution of ammonium chloride and extracted with ethyl acetate. The extract was washed with an aqueous solution of sodium chloride, dried over magnesium sulphate and concentrated under reduced pressure. The residue was purified by column chromatography on silica gel using a mixture of ethyl acetate and benzene (1:4) as eluent to give 2.11 g. of the title compound having the following physical characteristics: TLC (developing solvent ethyl acetate - benzene = 1:2); Rf = 0.35; IR (liquid film): ν; 3450, 1735, 1580, 1440, 1140, 1030, 760 cm$^{-1}$; NMR (CDCl$_3$ solution): δ; 7.75–7.10 (5H, m), 5.70–5.05 (2H, m), 4.85–4.40 (2H, m), 3.62 (3H, s).

REFERENCE EXAMPLE 14

1α,4α-Bis(2-tetrahydropyranyloxy)-2α-(6-methoxycarbonylhexa-cis-2,trans-5-dienyl)-3β-hydroxymethyl-cyclopentane 1.24 g. of 1α,4α-bis(2-tetrahydropyranyloxy)-2α-(6-phenylseleno-6-methoxycarbonylhex-cis-2-enyl)-3β-hydroxymethyl-cyclopentane (prepared as described in Reference Example 13) were dissolved in 20 ml. of a mixture of ethyl acetate and methanol (3:2) and stirred with 1 ml. of 30% hydrogen peroxide at room temperature for one hour. The reaction mixture was diluted with ethyl acetate, washed with an aqueous solution of sodium bicarbonate and an aqueous solution of sodium chloride, dried over magnesium sulphate and concentrated under reduced pressure. The residue was purified by column chromatography on silica gel using a mixture of ethyl acetate and benzene (1:4) as eluent to give 610 mg. of the title compound having the following physical characteristics: TLC (developing solvent ethyl acetate - benzene = 1:2); Rf = 0.25; IR (liquid film): ν; 3450, 1735, 1660, 1440, 1030 cm$^{-1}$; NMR (CDCl$_3$ solution): δ; 696 (1H, dt), 5.82 (1H, d), 5.80–5.20 (2H, m), 4.85–4.45 (2H, m), 3.62 (3H, s), 3.15–2.80 (2H, m).

REFERENCE EXAMPLE 15

1α,4α-Bis(2-tetrahydropyranyloxy)-2α-(6-methoxycarbonylhexa-cis-2,trans-5-dienyl)-3β-formyl-cyclopentane 1.2 ml. of dimethylsulphide were added at −20° C. to a suspension of 910 mg. of N-chlorosuccinimide in 30 ml. of dry toluene and the reaction mixture was stirred for 1.5 hours. A solution of 600 mg. of 1α,4α-bis(2-tetrahydropyranloxy)-2α-(6-methoxycarbonylhexacis-2,trans-5-dienyl)-3β-hydroxymethyl-cyclopentane (prepared as described in Reference Example 14) in 15 ml. of toluene was added, and the reaction mixture was stirred for 2 hours at −20° C. After adding a solution of 1.7 ml. of triethylamine in 2.4 ml. of dry n-pentane, the reaction mixture was stirred for 10 minutes at room temperature. The mixture was extracted with ethyl acetate and the extract was washed with an aqueous solution of oxalic acid, an aqueous solution of sodium bicarbonate and an aqueous solution of sodium chloride, dried over magnesium sulphate and concentrated under reduced pressure. The residue was purified by column chromatography on silica gel using a mixture of ethyl acetate and benzene (1:6) as eluent to give 425 mg. of the title compound having the following physical characteristics: TLC (developing solvent ethyl acetate - benzene = 1:2); Rf = 0.62; IR (liquid film): $\nu$; 1725, 1660, 1440, 1280, 1030 cm$^{-1}$; NMR (CDCl$_3$ solution): $\delta$; 9.82–9.68 (1H, m), 7.22–6.78 (1H, m), 5.83 (1H, d), 5.65–5.30 (2H, m), 4.75–4.50 (2H, m), 3.72 (3H, s), 3.10–2.80 (2H, m).

REFERENCE EXAMPLE 16

Methyl 9α,11α-bis(2-tetrahydropyranyloxy)-15-oxo-16-phenoxy-17,18,19,20-tetranorprosta-trans-2,cis-5,trans-13-trienoate 72 mg. of sodium hydride (63% content) were suspended in 14 ml. of anhydrous tetrahydrofuran. With stirring under an atmosphere of nitrogen, 515 mg. of dimethyl 2-oxo-3-phenoxypropylphosphonate (prepared as described in Reference Example 3) in 2 ml. of tetrahydrofuran were added to the suspension at room temperature and the mixture strirred for 30 minutes. 410 mg. of 1α,4α-bis(2-tetrahydropyranyloxy)-2α-(6-methoxycarbonylhexa-cis-2, trans-5-dienyl)-3β-formyl-cyclopentane (prepared as described in Reference Example 15) in 2 ml. of tetrahydrofuran were added and the mixture stirred at 40°√ C. for 3 hours. The reaction mixture was then acidified with acetic acid, and silica gel was added to the mixture. The mixture was filtered, and the filtrate concentrated under reduced pressure. The residue was purified by column chromatography on silica gel using a mixture of benzene and ethyl acetate (8:1) as eluent to give 278 mg. of the title compound having the following physical characteristics:- TLC (developing solvent benzene - ethyl acetate = 2:1); Rf = 0.68; IR (liquid film): $\nu$; 1720, 1660, 1630, 1590, 1440, 1030 cm$^{-1}$; NMR (CDCl$_3$ solution): $\delta$; 7.55–6.30 (8H, m), 5.80 (1H, d), 5.70–5.20 (2H, m), 4.80–4.45 (4H, m), 3.72 (3H, s).

EXAMPLE 9

Methyl 9α,11α-bis(2-tetrahydropyranyloxy)-15ε-hydroxy-16-phenoxy17,18,19,20-tetranorprosta-trans-2,cis-5,trans-13-trienoate To a solution of 278 mg. of methyl 9α,11α-bis-(2-tetrahydropyranyloxy)-15-oxo-16-phenoxy-17,18,19,20-tetranorprosta-trans-2,cis-5,trans-13-trienoate (prepared as described in Reference Example 16) in 5ml. of methanol, there were added carefully 57 mg. of sodium borohydride whilst keeping the temperature at −40° C. After 30 minutes, the mixture was neutralized with acetic acid and concentrated under reduced pressure. The residue was diluted with ethyl acetate, washed with an aqueous solution of sodium bicarbonate and an aqueous solution of sodium chloride, dried over magnesium sulphate and concentrated under reduced pressure to give 279 mg. of the title compound having the following physical characteristics:- TLC (developing solvent benzene — ethyl acetate = 2:1); Rf = 0.44 and 0.48; IR (liquid film):$\nu$; 3450, 1730, 1660, 1590, 1440, 1030 cm$^{-1}$; NMR (CDCl$_3$ solution): $\delta$; 7.50–6.65 (6H, m), 6.10–5.25 (5H, m), 4.80–4.50 (3H, m), 3.72 (3H, s).

EXAMPLE 10

Methyl 9α,11α,15α-trihydroxy-16-phenoxy-17,18,19,20-tetranorprosta-trans-2,cis-5,trans-13-trienoate [or 16-phenoxy-17,18,19,20-tetranor-trans-$\Delta^2$-PGF$_{2\alpha}$-methyl ester]

A solution of 279 mg. of methyl 9α,11α-bis(2-tetrahydropyranyloxy)-15ξ-hydroxy-16-phenoxy-17,18,19,20-tetranorprosta-trans-2,cis-5,trans-13-trienoate (prepared as described in Example 9) in 5 ml. of tetrahydrofuran was stirred with 1.5 ml. of 1N hydrochloric acid at room temperature for 3 hours. The reaction mixture was then poured into water, extracted with ethyl acetate and the extract was washed with water, an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (1:2) as eluent to give 74 mg. of the title compound and 66 mg. of its 15β-hydroxy isomer. The title compound showed the following physical characteristics:- TLC (developing solvent ethyl acetate); Rf = 0.30; (15β-hydroxy isomer : Rf = 0.36); IR (liquid film): $\nu$; 3400, 3020, 2940, 1725, 1655, 1600, 1590, 1495, 1435, 1335, 1280, 1250, 1175, 1080, 1045, 975 cm$^{-1}$; NMR (CDCl$_3$ solution): $\delta$ ; 7.45–6.66 (6H, m), 5.96–5.20 (5H, m), 4.63–4.35 (1H, m), 4.25–3.78 (4H, m), 3.69 (3H, s), 2.95 (2H, t).

EXAMPLE 11

Methyl 9α,11α,15α-trihydroxy-16-(3-chlorophenoxy)-17,18,19,20-tetranorprosta-trans-2,cis-5,trans-13-trienoate [or 16-(3-chlorophenoxy)-17,18,19,20-tetranor-trans-$\Delta^2$-PGF$_{2\alpha}$ methyl ester]

Following the procedures described in Reference Example 16 and in Examples 9 and 10, but using dimethyl 2-oxo-3-(3-chlorophenoxy)propylphosphonate (prepared as described in Reference Example 6) instead of dimethyl 2-oxo-3-phenoxypropylphosphonate in Reference Example 16 there was obtained the title compound having the following physical characteristics:- TLC (developing solvent ethyl acetate); Rf = 0.32; (15β-hydroxy isomer : Rf = 0.38); IR (liquid film): ν ; 3400, 3030, 2940, 1720, 1655, 1600, 1580, 1480, 1435, 1335, 1290, 1175, 1040, 975 cm$^{-1}$; NMR (CDCl$_3$ solution): δ ; 7.40–6.60 (5H, m), 5.97–5.20 (5H m), 4.64–4.33 (1H, m), 4.30–3.79 (4H, m), 3.69 (3H, s), 2.95 (2H, t).

EXAMPLE 12

Methyl 9α,11α,15α-trihydroxy-16-(3-trifluoromethylphenoxy)-17,18,19,20-tetranorprosta-trans-2,cis-5,trans-13-trienoate [or 16-(3-trifluoromethylphenoxy)-17,18,19,20-tetranor-trans-Δ$^2$-PGF$_{2α}$ methyl ester]

Following the procedures described in Reference Example 16 and in Examples 9 and 10, but using dimethyl 2-oxo-3-(3-trifluoromethylphenoxy)propylphosphonate (prepared as described in Reference Example 1) instead of dimethyl 2-oxo-3-phenoxypropylphosphonate in Reference Example 16 there was obtained the title compound having the following physical characteristics:- TLC (developing solvent ethyl acetate): Rf = 0.23; (15β-hydroxy isomer : Rf = 0.30); IR (liquid film): ν ; 3350, 2900, 1720, 1660, 1600, 1500, 980 cm$^{-1}$; NMR (CDCl$_3$ solution): δ ; 7.50–7.08 (4H, m), 6.42 (1H, dt ), 5.80 (1H, d), 5.77–5.60 (2H, m), 5.60–5.20 (2H, m), 4.65–4.35 (1H, m).

REFERENCE EXAMPLE 17

1α,4α-Bis(2-tetrahydropyranyloxy)-2α-(6-phenyl-seleno-6-methoxycarbonylhex-cis-2-enyl)-3β-(3-hydroxyprop-trans-1-enyl)cyclopentane By proceeding as described in Reference Example 5 but replacing the methyl 9α,11α,15α-tris(2-tetrahydropyranyloxy)-16-phenoxy-17,18,19,20-tetranorprosta-cis-5,-trans-13-dienote by 7.06 g. of 1α,4α-bis(2-tetrahydropyranyloxy)-2α-(6-methoxycarbonylhex-cis-2-enyl)-3β-(3-hydroxyprop-trans-1-enyl)cyclopentane dissolved in 50 ml. of tetrahydrofuran and utilizing a solution of 5.41 ml. of diisopropylamine in 150 ml. of tetrahydrofuran, 31.6 ml. of a 1.2M solution of n-butyllithium in n-hexane and a solution of 9.36 g. of diphenyldiselenide in 50 ml. of tetrahydrofuran, there were obtained 7.73 g. of the title compound having the following physical characteristic:- TLC (developing solvent, benzene-ethyl acetate = 2:1); Rf = 0.35.

1α,4α-Bis(2-tetrahydropyranyloxy)-2α-(6-methoxycarbonylhex-cis-2-enyl)-3β-(3-hydroxyprop-trans-1-enyl)-cyclopentane, used as a starting material in the above procedure, was prepared as follows:-

1.

2-Oxa-3-oxo-6-syn-(2-methoxycarbonyl-trans-vinyl)-7-anti-acetoxy-cis-bicyclo[3,3,0]octane Under an atmosphere of nitrogen and at laboratory temperature, 140 ml. of absolute methylene chloride and 16.1 ml. of absolute pyridine were stirred with 10 g. of chromium trioxide for 30 minutes. 20 g. of infusorial earth were then added to the solution. After cooling the temperature to 0° C., 2.14 g. of 2-oxa-3-oxo-6-synhydroxymethyl-7-anti-acetoxy-cis-bicyclo[3,3,0]octane [prepared as described in J. Amer. Chem. Soc., 92, 397 (1970)]in 20 ml. of methylene chloride were added and stirred for 15 minutes at 0° C. The reaction mixture was then treated with 25 g. of sodium bisulphate and stirred for a further 10 minutes at 0° C. and filtered through a pad of magnesium sulphate. The filtrate was concentrated under reduced pressure below 0° C. to give 2-oxa-3-oxo-6-syn-formyl-7-anti-acetoxy-cis-bicyclo-[3,3,0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in C.R. Acad. Sci. Paris Ser. A,B, 262B, 515 (1966)] were added to the suspension, and the mixture was stirred for 30 minutes. The formyl compound, obtained above, in 30 ml. of tetrahydrofuran, was added, whilst maintaining the temperature below 15° C., and the mixture was stirred for 2 hours at 15° C. Then the reaction mixture was treated with 2 ml. of acetic acid to pH 5 and concentrated slightly. The product was treated with 20 ml. of water and extracted twice with 80 ml. of ethyl acetate (total volume 160 ml.). The organic layer was washed with an aqueous solution of sodium chloride, dried over magnesium sulphate and concentrated under reduced pressure. The residue was purified by column chromatography on silica gel using a mixture of ethyl acetate and benzene (1:4) as eluent to give 2.0 g. of 2oxa-3-oxo-6-syn-(2-methoxycarbonyl-trans-vinyl)-7-anti-acetoxy-cis-bicyclo[3,3,0]octane having the following physical characteristics: TLC (developing solvent, ethyl acetate-benzene = 1:2); Rf = 0.38; IR (liquid film): ν; 2970, 1775, 1735, 1710, 1650, 1240, 1160, 1037, 980 cm$^{-1}$; NMR (CDCl$_3$ solution): δ; 6.77 (1H, d), 5.87 (1H, d), 5.00 (2H, m), 3.70 (3H, s), 3.0–1.9 (6H, m), 2.04 (3H, s).

2.

2-Oxa-3-oxo-6-syn-(2-methoxycarbonyl-trans-vinyl)-7-anti-hydroxy-cis-bicyclo[3,3,0]octane 2.68 g. of 2-oxa-3-oxo-6-syn-(2-methoxycarbonyl-trans-vinyl)-7-anti-acetoxy-cis-bicyclo[3,3,0]octane (prepared as described above) in 30 ml. of absolute methanol and 1.38 g. of potassium carbonate were stirred at room temperature for 15 minutes, successively cooled in an ice-bath and neutralized with 20 ml. of 1N hydrochloric acid. 260 ml. of ethyl acetate and 27 ml. of an aqueous solution of sodium bicarbonate were added to the reaction mixture which separated into two layers. The organic layer was washed with an aqueous solution of sodium chloride, dried over magnesium sulphate and concentrated under reduced pressure to give 1.96 g. of 2-oxa-3-oxo-6-syn-(2-methoxycarbonyl-trans-vinyl)-7-anti-hydroxy-cis-bicyclo[3,3,0]octane having the following physical characteristics: TLC (developing solvent, methylene chloride-methanol = 19:1); Rf = 0.38; IR (liquid film): ν; 3430, 1786–1690 (broad), 1650 cm$^{-1}$; NMR (CDCl$_3$ solution); δ; 6.82 (1H, dd), 5.90 (1H, d), 4.95 (1H, m), 3.72 (3H, s), 4.30–3.25 (2H, m), 2.90–1.70 (6H, m).

3.

2-Oxa-3-oxo-6-syn-(2-methoxycarbonyl-trans-vinyl)-7-anti-(2-tetrahydropyranyloxy)-cis-bicyclo[3,3,0]octane 2.31 g. of 2-oxa-3-oxo-6-syn-(2-methoxycarbonyl-trans-vinyl)-7-anti-hydroxy-cis-bicyclo[3,3,0]octane (prepared as described above) were dissolved in 30 ml. of methylene chloride and the solution stirred with 20 mg. of p-toluenesulphonic acid and 3 ml. of 2,3-dihydropyran for 15 minutes at room temperature. The reaction mixture was neutralized with an aqueous solution of sodium bicarbonate, diluted with ethyl acetate, washed with an aqueous solution of sodium chloride, dried over magnesium sulphate and concentrated under reduced pressure. The residue was purified by column chromatography on silica gel using a mixture of ethyl acetate and benzene (1:3) as eluent to give 3.0 g. of 2-oxa-3-oxo-6-syn-(2-methoxy-carbonyl-trans-vinyl)-7-anti-(2-tetrahydropyranyloxy)-cis-bicyclo[3,3,0]octane having the following physical characteristics: TLC (developing solvent, ethyl acetate-benzene = 1:2); Rf = 0.34; IR (KBr tablet): $\nu$; 2930, 1770, 1710, 1650, 1343, 1240, 1152 cm$^{-1}$; NMR (CDCl$_3$ solution): $\delta$ ; 6.78 (1H, $dd$), 5.84 (1H, $d$), 4.97 (1H, $m$), 4.63 (1H, $m$), 3.71 (3H, $s$), 4.30–3.20 (3H, $m$).

4

2-Oxa-3-hydroxy-6-syn-(3-hydroxyprop-trans-1-enyl)-7-anti-(2-tetrahydropyranyloxy)-cis-bicyclo[3,3,0]octane

3.10 g. of 2-oxa-3-oxo-6-syn-(2-methoxycarbonyl-trans-vinyl)-7-anti-(2-tetrahydropyranyloxy)-cis-bicyclo-[3,3,0]octane (prepared as described above) were dissolved in 100 ml. of toluene and the solution was cooled to −65° C. To the solution, 23 ml. of a 25(w/v)% solution of diisobutylaluminium hydride in toluene were added and the mixture was stirred for 20 minutes at −60° C. Aqueous methanol was then added to decompose excess diisobutylaluminium hydride. The precipitate was filtered off and the filtrate was dried and concentrated under reduced pressure to give 2.8 g. of 2-oxa-3-hydroxy-6-syn-(3- hydroxyprop-trans-1-enyl)-7-anti-(2-tetrahydropyranyloxy)-cis-bicyclo[3,3,0]octane having the following physical characteristics: TLC (developing solvent, methylene chloride-methanol = 19:1); RF = 0.23; IR (liquid film): $\nu$; 3390, 2930, 1350, 1120 cm$^{-1}$; NMR (CDCl$_3$ solution): $\delta$; 5.75–5.15 (3H, $m$), 4.75–3.34 (8H, $m$).

5.

2$\alpha$-(6-Methoxycarbonylhex-cis-2-enyl)-3$\beta$-(3-hydroxyprop-trans-1-enyl)-4$\alpha$-(2-tetrahydropyranyloxy)cyclopentan-1$\alpha$-ol

2.94 g. of sodium hydride (65% content) were suspended in 40 ml. of dimethyl sulphoxide and the suspension was stirred with heating at 65° C. for 40 minutes to obtain sodium methylsulphinylmethylide. The reaction mixture was allowed to cool to room temperature and was then added dropwise to a solution of 18.5 g. of (4-carboxybutyl)triphenylphosphonium bromide in 40 ml. of dimethyl sulphoxide, the reaction temperature being kept within the range of 20° to 25° C.

A solution of 2.84 g. of 2-oxa-3-hydroxy-6-syn-(3-hydroxyprop-trans-1-enyl)-7-anti-(2-tetrahydropyranyloxy)-cis-bicyclo[3,3,0]octane (prepared as described above) in 40 ml. of dimethyl sulphoxide was added, and the mixture stirred vigorously at 25° C. for 1 hour. The reaction mixture was poured into 500 ml. of ice-water and neutral substances were removed by extraction with a mixture of ethyl acetate and diethyl ether (1:1). The aqueous layer was acidified to pH 3 with a saturated aqueous solution of oxalic acid and extracted with a mixture of diethyl ether and ethyl acetate (1:1). The extract was washed with water, dried over magnesium sulphate and concentrated under reduced pressure to give crude 2$\alpha$-(6-carboxyhex-cis-2-enyl)-3$\beta$-(3-hydroxyprop-trans-1-enyl)-4$\alpha$-(2-tetrahydropyranyloxy)cyclopentan-1$\alpha$-ol having the following physical characteristics: TLC (developing solvent, methylene chloride-methanol = 19:1); Rf = 0.23; IR (liquid film): $\nu$; 2930, 1720, 1240, 1120 cm$^{-1}$; NMR (CDCl$_3$ solution): $\delta$; 5.70–5.25 (4H, $m$), 4.62 (1H, $m$).

The crude acid compound thus obtained was dissolved in 40 ml. of methylene chloride, the solution was cooled to 0° C. and a solution of diazomethane in diethyl ether was added until the reaction mixture was coloured pale yellow. The reaction mixture was then concentrated under reduced pressure and the residue was subjected to column chromatography on silica gel using a mixture of ethyl acetate and cyclohexane (1:1) as eluent to give 2.87 g. of 2$\alpha$-(6-methoxycarbonylhex-cis-2-enyl)-3$\beta$-(3-hydroxyprop-trans-1-enyl)-4$\alpha$-(2-tetrahydropyranyloxy)cyclopentan-1$\alpha$-ol having the following physical characteristics: TLC (developing solvent, ethyl acetate-cyclohexane = 2:1); Rf = 0.31; IR (liquid film): $\nu$; 3420, 2930, 1740, 1435, 1020 cm$^{-1}$; NMR (CDCl$_3$ solution): $\delta$; 5.75 – 5.20 (4H, $m$), 4.67 (1H, $m$), 4.20–3.30 (6H, $m$), 3.67 (3H, $s$).

6.

2$\alpha$-(6-Methoxycarbonylhex-cis-2-enyl)-3$\beta$-(3-acetoxyprop-trans-1-enyl)-4$\alpha$-(2-tetrahydropyranyloxy)cyclopentan-1$\alpha$-ol

By proceeding as described in Reference Example 10 but replacing the 2$\alpha$-(6-methoxycarbonylhex-cis-2-enyl)-3$\beta$-hydroxymethyl-4$\alpha$-(2-tetrahydropyranyloxy)-cyclopentan-1$\alpha$ol by 14 g. of 2$\alpha$-(6methoxycarbonylhex-cis-2-enyl)-3$\beta$-(3-hydroxyprop-trans-1-enyl)-4$\alpha$-(2-tetrahydropyranyloxy)-cyclopentan-1$\alpha$-ol (prepared as described above) dissolved in a mixture of 200 ml. of anhydrous methylene chloride and 20 ml. of anhydrous pyridine and utilizing a solution of 2.85 ml. of acetyl chloride in 50 ml. of methylene chloride, there were obtained 12.6 g. of 2$\alpha$-(6-methoxy-carbonylhex-cis-2-enyl)-3$\beta$-(3-acetoxyprop-trans-1-enyl)-4$\alpha$-(2-tetrahydropyranyloxy)cyclopentan-1$\alpha$-ol having the following physical characteristics: TLC (developing solvent, benzene-ethyl acetate = 1:1); Rf = 0.64; IR (liquid film): $\nu$; 3450, 1740, 1440, 1240, 1030, 980 cm$^{-1}$; NMR (CDCl$_3$ solution): $\delta$; 5.80–5.20 (4H, $m$), 4.75–4.45 (2H, $m$), 4.35–3.95 (2H, $m$), 3.76 (3H, $s$), 2.03 (3H, $s$).

7.

1$\alpha$,4$\alpha$-Bis(2-tetrahydropyranyloxy)-2$\alpha$-(6-methoxycarbonylhex-cis-2-enyl)-3$\beta$-(3-acetoxyprop-trans-1-enyl)-cyclopentane

By proceeding as described in Reference Example 11 but replacing the 2$\alpha$-(6-methoxycarbonylhex-cis-2-enyl)-3$\beta$-acetoxymethyl-4$\alpha$-(2-tetrahydropyranyloxy)-cyclopentan-1$\alpha$-ol by 7.9 g. of 2$\alpha$-(6-methoxycarbonylhex-cis-2-enyl)-3$\beta$-(3-acetoxyprop-trans-1-enyl)-4$\alpha$-(2-tetrahydropyranyloxy)-cyclopentan-1$\alpha$-ol (prepared as described above) dissolved in 150 ml. of methylene chloride and utilizing 50 mg. of p-toluenesulphonic acid and 2.8 ml. of 2,3-dihydropyran, there were obtained 9.4 g. of 1$\alpha$,4$\alpha$-bis(2-tetrahydro-pyranyloxy)-2$\alpha$-(6-methoxycarbonylhex-cis-2-enyl)-3$\beta$-(3-acetoxyprop-trans-1-enyl)cyclopentane having the following physical characteristic: TLC (developing solvent, benzene-ethyl acetate = 2:1); Rf = 0.60.

8. 1$\alpha$,4$\alpha$-Bis(2-tetrahydropyranyloxy)-2$\alpha$-(6-methoxy-carbonylhex-cis-2-enyl)-3$\beta$-(3-hydroxyprop-trans-1-enyl)-cyclopentane By proceeding as described in Reference Example 12 but replacing the 1$\alpha$,4$\alpha$-bis(2-tetrahydropyranyloxy)-2$\alpha$-(6-methoxycarbonylhex-cis-2-enyl)-3$\beta$-acetoxymethyl-cyclopentane by 9.4 g. of 1α,4α-bis(2-tetrahydropyranyloxy)-2α-(6-methoxycarbonylhex-cis-2-enyl)-3β-(3-acetoxyprop-trans-1-enyl)cyclopentane (prepared as described above) dissolved in 150 ml. of methanol and utilizing 3.9 g. of anhydrous potassium carbonate, there were obtained 7.1 g. of 1α,4α-bis(2-tetrahydropyranyloxy)-2α-(6-methoxycarbonylhex-cis-2-enyl)-3β-(3-hydroxyprop-trans-1-enyl)cyclopentane having the following physical characteristics: TLC (developing solvent, benzene-ethyl acetate = 2:1); Rf = 0.22; IR (liquid film): ν; 3450, 1740, 1440, 1030, 980 cm$^{-1}$; NMR (CDCl$_3$ solution): δ; 6.00–5.20 (4H, m), 5.00–4.55 (2H, m), 3.76 (3H, s).

REFERENCE EXAMPLE 18

1α,4α-Bis(2-tetrahydropyranyloxy)-2α-(6-methoxycarbonyl-hexa-cis-2,trans-5-dienyl)-3β-(3-hydroxyprop-trans-1-enyl)-cyclopentane By proceeding as described in Example 3 but replacing the methyl 2-phenylseleno-9α,11α,15α-tris(2-tetrahydropyranyloxy)-16-phenoxy-17,18,19,20-tetranorprosta-cis-5,trans-13-dienoate by 7.73 g. of 1α,4α-bis(2-tetrahydropyranyloxy)-2α-(6-phenylseleno-6-methoxy-carbonylhex-cis-2-enyl)-3β-(3-hydroxyprop-trans-1-enyl)-cyclopentane (prepared as described in Reference Example 17) dissolved in 120 ml. of a mixture of ethyl acetate and tetrahydrofuran (2:1) and utilizing 2.5 g. of sodium bicarbonate and 3.2 ml. of 30% hydrogen peroxide, there were obtained 5.74 g. of the title compound having the following physical characteristics: TLC (developing solvent, benzene-ethyl acetate + 2:1); Rf = 0.25; IR (liquid film): ν; 3450, 1730, 1660, 1440, 1030 cm$^{-1}$; NMR (CDCl$_3$ solution): δ; 7.32–6.75 (1H, m), 6.15–5.30 (5H, m), 4.90–4.50(2H, m), 3.76 (3H, s), 3.15–2.80 (2H, m).

REFERENCE EXAMPLE 19

1α,4α-Bis(2-tetrahydropyranyloxy)-2α-(6-methoxycarbonylhexa-cis-2,trans-5-dienyl)-3β-(2-formyl-trans-vinyl)cyclopentane To a solution of 5.74 g. of 1α,4α-bis(2-tetrahydropyranyloxy)-2α-(6-methoxycarbonylhexa-cis-2,trans-5-dienyl)-3β-(3-hydroxyprop-trans-1-enyl)cyclopentane (prepared as described in Reference Example 18) in 130 ml. of methylene chloride were added 40 g. of manganese dioxide and the mixture was stirred at room temperature for 2 hours. The reaction mixture was filtered and the filtrate was concentrated under reduced pressure. The residue was purified by column chromatography on silica gel using a mixture of benzene and ethyl acetate (4:1) as eluent to give 3.85 g. of the title compound having the following physical characteristics: TLC (developing solvent, benzene-ethyl acetate = 2:1); Rf = 0.50; IR (liquid film): 1730, 1690, 1660, 1440, 1030, 980, 760 cm$^{-1}$; NMR (CDCl$_3$ solution): δ; 9.72 (1H, d), 7.40–5.35 (6H, m), 4.90–4.50 (2H, m), 3.80 (3H, s).

EXAMPLE 13

Methyl 9α,11α-bis(2-tetrahydropyranyloxy)-15ξ-hydroxy-16-phenylthio-17,18,19,20-tetranorprosta-trans-2,cis-5,trans-13-trienoate To a solution of 1.17 ml. of thioanisole in 20 ml. of dry tetrahydrofuran were added 8.4 ml. of a 1.2M solution of n-butyllithium in n-hexane at −20° C. and the mixture was stirred at the same temperature of 1.5 hours to give a 0.28M solution of phenylthiomethyllithium in tetrahydrofuran.

To a solution of 980 mg. of 1α,4α-bis(2-tetrahydropyranyloxy)-2α-(6-methoxycarbonylhexa-cis-2,trans-5-dienyl)-3β-(2-formyl-trans-vinyl)cyclopentane (prepared as described in Reference Example 19) in 18 ml. of dry tetrahydrofuran were added 8.4 ml. of a 0.28M solution of phenylthiomethyllithium (prepared as described above) in tetrahydrofuran at −70° C. and the mixture was stirred at the same temperature for 1 hour. The reaction mixture was quenched with 0.3 ml. of acetic acid, poured into a saturated aqueous solution of ammonium chloride and extracted with ethyl acetate. The extract was washed with an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (4:1) as eluent to give 740 mg. of the title compound having the following physical characteristics:- TLC (developing solvent, benzene-ethyl acetate = 2:1); Rf = 0.48; IR (liquid film): ν; 3450, 1740, 1660, 1590, 1480, 1030 cm$^{-1}$; NMR (CDCl$_3$ solution): δ ; 7.55–6.70 (6H, m), 6.10–5.25 (5H, m), 4.82–4.45 (2H, m), 3.72 (3H, s).

EXAMPLE 14

Methyl 9α,11α,15α-trihydroxy-16-phenylthio-17,18,19,20-tetranorprosta-trans-2,cis-5,trans-13-trienoate [or 16-phenylthio-17,18,19,20-tetranor-trans-Δ$^2$-PGF$_{2α}$ methyl ester]

To a solution of 740 mg. of methyl 9α,11α-bis(2-tetrahydropyranyloxy)-15ξ-hydroxy-16-phenylthio-17,18,19,20 -tetranorprosta-trans-2,cis-5,trans-13-trienoate (prepared as described in Example 13) in 12 ml. of tetrahydrofuran were added 4 ml. of 1N hydrochloric acid and the mixture was stirred at 35° C. for 4 hours. The reaction mixture was extracted with ethyl acetate and the extract was washed with an aqueous solution of sodium bicarbonate, water and an aqueous solution of sodium chloride, dried over magnesium sulphate and concentrated under reduced pressure. The residue was purified by column chromatography on silica gel using a mixture of benzene and ethyl acetate (2:3) as eluent to give 150 mg. of the title compound, 120 mg. of its 15β-hydroxy isomer and 125 mg. of their mixture. The title compound showed the following physical characteristics:- TLC (developing solvent, ethyl acetate); Rf = 0.15, (15β-hydroxy isomer : Rf = 0.23); IR (liquid film): ν; 3400, 1730, 1660, 1590, 1480, 980, 750 cm$^{-1}$; NMR (CDCl$_3$ solution): δ ; 7.45–7.07 (5H, m), 6.95 (1H, dt), 5.82 (1H, d), 5.70–5.30 (4H, m), 4.30–3.80 (3H, m), 3.70 (3H, s), 3.06 (2H, d).

REFERENCE EXAMPLE 20

Methyl 9α,11α-bis(2-tetrahydropyranyloxy)-15-oxo-16-(3-chlorophenoxy-17,18,19,20-tetranorprosta-trans-2,cis-5,trans-13-trienoate By processing as described in Reference Example 16 but replacing the dimethyl 2-oxo-3-phenoxypropylphosphonate by 585 mg. of dimethyl 2-oxo-3-(3-chlorophenoxy)propylphosphonate (prepared as described in Reference Example 6) dissolved in 8 ml. of dry tetrahydrofuran and utilizing a suspension of 54 mg. of sodium hydride (63% content) in 30 ml. of dry tetrahydrofuran and a solution of 390 mg. of 1α,4α-bis(2-tetrahydropyranyloxy)-2α-(6-methoxycarbonylhexa-cis-2,trans-5-dienyl)-3β-formylcyclopentane (prepared as described in Reference Example 15) in 5 ml. of dry tetrahydrofuran, there were obtained 420 mg. of the title compound having the following physical characteristics:- TLC (developing solvent, benzene-ethyl acetate = 2:1); Rf = 0.60; IR (liquid film):ν; 3020, 2950, 2870, 1730, 1700–1680, 1655, 1620, 1595, 1580, 1475, 1435, 1035, 1020, 980 cm$^{-1}$; NMR (CCl$_4$ solution): δ ; 7.4–5.1 (10H, m), 4.7–4.4 (4H, m), 3.6 (3H, s).

EXAMPLE 15

Methyl 9α,11α-bis(2-tetrahydropyranyloxy)-15ξ-hydroxy-16-(3-chlorophenoxy)-17,18,19,20-tetranorprosta-trans-2,cis-5,trans-13-trienoate By proceeding as described in Example 9 but replacing the methyl 9α,11α-bis(2-tetrahydropyranyloxy)-15-oxo-16-phenoxy-17,18,19,20-tetranorprosta-trans-2,cis-5,trans-13-trienoate by 420 mg. of methyl 9α,11α-bis(2-tetrahydropyranyloxy)-15-oxo-16-(3-chlorophenoxy)-17,18,19,20-tetranorprosta-trans-2,cis-5,trans-13-trienoate (prepared as described in Reference Example 20) dissolved in 15 ml. of methanol and utilizing 110 mg. of sodium borohydride, there were obtained 270 mg. of the title compound having the following physical characteristics:- TLC (developing solvent, benzene-ethyl acetate = 2:1); Rf = 0.36 and 0.42; IR (liquid film):ν; 3600–3100, 2950, 2870, 1725, 1650, 1595, 1580, 1435, 1030–1020, 980 cm$^{-1}$; NMR (CDCl$_3$ solution): δ ; 7.3–6.6 (5H, m), 6.05–5.1 (5H, m), 4.8–4.4 (2H, m), 3.66 (3H, s).

EXAMPLE 16

Methyl 9α,11α,15α-trihydroxy-16-(3-chlorophenoxy)-17,18,19,20-tetranorprosta-trans-2,cis-5,trans-13-trienoate [or 16-(3-chlorophenoxy)-17,18,19,20-tetranor-trans-Δ$^2$-PGF$_{2α}$methyl ester By proceeding as described in Example 4 but replacing the methyl 9α,11α,15α-tris(2-tetrahydropyranloxy)-16-phenoxy-17,18,19,20-tetranorprosta-trans-2,cis-5,trans-13-trienoate by 270 mg. of methyl 9α,11α-bis(2-tetrahydropyranloxy)-15ξ-hydroxy-16-(3-chlorophenoxy)-17,18,19,20-tetranorprosta-trans-2,cis-5,trans-13-trienoate (prepared as described in Example 15) dissolved in a mixture of 1 ml. of tetrahydrofuran and 10 ml. of 65% aqueous acetic acid, there were obtained 80 mg. of the title compound and 40 mg. of its 15β-hydroxy isomer. The title compound showed the same physical characteristics as those of the product of Example 6.

REFERENCE EXAMPLE 21

Methyl 9α,15α-dihydroxy-11α-(2-tetrahydropyranyloxy)-16-(4-chlorophenoxy)-17,18,19,20-tetranorprosta-cis-5,trans-13-dienoate By proceeding as described in Reference Example 3 but replacing the methyl 9α-acetoxy-11α-(2-tetrahydropyranyloxy)-15α-hydroxy-16-phenoxy-17,18,19,20-tetranorprosta-cis-5,trans-13-dienoate by 379 mg. of methyl 9α-acetoxy-11α-(2-tetrahydropyranyloxy)-15α-hydroxy-16-(4-chlorophenoxy)-17,18,19,20-tetranorprosta-cis-5,trans-13-dienoate (prepared as described hereafter) dissolved in 4 ml. of methanol and utilizing 145 mg. of potassium carbonate, there were obtained 303 mg. of the title compound having the following physical characteristic:- TLC (developing solvent, methylene chloride-methanol = 20:1); Rf = 0.32.

Methyl 9α-acetoxy-11α-(2-tetrahydropyranyloxy)-15α-hydroxy-16-(4-chlorophenoxy)-17,18,19,20-tetranorprosta-cis-5,trans-13-dienoate, used as a starting material in the above procedure, was prepared as follows.

1. Dimethyl 2-oxo-3-(4-chlorophenoxy)propylphosphonate

By proceeding as described in Reference Example 3 but replacing the ethyl phenoxyacetate by 10 g. of ethyl (4-chlorophenoxy)acetate (prepared as described in Beil. 6, 187) dissolved in 60 ml. of tetrahydrofuran and utilizing a solution of 11.9 g. of dimethyl methylphosphonate in 67 ml. of tetrahydrofuran and 63 ml. of a 1.5M solution of n-butyllithium in n-hexane, there were obtained 12 g. of dimethyl 2-oxo-3-(4-chlorophenoxy)-phosphonate having the following physical characteristics:- boiling point = 150°–180° C./0.06 mmHg; NMR (CDCl$_3$ solution): δ ; 7.35–6.70 (4H, m), 4.68 (2H, s), 3.70 (6H, d), 3.15 (2H, d).

2. Methyl 9α-acetoxy-11α-(2-tetrahydropyranyloxy)-15-oxo-16-(4-chlorophenoxy)-17,18,19,20-tetranorprosta-cis-5,trans-13-dienoate.

By proceeding as described in Reference Example 3 but replacing the dimethyl 2-oxo-3-phenoxypropylphosphonate by 11.125 g. of dimethyl 2-oxo-3-(4-chlorophenoxy)-propylphosphonate (prepared as described above) dissolved in 25 ml. of tetrahydrofuran and utilizing a suspension of 960 mg. of sodium hydride (63% content) in 150 ml. of tetrahydrofuran and a solution of 5.0 g. of 1α-acetoxy-2α-(6-methoxycarbonylhex-cis-2-enyl)-3β-formyl-4α-(2-tetrahydropyranyloxy)cyclopentane (prepared as described in Reference Example 1), there were obtained 4.53 g. of methyl 9α-acetoxy-11α-(2-tetrahydropyranyloxy)-15-oxo-16-(4-chlorophenoxy)-17,18,19,20-tetranorprosta-cis-5,trans-13-dienoate having the following physical characteristics- TLC (developing solvent, benzene-ethyl acetate = 2:1); Rf = 0.66; IR (liquid film):ν; 3400, 2940, 2850, 1735, 1700, 1625, 1600, 1595, 1495, 1440, 1380 cm$^{-1}$; NMR (CDCl$_3$ solution): δ ; 7.50–6.30 (6H, m), 5.50–4.90 (3H, m), 4.75–4.35 (3H, m), 4.30–3.00 (6 H, m).

3. Methyl 9α-acetoxy-11α-(2-tetrahydropyranyloxy)-15α-hydroxy-16-(4-chlorophenoxy)-17,18,19,20-tetranorprostacis-5,trans-13-dienoate By proceeding as described in Reference Example 3 but replacing the methyl 9α-acetoxy-11α-(2-tetrahydropyranyloxy)-15-oxo-16-phenoxy-17,18,19,20-tetranorprosta-cis-5,trans-13-dienoate by 4.53 g. of methyl 9α-acetoxy-11α-(2-tetrahydropyranyloxy)-15-oxo-16-(4chlorophenoxy)-17,18,19,20-tetranorprosta-cis-5,trans-13-dienoate (prepared as described above) dissolved in a mixture of 40 ml. of methanol and 10 ml. of tetrahydrofuran and utilizing 915 mg. of sodium borohydride, there were obtained 1.1 g. of methyl 9α-acetoxy-11α(2-tetrahydropyranyloxy)-15α-hydroxy-16-(4-chlorophenoxy)-17,18,19,20-tetranorprosta-cis-5,trans-13-dienoate, 1.55 g. of its 15β-hydroxy isomer and 1.2 g. of their mixture. The title compound showed the following physical characteristics:- TLC (developing solvent, benzene-ethyl acetate = 2:1); Rf = 0.40, (16β-hydroxy isomer, Rf = 0.50); IR (liquid film):ν; 3430, 2940, 2850, 1740, 1600, 1585, 1495, 1440, 1380, 1255 cm $^{-1}$; NMR (CDCl$_3$ solution): δ ; 7.40–6.80 (4H, m), 5.90–4.92 (5H, m), 4.80–2.80 (10H, m).

REFERENCE EXAMPLE 22

Methyl 9α,11α,15α-tris(2tetrahydropyranyloxy)-16-(4-chlorophenoxy)-17,18,19,20-tetranorprosta-cis-5,trans-13-dienoate By proceeding as described in Reference Example 4 but replacing the methyl 9α,15α-dihydroxy-11α-(2-tetrahydropyranyloxy)-16-phenoxy-17,18,19,20-tetranorprostacis-5,trans-13-dienoate by 303 mg. of methyl 9α,15α-dihydroxy-11α-(2-tetrahydropyranyloxy)-16-(4-chlorophenoxy)-17,18,19,20tetranorprosta-cis-5,-trans-13-dienoate (prepared as described in Reference Example 21) dissolved in 5 ml. of methylene chloride and utilizing 20 mg. of p-toluenesulphonic acid and 0.27 ml. of 2,3-dihydropyran, there were obtained 350 mg. of the title compound having the following physical characteristics: TLC (developing solvent, methylene chloride-methanol = 19:1); Rf = 0.73; IR (liquid film):ν; 2950, 2850, 1740, 1685, 1600, 1580, 1490, 1355, 1250, 1030, 980 cm$^{-1}$; NMR (CCl$_4$ solution): δ; 7.5–6.6 (4H, m), 6.0–5.0 (4H, m), 5.0–3.0 (17H, m).

REFERENCE EXAMPLE 23

Methyl 2-phenylseleno-9α,11α,15α-tris(2-tetrahydropyranyloxy)-16-(4-chlorophenoxy)-17,18,19,20-tetranorprostacis-5,trans-13-dienoate By proceeding as described in Reference Example 5 but replacing the methyl 9α,11α,15α-tris(2-tetrahydropyranyloxy)-16-phenoxy-17,18,19,20-tetranorprosta-cis-5,trans-13-dienoate by 142 mg. of methyl 9α,11α,15α-tris(2-tetrahydropyranyloxy)-16-(4-chlorophenoxy)-17,18,19,20-tetranorprosta-cis-5trans-13-dienoate (prepared as described in Reference Example 22) dissolved in 1.5 ml. of tetrahydrofuran and utilizing a solution of 0.066 ml. of diisopropylamine in 1.5 ml. of tetrahydrofuran, 0.27 ml. of a 1.4M solution of n-butyllithium in n-hexane and a solution of 150 mg. of diphenyldiselenide in 2 ml. of tetrahydrofuran, there were obtained 102 mg. of the title compound having the following physical characteristics: TLC (developing solvent, benzene-ethyl acetate = 4:1); Rf = 0.57; NMR (CCl$_4$ solution): δ ; 8.0–6.5 (9H,m), 6.0–5.0 (4H, m), 5.0–3.0 (17H, m).

EXAMPLE 17

Methyl 9α,11α,15α-tris(2-tetrahydropyranyloxy)-16-(4-chlorophenoxy)-17,18,19,20-tetranorprosta-trans-2,cis-5,trans-13-trienoate By proceeding as described in Example 3 but replacing the methyl 2-phenylseleno-9α,11α,15α-tris(2-tetrahydropyranyloxy)-16phenoxy-17,18,19,20-tetranorprosta-cis-5,trans-13-dienoate by 176 mg. of methyl 2-phenylseleno-9α,11α,15α-tris(2-tetrahydropyranyloxy)-16-(4-chlorophenoxy)-17,18,19,20-tetranorprosta-cis-5,trans-13-dienoate (prepared as described in Reference Example 23) dissolved in 5 ml. of a mixture of ethyl acetate and tetrahydrofuran (2:1) and utilizing 0.15 ml. of 30% hydrogen peroxide, there were obtained 136 mg. of the title compound having the following physical characteristics: TLC (developing solvent, benzene-ethyl acetate = 4:1); Rf = 0.47; NMR (CCl$_4$ solution): δ ; 5.45–6.5 (5H, m), 6.1–5.0 (5H, m), 5.0–3.1 (17H, m).

EXAMPLE 18

Methyl 9α,11α,15α-trihydroxy-16-(4-chlorophenoxy)-17,18,19,20-tetranorprosta-trans-2,cis-5,trans-13-trienoate [or 16-(4-chlorophenoxy)-17,18,19,20-tetranortrans-Δ$^2$-PGF$_{2α}$ methyl ester]

By proceeding as described in Example 10 but replacing the methyl 9α,11α-bis(2-tetrahydropyranyloxy)-15ξ-hydroxy-16-phenoxy-17,18,19,20-tetranorprosta-trans-2,cis-5,trans-13-trienoate by 136 mg. of methyl 9α,11α,15α-tris(2-tetrahydropyranyloxy)-16-(4-chlorophenoxy)-17,18,19,20-tetranorprosta-trans-2,cis-5,trans-13-trienoate (prepared as described in Example 17) dissolved in a mixture of 4.5 ml. of tetrahydrofuran and 2.1 ml. of 1N hydrochloric acid, there were obtained 59 mg. of the title compound having the following physical characteristics: TLC (developing solvent, chloroform-tertrahydrofuran-acetic acid = 10:2:1); Rf = 0.22 IR (liquid film): ν; 3360, 3010, 2925, 1715, 1650, 1595, 1485, 1165, 970 cm$^{-1}$; NMR (CDCl$_3$ solution): δ; 7.58–6.42 (5H, m), 6.04–5.05 (5H, m) 4.75–4.30 (1H, m), 4.30–3.53 (7H, m), 3.53–2.74 (3H,m).

The present invention includes within its scope pharmaceutical compositions which comprise at least one pharmacologically active prostaglandin analogue of general formula VII or a cyclodextrin clathrate thereof, or when R represents a group COOR$^3$ in which R$^3$ represents a hydrogen atom, a non-toxic salt thereof, together with a pharmaceutical carrier or coating. In clinical practice such novel compounds will normally be administered orally, rectally vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweentening, flavouring, perfuming and preserving agents. The compositions according to the invention for oral administration also include capsules of absorbable material such as gelatin containing one or more of the active substances with or without the addition of diluents or excipients.

Solid compositions for rectal administration include suppositories formulated in manner known per se and containing one or more of the active compounds.

Solid compositions for vaginal administration include pessaries formulated in manner known per se and containing one or more of the active compounds.

Preparations according to the invention for parenteral administration include sterile aqueous or non-aqueous solutions, suspensions, or emulsions. Examples of non-aqeuous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 0.05 and 500 μg. by oral, intravaginal, intrauterine, intravenous, intramuscular and extraovular administration in the termination of pregnancy and induction of labour, in treatment of impaired fertility and in contraception and menstrual regulation. In domestic female mammals such as cows, mares, sows ewes and bitches, the doses are generally between 0.01 and 50 mg./animal by intramuscular, subcutaneous, intrauterine, intravaginal and intravenous administration for the control and synchronisation of oestrus, treatment of impaired fertility and the induction of abortion and labour.

The following Examples illustrate pharmaceutical compositions according to the invention.

EXAMPLE 19

16-Phenoxy-17,18,19,20-tetranor-trans-$\Delta^2$-PFG$_{2\Delta}$ methyl ester (2 mg.) was dissolved in ethanol (10 ml.), mixed wih mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 μg. of 16-phenoxy-17,18,19,20-tetranor-trans-$\Delta^2$PFG$_{2\alpha}$methyl ester which after swallowing of the capsule is released into the stomach.

EXAMPLE 20

16-(3-Chlorophenoxy)17,18,19,20-tetranor-trans-$\Delta^2$PFG$_{2\alpha}$ alcohol (2 mg.) was dissolved in ethanol (10 ml.), mixed with mannitol (18.5 g.), sieved through 30-mesh sieve, dried at 30° C. for 90 minutes and again sieved through a 30-mesh sieve. Aerosil (microfine silica; 200mg.) was added and the powder obtained was machine-filled into one hundred No. 2 hard gelatin capsules to give capsules each conaining 20 μg. of 16-(3-chlorophenoxy)-17,18,19,20-tetranor-trans-$\Delta^2$-PFG$_{2\alpha}$ alcohol which after swallowing of the capsule is released into the stomach.

We claim:
1. A compound of the formula

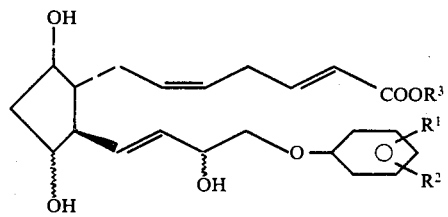

wherein $R^1$ and $R^2$, which may be the same or different, each represent a hydrogen or halogen atom, a trifluoromethyl group, or a straight- or branched-chain alkyl or alkoxy group containing from 1 to 4 carbon atoms, $R^3$ represents a hydrogen atom or a straight- or branched-chain alkyl group containing from 1 to 12 carbon atoms and the double bonds depicted in positions $C_{2-3}$, $C_{5-6}$ and $C_{13-14}$ are trans, cis and trans respectively, the cyclodextrin clathrates thereof and non-toxic salts thereof.

2. A compound according to claim 1 wherein $R^1$ represents a hydrogen atom and $R^2$ represents a hydrogen or chlorine atom or a trifluorometyl group.

3. A compound according to claim 1 wherein $R^3$ represents a hydrogen atom or a straight- or branched-chain alkyl group, containing from 1 to 4 carbon atoms.

4. A compound according to claim 3 wherein $R^3$ represents a methyl group.

5. A compound according to claim 1 wherein the hydroxy groups depicted in formulae VII, VIIIA and VIIIB in claim 1 in α- or β-configuration are attached to the carbon atom in α-configuration.

6. A compound according to claim 1 which is methyl 9α,11α,15α-trihydroxy-16-(3-trifluoromethylphenoxy)-17,18,19,20-tetranorprosta-trans-2,cis-5,trans-13-trienoate.

7. A compound according to claim 1 which is methyl 9α,11α,15α-trihydroxy-16-phenoxy-17,18,19,20-tetranorprosta-trans-2,cis-5,trans-13-trienoate.

8. A compound according to claim 1 which is methyl 9α,11α,15α-trihydroxy-16-(3-chlorophenoxy)-17,18,19,20-tetranorprosta-trans-2,cis-5,trans-13-trienoate.

9. A compound according to claim 1 which is methyl 9α,11α,15α-trihydroxy-16-(4-chlorophenoxy)-17,18,19,20-tetranorprosta-trans-2,cis-5, trans-13-trienoate.

* * * * *